United States Patent [19]

Andrews et al.

[11] Patent Number: 5,187,080

[45] Date of Patent: *Feb. 16, 1993

[54] **DNA ENCODING AN ANTIGENIC PROTEIN DERIVED FROM *EIMERIA TENELLA* AND VACCINES FOR PREVENTION OF COCCIDIOSI

Figure 1

```
[gln]asp tyr pro thr ala val thr leu asp(cys)lys(glu)ala
    |----------------PAP---------------------->
                                  |-----CH3----------
                                                |V7 met asn lys leu arg lys ala ala gly leu pro ala phe glu asp ala gly
-----------------------------CH3-------------------------------
-----------------------------V7--------------------------------
     |---------------------------CN1----------------------------- asp thr phe val leu pro ala tyr(ser his)glu glu ser arg ala ala pro val
--CH3-----|  |--------------------CH2'-----------------
-------V7-----|                               |--------V6------------
-------------------CN1------------------------
                                              |----R2--------- ala glu thr leu trp lys thr glu ile cys pro lys val leu gly gly gly arg
---CH2'--->              |------------------V4--------------------
-V6---|  |---------------------------V2---------------------------
                         ------------------R2--------------------
                                                     |-------CH5----- ser arg asn val thr glu ala val lys leu thr gly asn phe ala tyr tyr pro
---------V4-----------|  |-----------------------V5----------------------
---------V2-----------|  |-----------------------V1----------------------
--R2--|
               -----------------CH5---------------------->
|-------------------------R1------------------------------- val thr asp gly lys lys glu cys ser asp ala val glu tyr trp lys gly gly
----------V5-----------------|                          |---CH2----
---------------------------V1---------------------------
-----------------------R1-------------------------->       |--R4-- leu ser gln phe asn asp thr ile pro pro thr phe gln ala leu asn asp pro
------------------------------CH2---------------------------->
----------V1--------------->
-------------------------R4---------------------------
                                                    |---R2'---- val val tyr asn asp arg ala val ser phe val ala leu tyr asn pro lys thr
-------R4------------------->        |----------CH1-----------------
         |--------CH4-------------|
---------------R2'----------------------------------------> ser pro val val ser(cys)val leu leu gln(cys)pro asn ala gly val gly gly
---------------------------CH1-------------------------------|
```

Figure 3a

```
                              AGATCTATCAAGCAATAATCATCTA
CCTCCAAATATATGCTATGAAATGC7AAATT8CGTGAGAGTGATTCGTCACAGCAACGTC
TCATGCAGAGTGCCCGAGAACTGA5GGGAGAAACAGTGGAGTGACCGCGGGTCGCTGGTA
TTTTCTTGCTTTCATTOGCAAACGYGGCATTTTCAAGTGCCATTTTTCTTGTAATCACAT
TAGTTTGCCAGTAAATGAGGGGAATATTCTGGTGTAAGCTGTTCTTCTGGCAGTTTCACG
AGAGTCACACCGTCACCTGGOAGGTAACCTGGAAAGGGGCGGTGGCAGGAATGGCGCAAG
GCATGGAACAATGAAAGCTGAGAGCAGCGTCAAA3GGATGAATTTTCAATTTCACGTTTG
CCCTTAAATCCATTCAAGTGGGCCGAGACCGCTCTCGGAAGYGCAGTCTCGTTTGCGATT
GCATTMCCTGCACACACCTATGACGACGTACGGTGTTGGGCAGAACCTGAACATAGCGTT
TACGTCTAMAGCCGCAGCCCAAAGAAACTCTGCATACTTTTGCCAAGATATTTCAAATAA
AACCTCTTTGCCGAATTGTATTTTCACCCTCTATCTACTATTTCCTGCCCACTATGAGAG
GCAGCAAGC7GTAGCGTGCCTTCCAATGGCCAGCACCAGCGCGCCAG7TAGGGCAGCAGC
TGTCAACCTCGCTGTCATCTGTCAACAGGCCGCCAGAACTCTTCCCATATCTGTCAAAAC
ATATTTATCTGCTCACTTTACAGTTTCTGTACAGTCACTTTTGCATATTATACAATTACT
                         MetAlaArgLeuSerPheValSerLeuLeuSerLeuSer
GTACAGTCATATTTGCTCAAAATGGCTCGTCTTTCTTTTGTTTCTCTTCTTTCTCTGTCA

LeuLeuPheGlyGlnGlnAlaValArgAlaGlnAspTyrProThrAlaV≤----------
CTGCTCTTCGGGCAGCAAGCAGTCAGAGCTCAGGATTACCCAACAGCAGGTGGGCTTTTC

-----------------Intron A-----------------------------
CGCTAGCTGTTTTTGGTCCGATAGCATCGGAGCATCTCCCAAAACGAGGTGCATTCACC -----------------------------≥alThrLeuAspCysLysGluAlaMetAsn
TTTTGCATGTTGTGTGCGGAAATTTTATCAGTTACGCTGGACTGTAAAGAAGCGATGAAC LysLeuArgLysAlaAlaGlyLeuProAlaPheGluAspAlaValGlyAspThrPheVal
AAGCTGAGAAAAGCAGCAGGACTTCCTGCATTCGAAGATGCTGTGGGAGACACATTTGTT LeuProAlaTyrSerHisGluGluSerArgAlaAlaProValAlaGluThrLeuTrpLys
CTACCAGCATACTCGCATGAAGAGTCTAGGGCGGCACCAGTAGCTGAAACTCTCTGGAAG ThrGluIleCysProLysValLeuGly≤-------------------------
ACGGAGATATGCCCCAAAGTCTTAGGAGTAAGCCGTCCACGGCCTTGCATCGTCATGATG
```

Figure 3b

```
-----------------Intron B-------------------------------
TAGTAGGTGTTCTGAGCAGCTTCGTTCTGTGGAACAAGGAACTACACTGTCCTTGAATTT -------------------≥GlyGlyArgSerArgAsnValThrGluAlaValLysLeu
TTAATCTTTTGTTACGTACAGGGCGGAAGGTCCAGGAACGTTACTGAAGCTGTCAAGTTA ThrGlyAsnPheAlaTyrTyrProValThrAspGlyLysLysGluCysSerAspAlaVal
ACTGGCAATTTTGCCTACTACCCCGTCACAGACGGCAAAAAAGAGTGCAGCGATGCTGTG GluTyrTrpLysGlyGlyLeuSerGlnPheAsnAspThrIleProProThrPheGlnAla
GAGTACTGGAAAGGCGGACTTTCTCAGTTCAACGACACAATTCCCCCAACGTTCCAAGCG LeuAsnAspProValValTyrAsnAspArgAlaValSerPheValAlaLeuTyrAsnPro
TTGAACGACCCCGTTGTGTACAATGACAGGGCTGTTTCCTTTGTCGCCCTATACAACCCC LysTnrSerProValValSerCysValLeuLeuGlnCysProAsnAlaGlyValGlyGly
AAAACCAGCCCCGTTGTCAGTTGCGTGCTCCTCCAGTGCCCTAATGCAGGTGTTGGTGGA ArgArgLeuAlaAlaGlyThrThrAspAlaValIleCysLeuThrAsnProAlaProLeu
CGCAGGCTTGCGGCAGGCACGACAGACGCTGTCATTTGCTTGACAAATCCGGCTCCTTTG GluAlaArgSerGlnProPheAs≤------------------------------------
GAAGCAAGGTCACAACCATTCGAGTGAGAGTCAGCTGGTCGCCACTGCAACATGCATCAA -----------------Intron C-------------------------------
TGCGGCAGGTTACACTGGGGGTC7TGAGGTTGGTTGAAGCGCAATCTTCTAATACTTGTT -------------------≥pAspGluGlnTrpLysLysIleValAspSerLe
TGTAATGTTTGTAATGTTTGCGTGCAGCGACGAGCAATGGAAGAAAATTGTTGACTCTCT uSerLeuSerGluGluGluGluGluLysGlyGlyValSerProValValProSerValAl
ATCTCTCTCTGAGGAAGAGGAAGAGAAGGGCGGAGTTTCTCCAGTCGTCCCTTCAGTAGC
```

Figure 3c aLeuIleSerAlaAlaValIleSerAlaPheAlaLeuPhe
CCTCATCTCTGCGGCGGTCATCTCCGCTTTCGCTCTCTTTTAGGCGGGCGCCGGTTGTTA

GTGACACACCAGCATTGGACAGATATGGCGGCGCAAGTTCCTTCCTGAGTGAAATCCTTG

AGTGACAAACGAGCACCTCTCCTGGACGAAATGTGATGAATTAAGACAGCTTTGGTTGTT

TGAAGTGTATGCAAAAGCTACATTTGTAGGGCCCTTTTATAGGATAATCGGAGGAAGCGC

AATTTTATTTAAAACCCTTGCAGAGAGTCGCCACGTGCGAGTGCAAGTGTTGCGCAGTGT

GTGCTGCCAAATGAAATTCTCGATCTTTAGTGTACTCAAGCCAGAAGTTTCGGCGTTGAT

GTACCCGCCGGTGGTATCTGCCATGCCATGCCTGCCTGTTTGGGCAGTACAACCTCATAC

CAAGTGGCTTGTGTCATGGCATGTGTGGCCAAGCTACTTTTAGAGGGACAACAATGGGGA

TATTTTGAAGTATTTCGGATAAATACTCATCTGCTGTCCCTACCCACTGAGGCGCCATGG

Figure 5a

```
                              AGATCTATCAAGCAATAATCATCTA
CCTCCAAATATATGCTATGAAATGC7AAATT8CGTGAGAGTGATTCGTCACAGCAACGTC
TCATGCAGAGTGCCCGAGAACTGA5GGGAGAAACAGTGGAGTGACCGCGGGTCGCTGGTA
TTTCTTGCTTTCATT0GCAAACGYGGCATTTTCAAGTGCCATTTTTCTTGTAATCACAT
TAGTTTGCCAGTAAATGAGGGGAATATTCTGGTGTAAGCTGTTCTTCTGGCAGTTTCACG
AGAGTCACACCGTCACCTGG0AGGTAACCTGGAAAGGGGCGGTGGCAGGAATGGCGCAAG
GCATGGAACAATGAAAGCTGAGAGCAGCGTCAAA3GGATGAATTTTCAATTTCACGTTTG
CCCTTAAATCCATTCAAGTGGGCCGAGACCGCTCTCGGAAGYGCAGTCTCGTTTGCGATT
GCATTMCCTGCACACACCTATGACGACGTACGGTGTTGGGCAGAACCTGAACATAGCGTT
TACGTCTAMAGCCGCAGCCCAAAGAAACTCTGCATACTTTTGCCAAGATATTTCAAATAA
AACCTCTTTGCCGAATTGTATTTTCACCCTCTATCTACTATTTCCTGCCCACTATGAGAG
GCAGCAAGC7GTAGCGTGCCTTCCAATGGCCAGCACCAGCGCGCCAG7TAGGGCAGCAGC
TGTCAACCTCGCTGTCATCTGTCAACAGGCCGCCAGAACTCTTCCCATATCTGTCAAAAC
ATATTTATCTGCTCACTTTACAGTTTCTGTACAGTCACTTTTGCATATTATACAATTACT
                       MetAlaArgLeuSerPheValSerLeuLeuSerLeuSer
GTACAGTCATATTTGCTCAAAATGGCTCGTCTTTCTTTTGTTTCTCTTCTTTCTCTGTCA

LeuLeuPheGlyGlnGlnAlaValArgAlaGlnAspTyrProThrAlaV≤----------
CTGCTCTTCGGGCAGCAAGCAGTCAGAGCTCAGGATTACCCAACAGCAGGTGGGCTTTTC

-------------------Intron A----------------------------------
CGCTAGCTGTTTTTGGTCCGATAGCATCGGAGCATCTCCCAAAACGAGGTGCATTCACC ---------------------------------≥alThrLeuAspCysLysGluAlaMetAsn
TTTTGCATGTTGTGTGCGGAAATTTTATCAGTTACGCTGGACTGTAAAGAAGCGATGAAC LysLeuArgLysAlaAlaGlyLeuProAlaPheGluAspAlaValGlyAspThrPheVal
AAGCTGAGAAAAGCAGCAGGACTTCCTGCATTCGAAGATGCTGTGGGAGACACATTTGTT LeuProAlaTyrSerHisGluGluSerArgAlaAlaProValAlaGluThrLeuTrpLys
CTACCAGCATACTCGCATGAAGAGTCTAGGGCGGCACCAGTAGCTGAAACTCTCTGGAAG ThrGluIleCysProLysValLeuGly≤---------------------------------
ACGGAGATATGCCCCAAAGTCTTAGGAGTAAGCCGTCCACGGCCTTGCATCGTCATGATG
```

Figure 5b

```
------------------------Intron B------------------------------
TAGTAGGTGTTCTGAGCAGCTTCGTTCTGTGGAACAAGGAACTACACTGTCCTTGAATTT --------------------≥GlyGlyArgSerArgAsnValThrGluAlaValLysLeu
TTAATCTTTTGTTACGTACAGGGCGGAAGGTCCAGGAACGTTACTGAAGCTGTCAAGTTA ThrGlyAsnPheAlaTyrTyrProValThrAspGlyLysLysGluCysSerAspAlaVal
ACTGGCAATTTTGCCTACTACCCCGTCACAGACGGCAAAAAAGAGTGCAGCGATGCTGTG GluTyrTrpLysGlyGlyLeuSerGlnPheAsnAspThrIleProProThrPheGlnAla
GAGTACTGGAAAGGCGGACTTTCTCAGTTCAACGACACAATTCCCCCAACGTTCCAAGCG LeuAsnAspProValValTyrAsnAspArgAlaValSerPheValAlaLeuTyrAsnPro
TTGAACGACCCCGTTGTGTACAATGACAGGGCTGTTTCCTTTGTCGCCCTATACAACCCC LysThrSerProValValSerCysValLeuLeuGlnCysProAsnAlaGlyValGlyGly
AAAACCAGCCCCGTTGTCAGTTGCGTGCTCCTCCAGTGCCCTAATGCAGGTGTTGGTGGA ArgArgLeuAlaAlaGlyThrThrAspAlaValIleCysLeuThrAsnProAlaProLeu
CGCAGGCTTGCGGCAGGCACGACAGACGCTGTCATTTGCTTGACAAATCCGGCTCCTTTG GluAlaArgSerGlnProPheAs≤-----------------------------------
GAAGCAAGGTCACAACCATTCGAGTGAGAGTCAGCTGGTCGCCACTGCAACATGCATCAA ---------------------Intron C-------------------------
TGCGGCAGGTTACACTGGGGGTC7TGAGGTTGGTTGAAGCGCAATCTTCTAATACTTGTT -----------------------≥pAspGluGlnTrpLysLysIleValAspSerLe
TGTAATGTTTGTAATGTTTGCGTGCAGCGACGAGCAATGGAAGAAAATTGTTGACTCTCT uSerLeuSerGluGluGluGluGluLysGlyGlyValSerProValValProSerValAl
ATCTCTCTCTGAGGAAGAGGAAGAGAAGGGCGGAGTTTCTCCAGTCGTCCCTTCAGTAGC aLeuIleSerAlaAlaValIleSerAlaPheAlaLeuPhe
CCTCATCTCTGCGGCGGTCATCTCCGCTTTCGCTCTCTTTTAGGCGGGCGCCGGTTGTTA
```

Figure 5c

GTGACACACCAGCATTGGACAGATATGGCGGCGCAAGTTCCTTCCTGAGTGAAATCCTTG

AGTGACAAACGAGCACCTCTCCTGGACGAAATGTGATGAATTAAGACAGCTTTGGTTGTT

TGAAGTGTATGCAAAAGCTACATTTGTAGGGCCCTTTTATAGGATAATCGGAGGAAGCGC

AATTTTATTTAAAACCCTTGCAGAGAGTCGCCACGTGCGAGTGCAAGTGTTGCGCAGTGT

GTGCTGCCAAATGAAATTCTCGATCTTTAGTGTACTCAAGCCAGAAGTTTCGGCGTTGAT

GTACCCGCCGGTGGTATCTGCCATGCCATGCCTGCCTGTTTGGGCAGTACAACCTCATAC

CAAGTGGCTTGTGTCATGGCATGTGTGGCCAAGCTACTTTTAGAGGGACAACAATGGGGA

TATTTTGAAGTATTTCGGATAAATACTCATCTGCTGTCCCTACCCACTGAGGCGCCATGG

TGTTACCTTCCTCATTTGAAGGGGAAAACTTGGTTGATAATTTCTTGTCCTTCAACTTGT

CTTGATAAATCGAAGATTATATTGTAGATAGTATACGTGGTGAACAGTTTTTAGGGAAGA

CTGTAAACCACAAGTTAAACGTAGTCGGAATTC 4  8 12 16 20 24   36

Hours of Sporulation

Figure 7a

```
              GlnAspTyrProThrAlaValThrLeuAspCysLysGluAlaMetAsnLys
              GAGCTCAGGATTACCCAACAGCAGTTACGCTGGACTGTAAAGAAGCGATGAACAAG

LeuArgLysAlaAlaGlyLeuProAlaPheGluAspAlaValGlyAspThrPheValLeu
CTGAGAAAAGCAGCAGGACTTCCTGCATTCGAAGATGCTGTGGGAGACACATTTGTTCTA

ProAlaTyrSerHisGluGluSerArgAlaAlaProValAlaGluThrLeuTrpLysThr
CCAGCATACTCGCATGAAGAGTCTAGGGCGGCACCAGTAGCTGAAACTCTCTGGAAGACG

GluIleCysProLysValLeuGlyGlyGlyArgSerArgAsnValThrGluAlaValLys
GAGATATGCCCCAAAGTCTTAGGAGGCGGAAGGTCCAGGAACGTTACTGAAGCTGTCAAG

LeuThrGlyAsnPheAlaTyrTyrProValThrAspGlyLysLysGluCysSerAspAla
TTAACTGGCAATTTTGCCTACTACCCCGTCACAGACGGCAAAAAGAGTGCAGCGATGCT

ValGluTyrTrpLysGlyGlyLeuSerGlnPheAsnAspThrIleProProThrPheGln
GTGGAGTACTGGAAAGGCGGACTTTCTCAGTTCAACGACACAATTCCCCCAACGTTCCAA

AlaLeuAsnAspProValValTyrAsnAspArgAlaValSerPheValAlaLeuTyrAsn
GCGTTGAACGACCCCGTTGTGTACAATGACAGGGCTGTTTCCTTTGTCGCCCTATACAAC

ProLysThrSerProValValSerCysValLeuLeuGlnCysProAsnAlaGlyValGly
CCCAAAACCAGCCCCGTTGTCAGTTGCGTGCTCCTCCAGTGCCCTAATGCAGGTGTTGGT

GlyArgArgLeuAlaAlaGlyThrThrAspAlaValIleCysLeuThrAsnProAlaPro
GGACGCAGGCTTGCGGCAGGCACGACAGACGCTGTCATTTGCTTGACAAATCCGGCTCCT

LeuGluAlaArgSerGlnProPheAspAspGluGlnTrpLysLysIleValAspSerLeu
TTGGAAGCAAGGTCACAACCATTCGACGACGAGCAATGGAAGAAAATTGTTGACTCTA

SerLeuSerGluGluGluGluGluLysGlyGlyValSerProValValProSerValAla
TCTCTCTCTGAGGAAGAGGAAGAGAAGGGCGGAGTTTCTCCAGTCGTCCCTTCAGTAGCC

LeuIleSerAlaAlaValIleSerAlaPheAlaLeuPheAM
CTCATCTCTGCGGCGGTCATCTCCGCTTTCGCTCTCTTTTAGGCGGGCGCCGGTTGTTAG
```

Figure 7b

TGACACACCAGCATTGGACAGATATGGCGGCGCAAGTTCCTTCCTGAGTGAAATCCTTGA

GTGACAAACGAGCACCTCTCCTGGACGAAATGTGATGAATTAAGACAGCTTTGGTTGTTT

GAAGTGTATGCAAAAGCTACATTTGTAGGGCCCTTTTATAGGATAATCGGAGGAAGCGCA

ATTTTATTTAAAACCCTTGCAGAGAGTCGCCACGTGCGAGTGCAAGTGTTGCGCAGTGTG

TGCTGCCAAATGAAATTCTCGATCTTTAGTGTACTCAAGCCAGAAGTTTCGGCGTTGATG

TACCCGCCGGTGGTATCTGCCATGCCATGCCTGCCTGTTTGGGCAGTACAACCTCATACC

AAGTGGCTTGTGTCATGGCATGTGTGGCCAAGCTACTTTTAGAGGGACAACAATGGGGAT

ATTTTGAAGTATTTCGGATAAATACTCATCTGCTGTCCCTACCCACTGAGGCGCCATGGT

GTTACCTTCCTCATTTGAAGGGGAAAACTTGGTTGATAATTTCTTGTCCTTCAAAAAAAA

AAAAAAAAAAA

```
CTGCTTCATGCAACGCCACATTTTCAAGCTTCACTTTTCTGATACTCACATTATTTTGCCAGCAAGAGA3GGATA

TGTTCGGTGTAAGCTGJTCTTCTGGCAGTTTCATGAGAGTGACAGCGTCACCTGGTGGTAACCTGCGCTGGGGGC

GGCCGGCAGGAATGGCGCAAGGCGTGGAACAATGAACGCTGACAGGCAGCGTCAAAGAGATGAATTTTCAATTTCA

CTTTTGCCATTAAATCCATTCAAGTGGGCCGAGACCGCTY:-TCGAGTGCAGTCTCGTTTGCGTTGGCATTCCCT

GCACACACCTGATGATGACGTAGGGTGTTGCGCAGAACCTGAATATAGCGTTTAGGTCTAGAGCCGCAGCCCTAC

TAAATCTGCACATTCTTGCATGATATTTCAAATAAAACTCTTGCGAAATTATATTTTCACTTTCTATCTACTATT

TGCTGCCCACTATGCGAGGCAGCAAGCCGTAGCGTGCTTCCAATCGCCAGCACCGGCGCGCCAGCTAGGGCAGCA

GCTGTCAACCTCGCTGTCATCTGTCGACAGCCGCCACAACTCTTTTCATATCTGTCAAAACATATTTATCTGCAT
                                                                MetAlaArgLeu
TTTACAGTTTCTGTACAGTCATTTTTGCATTTTATAGTTACTGTACAGTCATATTTGCTCAAAATGGCTCGTCTC
                                                                       *
SerPheValSerLeuLeuSerLeuSerLeuLeuPheGlyGlnGlnAlaAlaArgAlaGlnGluThrTyrProThr
TCTTTTGTTTCTCTTCTTTCTCTGTCACTGCTCTTCGGGCAGCAAGCAGCCAGAGCTCAGGAAACATACCCAACA

AlaG|--------------Intron A--------------------------------------------
GCAGGTGGGCTTTTCCGCTAGCCGTTTTTGGTCTGACAGCATCTGAGTACTTCCCAAAACAGCGTGCATTCTTCT ----------------------------|luThrMetGluCysArgGluAlaMetAsnGluLeuArgLysAlaA
TTTGCATGTTGTGTGCGGAAATTTTATCAGAAACGATGGAGTGTAGAGAGGCGATGAACGAGCTCAGAAAAGCAG laGlyLeuProGluPheGlyAsnAlaValGlyAspAlaValValLeuProAlaTyrSerHisGluAlaArgAlaA
CAGGGCTTCCTGAATTTGGAAATGCTGTTGGAGATGCAGTAGTTCTACCAGCATACTCGCACGAGGCCAGGGCGG laProValAlaGluThrLeuTrpLysThrGluIleCysProLysValLeuGly|-------------------
CACCAGTGGCTGAAACTCTGTGGAAGACGGAAATATGTCCCAAAGTCTTAGGAGTAAGCCGTCCTCTGCATTGTA ----------------------Intron B------------------------------------------
GTCGTCCACTGCATTGTCATGTAGCAGGTGTTCTGAGCAGCTTATCTCTTTAAACAAGGAACTACGCCCTCCTCA ---------------------|GlyAlaArgAlaLysSerValThrGluAlaValLysLeuThrGlyAsnPh
ATTTCTAATCTTTCGCTGCGTACAGGGAGCAAGGGCCAAGAGTGTTACCGAAGCTGTCAAGCTAACTGGCAACTT eAlaTyrTyrProValThrAspGlyLysLysGluCysSerAspAlaLeuGluTyrTrpLysGlyGlyLeuSerGl
TGCCTACTACCCCGTCACCGACGGCAAAAAGAGTGCAGCGATGCTCTGGAGTACTGGAAAGGCGGACTTTCGCA nPheAsnAspLysIleProProThrPheGlnAlaLeuAsnAsnProAlaValTyrAsnAspArgAlaValSerPh
GTTCAACGATAAAATTCCCCCAACATTTCAAGCGTTGAACAACCCCGCTGTGTACAATGACAGGGCCGTCTCCTT eValAlaLeuTyrAsnProLysProSerProValValSerCysValLeuLeuGlnCysProAsnAlaGlyGlyGl
TGTCGCCCTATACAACCCCAAACCCAGCCCCGTTGTTAGTTGCGTACTACTCCAGTGCCCTAATGCAGGAGGTGG
```

Figure 17b yGlyArgLeuAlaAlaGlyThrThrAspAlaValIleCysLeuThrAsnProAlaProLeuAlaAlaGlySe
TGGACGCAGGCTTGCGGGCAGGCACGACAGATGCTGTCATTTGCTTGACAAACCCTGCTCCTTTGCCAGCAGGCTC rProProPheAs|————————Intron C————————
ACCACCATTCGAGTGCAGAATCAGCTGTTCGCCACTGCAACTACATCAACATCAATCATCAAGCCGGCAGGATACACTGGGGCACTT ——————————————————|pAspGluGlnTrpLysLysIl
GAGGTTGGTTGAAGCGCAATCTTCGGTGA4GCTTGTTTTTGTAATTTGCGTGCAGCGACGAGCAATGGAAGAAAT eValAspSerLeuSerGluLysLysGlyValSerProValGlyProSerValAlaLeuIleSerAlaAlaVa
TGTTGACTCTCTATCTGAAAAGAGGGTGAGTTCTCCAGTGGGCCCTTCAGTAGCCCTCATCTCTGCGGGT IIleSerAlaPheAlaLeuPheAM
TATCTCCGCTTTCGCTCTCTTCTAGGCGGGCTACACGGCAGCATTGGACACAGATATGCCACCCCAAACTCCTTCCTG

AGAGAAATCCTTAAATGACAAACGAGCACCTCTCCTGACGAAGTGTGATCAAGATAGCTTATAGTGCTTTGT

TGTTCGAAGTGAAGTATGCAAAGCTACAAAGCTACATTTGTAGGGCCCTTTATAGGATAATCGGAGGAACCCAATTTTA

TTTAAAACCCTTGCAGAGAGTGCCCACGTGCGAGTGCAAGTGTTCGCCGTGTGCTGCCAGTGAAATTCTCG

ATATGTAGGTGTACTCATCATGCCAGAAGTTTCGCCGTTGATGTACCACCGGTGATGTACCACCGGTTCTGTATCATTAGTGCCAAG

TGTTTGGGCAGTACAACCTCATACCAAATGGCCATGCCTTGTGTCACTGCACGTTCTGTATCATTAGTGCCAAG

CAACTGTTTAAAGGGGAGCAGTGGGCAGTGGGATATTTGAAGTATTTGAATAAATACTTTATTTGCTATACCCACCCG

CTGAGCGGCCATGGTTGCTGTCGTCATTTGAGCGGGAGAAACTGATTGATAATTCCTTGTCCTTCAACTGT

CTTGGTAAATCGAGGAATACGTAGTGAGC3ATTTTTTAGGAAGATTGTAAACCACAGTAAAACGTTTAGCCGAC

ATTTTCTACACTCGTACGTCCGAAAAGCCCATAAGCTAGA

Figure 18

```
                      Exon 1 <------|------> Exon 2
E. tenella    MARLSFVSLLSLSLLFGQQAVRAQD YPTAVTLDCKEAMNKLRKAAGLPAFEDAVGDTFVLPAYSHEESRAA
              **********************   ****  *  ****  *   ****       ********  ***
E. neatrix    MARLSFVSLLSLSLLFGQQAARAQETYPTAETMECREAMELRKAAGLPEPGNAVGDAVVLPAYSHEA  PAA Exon 2 <------|------> Exon 3
              PVAETLAKTEICPKVLGGGRSRNVTEAVKLTQNFAYYPVTDGKKECSDAVEYMKGGLSQFNDTIPPTFQALN
              *************  *   *************************  ***********  ********
              PVAETLAKTEICPKVLGGARAKSVTEAVKLTQNFAYYPVTDGKKECSDALEYMKGGLSQFNDKIPPTFQALN Exon 3 <------|------>
              DPVVYNDRAVSFVALYNPKTSPVVSCVLLQCRNAGVGGGRVLAAGTTDAVICLTNPAPLEARSQPFDDEQMKK
              *  ******************  *******************  ***************        ****
              NPAVYNDRAVSFVALYNPKSPVVSCVLLQCRNAGGGGRRLAAGTTDAVICLTNPAPLAAGSPFFDDEQMKK ---> Exon 4
              IVDSLSLSEEEEKGGVSPVVPSVALISAAVTSAPALP
              ******      *  ***********************
              IVDSLS     EKKGGVSPVGPSVALISAAVTSAPALP
```

Figure 19

E. tenella    1 GTGGCCTTTTCCCTAGCTGTTTTGTCCGATAGATCGGACGATCTCCAAACGAGGTGATTCACCT
                **********  ******   ***** *  ******  ***** 
E. neatrix    1 GTGGGCTTTTCCGCTAGCCGTTTTGTCTGACAGATCGAGTACTTCCAAACGGGTGATTCTCT E. tenella   73 TTTGCATGTTGTGTCCGGAAATTTTATCAG
                ****************************
E. neatrix   73 TTTGCATGTTGTGTCGGGAAATTTTATCAG ATGCATGTAGTAGGTGTTCTGAGCAGCTTCGTTCTG
E. tenella    1 GTAAGCCGTCACGCCCTTGCA TCGTC             * ***  *******
E. neatrix    1 GTAAGCCGTCCCTGCATTGCAGTGTCCACTGATTGTATGTAGCAGGTGTCTGAGCAGCTTATCTCTT E. tenella   73 TGGAACAAGGACTACACTGTCTCCTGAATTTTTAATCTTTGTTACGTCAG
                *********  *  * ******  * * ***  *****
E. neatrix   73 TAACAAGGACTACGCCCTCC TCAATTTCTAATCTTTCGCTGGTACAG E. tenella    1 GTGAGACTGAGCTGCTGCCACTGAAGTGATAATCGGGACGGTTACACTGCGGG TCTTGAGGTTGGT
                ********** *** *****  * *******  * *********
E. neatrix    1 GTGAGAATGACGTGTTGCCACTGCCACTGCCAACATACATCAACGGGACGGATACACTGGGGACACTTGAGGTTGGT E. tenella   73 TGAAGCCGAATCTCTAATCTGTTGTTAATGTTTGCCGTGAG
                ************                      *
E. neatrix   73 TGAAGCCGAATCTTC         GGTGAAGCTTGTTGTAA TTTGCGTGCAG

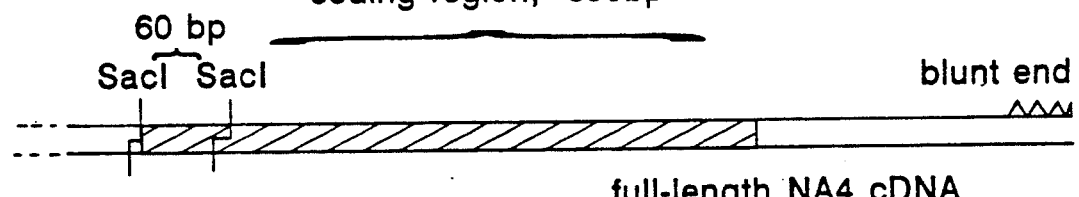
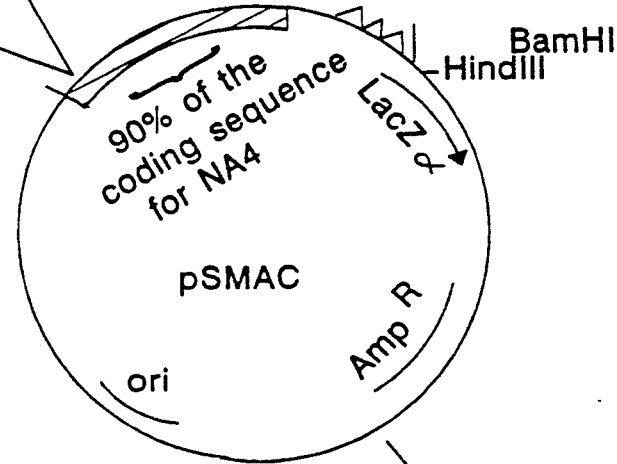
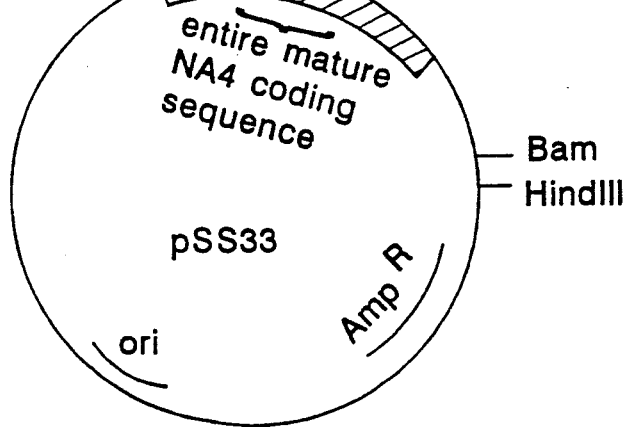
Figure 21

DNA ENCODING AN ANTIGENIC PROTEIN DERIVED FROM *EIMERIA TENELLA* AND VACCINES FOR PREVENTION OF COCCIDIOSIS CAUSED BY *EIMERIA TENELLA*

This is a continuation of U.S. Ser. No. 125,012, filed Nov. 24, 1987, now abandoned, which is a continuation-in-part of U.S. Ser. No. 805,824, filed Dec. 6, 1985, now U.S. Pat No. 4,874,705 which is a continuation-in-part of U.S. Ser. No. 734,085, filed May 16, 1985, which is a continuation-in-part of U.S. Ser. No. 617,483, filed Jun. 5, 1984, now abandoned, the contents of all of which are hereby incorporated by reference into the present application.

BACKGROUND OF THE INVENTION

Throughout this application, various publications are referenced by Arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

The phylum Apicomplexa includes hundreds of different organisms belonging to the order Eucoccidiorida. The genus Eimeria is included within the order of true coccidian agents. Of the organisms belonging to this genus, several species are of recognized importance to the chicken industry. These species include *Eimeria tenella, E. maxima, E. acervulina, E. necatrix, E. brunetti, E. mivati, E. mitis* and *E. praecox.*

Differentiation of species is based on the site of infection within the host and oocyst morphology. To date, biochemical markers have not been used for speciation, although differences have been noted for each of the above species.

For avian Eimeria, the entire life cycle is completed within a single host. The life cycle is complex consisting of asexual and sexual stages depending upon the Eimeria species involved. The infective stage is the sporulated oocyst. Upon being ingested in contaminated feces, food or water, sporulated oocysts excyst within the digestive tract as a result of the combined action of mechanical shearing and enzymatic hydrolysis of the sporocyst cap. The liberated sporozoites traverse epithelial cells within specific regions of the intestine.

Development begins within the Crypt of Lieberkuhn to the level of first generation meronts; the meront is a transitional stage consisting of rounded organisms with a more pronounced nucleus, plus increased energy generating and protein synthesizing capacity. Development of first-generation merozoites follows due to multiple fission of meronts. The release of first-generation merozoites destroys the host cell, and the parasites migrate to infect new host cells undergoing a second asexual cycle. Meronts develop to the level of second-generation merozoites destroying additional epithelial cells as they are released. Further destruction of host cells follows with the liberation of the third-generation merozoites. The number of merozoite generations varies from one Eimeria species to another.

Sexual development commences with the production of microgametes and macrogametes through the process of gametogenesis. Liberated microgametes fertilize macrogametes to form zygotes. Development of immature oocysts is followed by rupture of the host cell. Oocysts, released into the lumen of the gut, are passed through the feces to the environment and mature (sporulate) in the presence of atmospheric oxygen.

The process of parasite development is self-limiting if the host ingests no additional oocysts. However, this proves to be an unrealistic expectation in crowded poultry houses.

Disease due to Eimeria can result in severe economic losses associated with diminished feed efficiency and pathologic manifestations.

The pathology of coccidiosis due to *E. tenella* and *E. necatrix* is in large part related to the rupture of host cells during the release of merozoites, while host cell rupture during the release of *E. maxima* oocysts contributes to the pathology seen with that species. Bleeding within the gut is related to rupture of small capillaries servicing the epithelium. It may be difficult to control the progress of disease using coccidiostats, once asexual development is established. Secondary infection often complicates the disease caused by Eimeria. Death can occcur within 4-7 days in infected birds infected with *E. tenella* or *E. necatrix.* However, death rarely occurs as a result of infection by *E. maxima.*

A consistent property of the coccidia is that the sporozoites initiate the infection process within very specific tissue sites (39, 45, 57). The site specificity of infection is a characteristic commonly used for speciation of Eimeria. For example, the asexual stages of *E. necatrix* show a propensity for invasion of epithelial cells residing within the mid-intestine, while sexual stages develop primarily in the cecal pouches.

Much of the work on immunity to coccidiosis has been confined to humoral immunity, more specifically to serum antibodies. Studies have shown a lack of correlation between serum antibody and resistance to disease (59). However, most available data support the contention that a local response with involvement of the secretory immune system or cell mediated immunity (CMI), or both, are involved in the protective response.

Interference with recognition, penetration and/or attachment of pathogens to host cells has a demonstrated protective effect as shown with viral, bacterial and protozoan models. Genetic deletion of key host cell receptors or pathogen attachment features can prevent the initial colonization process (16, 54). Alternatively, secretory antibodies can interfere with the colonization process by binding to, and consequently masking requisite receptors (32, 74). More than one immunoglobulin class has been reported to have the capacity of interfering with the initial colonization process of *Eimeria tenella* (13). However, recent reports indicate that only production of secretory IgA has been correlated with natural protective immunity (12, 59). Porter and Davis (13) and others (59) reported that secretory IgA neutralizes the extracellular stages of the parasite either by significantly limiting penetration or so debilitating those organisms which did penetrate as to prevent subsequent development.

It has been estimated that an amount approaching $0.5-1.0 billion is spent annually by producers worldwide to combat disease, or to curb the devastating effect of coccidiosis in chickens (39, 52). Even with control measures currently in use, poultry losses are substantial with estimates in the multi-million dollar range (77).

Currently, the most widely used means of controlling Eimeria in chickens is through the application of antiprotozoal chemical feed additives. The specific compotion varies with the coccidiostat used, and each product affects only certain stages of the coccidian life cycle (39, 51, 58). Disadvantages of using coccidiostats are many, including short-term residual protection in birds, occasional diminished performance, invocation of resistance to the drug in parasites, and to some extent, safety. Products currently remain on the market for only a few years because of the development of drug resistant strains. This adds considerable pressure on the cost of development and continued manufacture of efficacious products (51).

Protection of birds by immunization has met with some success. Investigators have been able to invoke limited protection using preparations of killed organisms (1, 41, 43). A more effective approach for immunization of chickens has been with the use of a live protozoal product—e.g. Coccivac ™ (15). The product, being a multivalent composition containing low doses of viable oocysts, is administered in drinking water to invoke a mild parasitemia in birds. A drawback of this product has been occasional depressed performance of birds during the first weeks following administration. Variables such as excessive dosing or moisture content of bedding have even led to severe outbreaks of coccidiosis. See also, U.S. Pat. No. 3,147,186 (1964) which concerns the use of viable, sporulated oocysts of *E. tenella* to immunize chickens and U.S. Pat. No. 4,301,148 (1981) which concerns the use of sporozoites of *E. tenella* for the same purpose.

An alternative means of introducing the live vaccine into broiler houses is by way of the feed. This has been considered in a recent British patent (GB2,008,404A). Prior to mixing with the feed, fully virulent oocysts of *E. tenella* are encapsulated in a water soluble polysaccharide to protect against desiccation. The oocysts are in sufficient amounts only to induce subclinical infection. Though the immunizing ability was found to be excellent, no development of this method is foreseen due to questionable field acceptability. However, if attenuated strains of all the important coccidia could be developed, the procedure may be more acceptable.

Efforts have indeed been made to develop Eimeria lines of reduced virulence. Some species have been successfully attenuated through chicken embryo passage (19, 37, 40, 66). These strains have diminished ability to cause disease, yet have retained sufficient immunogenicity to invoke immunity. Some problems do, however, remain with the handling of these strains. As examples, the attenuated variants of *E. necatrix* have a critical passage limit whereby more or less embryo passage can result in loss of immunogenicity or maintenance of the original virulent form. Furthermore, some attenuated organisms revert to the virulent form upon minimal back-passage through chickens (38, 68). Thus, problems associated with maintaining consistent properties in attenuated organisms are apparent.

Attenuation by precocious selection has also been practiced when Eimeria strains cannot be readily passaged through embryonated eggs. In this process, shed oocysts are harvested late in the prepatent period prior to the onset of heavy oocysts shedding (28, 48, 50, 67). Such selection results in cultures having abbreviated life cycles, and a corresponding diminution in virulence properties (28, 48, 50, 67). Though the trait of precocity for *E. tenella* (29) and *E. acervulina* (49) has been demonstrated to be genetically stable, not enough information is known about this method to assess its usefulness as a tool in the poultry industry.

There is little information available about the surface antigen composition of avian coccidia. Hybridoma cell lines which secrete monoclonal antibodies directed to antigens on the surface of sporozoites of *Eimeria tenella* have been reported (82). The antigens were not identified, other than that their molecular weights were between 13 and 150 kilodaltons. Additionally, no biological significance or described efficacy in a vaccine was attributed to the antigens. European Patent Publication No. 135,712 also discloses monoclonal antibodies which react with sporozoites of *E. tenella*. *E. tenella* sporozoite antigens are disclosed by this publication. Furthermore, European Patent Publication No. 135,073, corresponding to U.S. Pat. No. 4,650,676, discloses monoclonal antibodies which react specifically against merozoites and sporozoites of *E. tenella*. Merozoite antigens derived from *E. tenella* are described.

Previous work in the laboratory of M. H. Wisher suggests the presence of approximately 16 polypeptides identified by surface iodination of excysted sporozoites of *E. tenella* and having molecular weights form 20,000 to greater than 200,000 (81). Additionally, European Patent Publication No. 167,443 discloses extracts from sporozoites or sporulated oocysts of *E. tenella* which may be used as vaccines to protect against coccidiosis. These extracts contain a plurality of polypeptides, one or more of which may be used as an antigen to protect against coccidiosis. Moreover, International Publication No. WO/00528 discloses a cloned gene or fragment thereof from *E. tenella* which encodes antigenic proteins. These proteins bind with a monoclonal or polyvalent antibody directed against an antigenic protein of avian coccidia.

Subunit approaches to vaccine development have proven successful over the past few years. In such approaches, candidate protective antigens are identified and characterized for the purpose of eventual preparation on a large scale. In studying parasite antigens, one research group used monoclonal antibodies to identify a potential protective antigen on the surface of *Babesia bovis* (83). A *B. bovis* antigen of 44,000 daltons has been identified, which when purified and injected into experimental animals afforded some level of protection against primary challenge. An immunologically important 30,000 dalton protein of *Toxoplasma gondii* has also been identified using monoclonal antibodies (31).

Since mid-1981, Danforth and coworkers have published several papers in which they indicate the possibility of producing monoclonal antibodies toward antigens of avian Eimeria species (9, 10, 11). Similarly, Speer, et al. (69, 70) have demonstrated the development of hybridomas against *E. tenella* and some physiologic properties thereof. Antibody-secreting hybridomas have been selected on the basis of an indirect fluorescent antibody test (10). The patterns of reaction, as observed with ultraviolet microscopy, have varied depending upon the monoclonal antibody used. Patterns have included exclusive reaction with sporozoites only vs reaction with sporozoites and merozoites; staining of the anterior portion of the sporozoite vs the entire membrane; and staining of distinct internal organelles vs non-descript internal staining (11).

Although the preparation of murine-origin hybridomas producing monoclonal antibodies is commonly practiced by those familiar with the art, there is nothing to suggest that the direct and specific selection of sporozoite-neutralizing hybridomas against the species *E. tenella* and *E. necatrix* or merozoite-neutralizing hybridomas against the species *E. maxima* will subsequently identify virulence determinants of these species which may be useful in the development of a subunit vaccine.

This invention concerns the identification, characterization, preparation and use of polypeptide antigens for development of immunity to coccidiosis caused by *E. tenella, E. necatrix* and *E. maxima*. Recombinant polypeptide antigens, including fusion proteins, are also described.

The antigens are capable of being precisely dispensed interms of direct antigenic content and cannot cause disease thus avoiding vaccine strain-related outbreaks and reversions or changes in immunologic properties.

Due to the large economic losses caused by coccidiosis in chickens, vaccines against *E. tenella, E. necatrix* and *E. maxima* are desirable. Using hybridoma technology, applicants have identified and purified potential protective antigens for use in subunit vaccines. Use of such a subunit vaccine avoids vaccine strain-related outbreaks and reversions or changes in immunological properties associated with the use of a live vaccine.

The quantity of parasite antigens that can be prepared from the organism is quite low and very costly. Recombinant DNA cloning and expression techniques have opened up a new approach to producing large amounts of protective antigens inexpensively. In simplest terms, these techniques require that DNA sequences encoding all or part of the antigen be placed in a cell, under the control of the genetic information necessary to produce the antigenic protein in that cell. The genetic information may be synthetic DNA (17), genomic (e.g., viral) or chromosomal DNA, or cDNA made from the mRNA encoding the antigen. The latter approach is the most direct method for complex organisms such as *Eimeria* sp.

However, because the cDNA only contains genetic information corresponding to the amino acid sequence of the antigen, it must be inserted into expression vectors that provide the genetic signals necessary for expression of the cDNA gene (i.e., transcription and translation). The antigens can be synthesized either alone or as products fused to another protein in *E. coli*.

Production of an effective subunit vaccine in *E. coli* has been reported for foot and mouth disease virus of swine and cattle (33, 66). Foot and mouth disease virus surface antigens were produced as fusion protein antigens in *E. coli*. Significant levels of virus-neutralizing antibody were raised when cattle and swine were immunized with these antigens. The recombinant DNA-derived antigens gave protection against challenge with foot and mouth disease virus.

In contrast to simple organisms such as foot and mouth disease virus where the genome and surface proteins have been studied extensively, very little is known about the molecular biology of Eimeria. Wang and Stotish (79, 80) reported rapid but transient RNA and protein synthesis in *E. tenella* during the first 6–8 hours after initiation of sporulation and suggested that all protein and nucleic acid synthesis during sporulation occurs in these first few hours. For example, Stotish et al. (72) reported a 30,000 dalton glycoprotein protein component of sporozoite membranes that was synthesized by unsporulated oocysts and later incorporated into sporozoite membranes during the process of sporulation. Recently, Stotish et al. (73) reported isolation and in vitro translation of RNA from unsporulated oocysts, oocysts during sporulation and from sporozoites. The in vitro translation products ranged from less than 10,000 daltons to greater than 200,000 daltons. Patterns for unsporulated and sporulating oocyst RNA directed-protein synthesis were different, suggesting that different RNA populations may exist during sporulation.

In order to produce cDNA encoding the antigenic proteins, it was necessary to determine when the mRNA encoding the antigenic proteins occurred during the life cycle of *E. tenella*. This invention concerns the isolation and characterization of cDNA clones encoding antigenic proteins and the production of engineered antigenic proteins in *E. coli*. It also concerns the extraction of these proteins produced in *E. coli* from the insoluble state and the process to make the proteins immunoreactive with monoclonal antibodies. Finally, this invention shows the preparation and use of the bacterially produced antigenic proteins to produce immunity in chickens to coccidiosis caused by *E. tenella, E. necatrix* and *E. maxima*.

Antigenic proteins derived from *Eimeria tenella* and vaccines containing them for the prevention of coccidiosis caused by *E. tenella* have been described in European Patent Publication No. 164,176.

SUMMARY OF THE INVENTION

A genomic DNA molecule having the nucleic acid sequence set forth in FIG. 5 and encoding an antigenic protein derived from *Eimeria tenella* has been isolated. The native protein has a molecular weight of about 25,000 daltons and is composed of two polypeptides joined by a disulfide bond. One of the polypeptides is characterized by a molecular weight of about 17,000 daltons and by a blocked N-terminal amino acid and has the amino acid sequence set forth in FIG. 5. The other polypeptide is characterized by a molecular weight of about 8,000 daltons and has the amino acid sequence set forth in FIG. 5.

A nucleic acid molecule, which is either cDNA or mRNA, encoding an antigenic polypeptide having a molecular weight of about 25,000 daltons and having the continuous amino acid sequence set forth in FIG. 7 has also been isolated. The cDNA molecule has been inserted into expression vectors capable of expressing the 25,000 dalton polypeptide directly or as a fused polypeptide.

Vector pDET1 encodes a polypeptide having a molecular weight of about 25,000 daltons and the continuous amino acid sequence set forth in FIG. 7. This vector was used to transform *E. coli* host cells and the strain deposited as REN3/pDET1 (ATCC Accession No. 53316).

Vector pDET2 also encodes a polypeptide having a molecular weight of about 25,000 daltons and the continuous amino acid sequence set forth in FIG. 7. This vector was used to transform *E. coli* host cells and the strain deposited as REN3/pDET2 (ATCC Accession No. 53318).

Vector pBGC23 encodes a fused polypeptide having a molecular weight of about 135,000 daltons which has the amino acid sequence of the 25,000 dalton polypeptide set forth in FIG. 7 and, at the amino terminal end, the amino acid sequence of beta-galactosidase. This vector was used to transform *E. coli* host cells and the strain deposited as REN3/pBGC23 (ATCC Accession No. 53317).

Vector pCOC12 encodes a fused polypeptide having a molecular weight of about 65,600 daltons and having the amino acid sequence of the 25,000 dalton polypeptide set forth in FIG. 7 and, at the amino terminal end, the amino acid sequence of prochymosin. This vector was used to transform E. coli host cells and the strain deposited as REN3/pCOC12 (ATCC Accession No. 53314).

Vector pCOC20 encodes a fused polypeptide having a molecular weight of about 56,500 and having the amino acid sequence of the 25,000 dalton polypeptide set forth in FIG. 7 and, at the amino terminal end, the amino acid sequence of prochymosin which has an 83 amino acid deletion from its natural sequence. This vector was used to transform E. coli host cells and the strain deposited as REN3/pCOC20 (ATCC Accession No. 53313).

A method of preparing an antigenic polypeptide, comprises growing any of the host cells of the present invention under appropriate conditions permitting DNA expression and polypeptide production and recovering the polypeptide so produced under suitable conditions. The recovery comprises separating the polypeptide from host cells, purifying the polypeptide, solubilizing the polypeptide, renaturing the polypeptide, and recovering the purified, solubilized, renatured antigenic polypeptide.

A method of conferring upon a chicken active immunity against infection by *Eimeria tenella* comprises administering to a chicken an effective immunizing amount of any of the polypeptides of the present invention.

BRIEF DESCRIPTION OF THE FIGURES

FIG. 1 also shows the overlapping peptides produced by various chemical and enzymatic digestions.

FIG. 2 also shows the position and orientation of the gene for the TA4 antigen within the 5500 bp E. tenella EcoRI DNA fragment.

FIG. 3 shows the DNA nucleotide sequence of the Bgl II-EcoRI DNA fragment of the genomic clone 108-1 depicted in FIG. 2. In addition, FIG. 3 shows the amino acid sequence for the signal peptide and the 17,000 dalton and the 8,000 dalton polypeptide components of the TA4 antigen. FIG. 3 also shows the introns within the gene.

FIG. 5 shows the DNA nucleotide sequence of the Bgl II-EcoRI DNA fragment of the E. tenella genomic clone 108-1 encoding the TA4 protein. The amino acid sequence for the signal peptide and the 17,000 and 8,000 dalton polypeptide components of the TA4 antigen as it occurs in the sporozoite membrane is also shown. Also shown are the introns within the gene as well as the SacI-PvuII DNA used to identify the mRNA by hybridization, and cDNA clones encoding the TA4 protein.

FIG. 7 shows the DNA sequence of the cDNA clone pTCD26 encoding the TA4 antigen.

FIG. 13 also shows the derivation of pCOC20 from pCOC12.

FIG. 14 shows the production of the pCOC12 and pCOC20 proteins in E. coli.

FIG. 17 shows the DNA nucleotide sequence of 2440 bases of the genomic clone 7-49 depicted in FIG. 16. This sequence includes the entire HindIII-BalI region shown in FIG. 16. Also shown is the amino acid sequence inferred for the E. necatrix NA4 antigen.

FIG. 18 shows the amino acid sequence homology between TA4 and NA4 antigens.

FIG. 19 displays the homology of the three introns within the E. tenella and E. necatrix genes encoding the TA4 and NA4 antigens respectively.

FIG. 21 schmetically shows the construction of the recombinant vector pSS33.

DETAILED DESCRIPTION OF THE INVENTION

Figure 1:
FIG. 1 displays the amino acid sequence of the 17,000 dalton polypeptide component of the E. tenella (TA4) antigen determined by microsequencing.

A genomic DNA molecule having the nucleic acid sequence set forth in FIG. 5 and encoding an antigenic protein derived from *Eimeria tenella* has been isolated. The native protein has a molecular weight of about 25,000 daltons and is composed of two polypeptides joined by a disulfide bond. One of the polypeptides is characterized by a molecular weight of about 17,000 daltons and by a blocked N-terminal amino acid and has the amino acid sequence set forth in FIG. 5. The other polypeptide is characterized by a molecular weight of about 8,000 daltons and has the amino acid sequence set forth in FIG. 5.

A nucleic acid molecule, which is either cDNA or mRNA, encoding an antigenic polypeptide having a molecular weight of about 25,000 daltons and having the continuous amino acid sequence set forth in FIG. 7 has also been isolated.

It should be understood that "antigenic polypeptide" as the term is used herein includes preparations prepared under non-reducing conditions as described herein, characterized by the presence within the preparation of a polypeptide having a defined apparent molecular weight on SDS-PAGE under reducing conditions. When present in such preparations, the polypeptide may be bound to another component or components, e.g. to another polypeptide by one or more disulfide bonds or two or more regions within the polypeptide may be bound to one another, e.g. by a disulfide bond. For those preparations characterized by the presence within them of polypeptides with apparent molecular weights of 18,000 or less on SDS-PAGE under reducing conditions the term "fragment" is also used to describe such preparations on the assumption that the preparations include amino acid sequences contained within the intact antigenic protein. In addition the term "fragment" is used to describe amino acid sequences derived from the antigenic protein by proteolytic digestion.

A DNA molecule encoding an antigenic polypeptide having a molecular weight less than about 25,000 daltons and an amino acid sequence included within the amino acid sequence of the protein encoded by the DNA having the nucleic acid sequence set forth in FIG. 5 is contemplated. This DNA molecule may also have additional DNA encoding another amino acid sequence, in which case the molecular weight of the polypeptide would be increased by the molecular weight of the additional amino acid sequence.

A DNA molecule encoding an antigenic polypeptide having a molecular weight greater than about 25,000 daltons which comprises the genomic DNA molecule of the present invention and DNA encoding another amino acid sequence is contemplated.

A DNA molecule encoding an antigenic polypeptide having a molecular weight less than about 25,000 daltons and an amino acid sequence included within the amino acid sequence of the polypeptide encoded by the DNA having the nucleic acid sequence set forth in FIG. 7 is contemplated. This DNA molecule may also have additional DNA encoding another amino acid sequence, in which case its molecular weight would be increased by the molecular weight of the additional amino acid sequence.

The present invention provides a DNA molecule encoding an antigenic polypeptide having a molecular weight greater than about 25,000 daltons which comprises the nucleic acid molecule set forth in FIG. 7 and DNA encoding another polypeptide amino acid sequence.

A recombinant cloning vehicle comprises cloning vehicle DNA and the cDNA of the present invention. The cloning vehicle DNA being characterized by the presence of a first and a second restriction enzyme site and the cDNA being cloned into said sites. A cloning vehicle has been constructed which contains the cDNA clone, designated pTCD26, of the present invention and encodes an antigenic polypeptide having a molecular weight of about 25,000 daltons and the amino acid sequence set forth in FIG. 7. The cloning vehicle may be used to transform a bacterial host cell. An $E.$ $coli$ host cell, JM83, has been transformed with this cloning vehicle and the strain designated as JM83/pTCD26 (ATCC accession No. 53315).

The present invention contemplates an expression vector capable of expressing a 25,000 dalton antigenic protein when introduced into a suitable host cell, which comprises suitable carrier DNA and the genomic DNA set forth in FIG. 5.

When referring to an expression vector carrying the genomic DNA of the present invention, a suitable host cell is a euraryotic cell, i.e. a yeast cell or mammalian cell. Otherwise, a suitable host cell is a bacterial host cell, i.e. $E.$ $coli.$ Also contemplated is an expression vector capable of expressing an antigenic polypeptide having a molecular weight less than about 25,000 daltons, when introduced into a suitable host cell. The vector comprises suitable carrier DNA and DNA encoding an antigenic polypeptide having a molecular weight less than about 25,000 daltons and an amino acid sequence included within the amino acid sequence of the protein encoded by the DNA having the nucleic acid sequence set forth in FIG. 5 or FIG. 7. The non-carrier DNA may also have additional DNA encoding another amino acid sequence, in which case the molecular weight of the polypeptide would be increased by the molecular weight of the additional amino acid sequence.

Suitable carrier DNA would be any DNA segment capable of carrying the genomic DNA molecule of the present invention for use in transforming eucaryotic cells. One such suitable carrier DNA would be that derived from a eucaryotic virus, preferably a commonly used avian virus, such as Marek's disease virus, fowl pox virus or herpes virus of turkeys (HVT) or any mutant derivative thereof.

Also contemplated is an expression vector capable of expressing an antigenic polypeptide having a molecular weight greater than 25,000 daltons, when introduced into a suitable host cell, which comprises suitable carrier DNA and the genomic DNA molecule of the present invention and DNA encoding another amino acid sequence.

A bacterial expression vector capable of expressing a 25,000 dalton antigenic polypeptide when introduced into a suitable bacterial host cell, comprises plasmid DNA and the cDNA of the present invention. When under the control of the lac, lambda $P_R$ and tac promoters this vector is designated pDET1. When under the control of the lac and tac promoters this vector is designated pDET2.

A suitable bacterial expression vector is a double-stranded DNA molecule which includes in 5' to 3' order the following:

a DNA sequence which contains a promoter and operator or just a promoter;

a DNA sequence which contains a ribosomal binding site for rendering the mRNA of the desired gene capable of binding to ribosomes within the host cell an ATG initiation codon;

a restriction enzyme site for inserting a desired gene into the vector in phase with the ATG initiation codon;

a DNA sequence which contains an origin of replication from a bacterial plasmid capable of autonomous replication in the host cell; and a DNA sequence which contains a gene associated with a selectable or identifiable phenotypic trait and which is manifested when the vector is present in the host cell.

The present invention contemplates a bacterial expression vector capable of expressing an antigenic polypeptide having a molecular weight less than about 25,000 daltons when introduced into a suitable bacterial host cell. The vector comprises plasmid DNA and DNA which encodes a polypeptide having an amino acid sequence included within the amino acid sequence set forth in FIG. 7. The non-plasmid DNA may also have additional DNA encoding another amino acid sequence, in which case the molecular weight of the polypeptide would be increased by the molecular weight of the additional amino acid sequence.

The present invention provides a bacterial expression vector capable of expressing a fused polypeptide composed a polypeptide of about 25,000 daltons fused to another amino acid sequence when introduced into a suitable host cell. It comprises plasmid DNA and the cDNA of the present invention fused to DNA encoding another amino acid sequence.

The vector pBGC23 encodes an antigenic fused polypeptide having a molecular weight of about 135,000 daltons and having the amino acid sequence of beta-galactosidase fused to the amino terminal end of the amino acid sequence set forth in FIG. 7.

The vector pCOC12 encodes an antigenic fused polypeptide having a molecular weight of about 65,600 daltons and having the amino acid sequence of prochymosin fused to the amino terminal end of the amino acid sequence set forth in FIG. 7.

The vector pCOC20 encodes an antigenic fused polypeptide having a molecular weight of about 56,500 daltons and having the amino acid sequence of prochymosin, which has an 83 amino acid deletion from its natural sequence, fused to the amino terminal sequence set forth in FIG. 7.

The bacterial expression vectors of the present invention have been used to transform E. coli host cells. The E. coli host cell designated REN3/pBGC23 comprises the vector pBGC23 and has ATCC accession No. 53317. The E. coli host cell designated REN3/pCOC12 comprises the vector pCOC12 and has ATCC accession No. 53314. The E. coli host cell designated REN3/pCOC20 comprises the vector pCOC20 and has ATCC accession No. 53313. The E. coli host cell designated REN3/pDET1 comprises the vector pDET1 and has ATCC accession No. 53316. The E. coli host cell designated REN3/pDET2 comprises the vector pDET2 and has ATCC accession No. 53318.

A method of preparing an antigenic polypeptide, comprises growing any of the host cells of the present invention under appropriate conditions permitting DNA expression and polypeptide production and recovering the polypeptide so produced under suitable conditions. The recovery step comprises first separating the polypeptide from host cells and then purifying it, solubilizing it, renaturing it and finally recovering the purified, solubilized, renatured antigenic polypeptide.

A method of conferring upon a chicken active immunity against infection by Eimeria tenella comprises administering to a chicken an effective immunizing amount of any of the polypeptides of the present invention. The polypeptides may also be administered in any combination of two or more polypeptides.

A vaccine for conferring upon a chicken active immunity against infection by Eimeria tenella comprises per dose an effective immunizing amount of any one of the polypeptides of the present invention and a suitable carrier. The vaccine may also comprise a combination of two or more polypeptides of the present invention and a suitable carrier. In one embodiment, the polypeptide used in the vaccine is the fused polypeptide having a molecular weight of about 135,000 daltons and the amino acid sequence of beta-galactosidase fused to the amino terminal end of the amino acid set forth in FIG. 7. In another embodiment the polypeptide used in the vaccine is the fused polypeptide having a molecular weight of about 65,600 daltons and having the amino acid sequence of prochymosin fused to the amino terminal end of the amino acid sequence set forth in FIG. 7.

A method of protecting a chicken against infection by Eimeria tenella comprises administering to the chicken a suitable dose of any of the vaccines of the present invention.

Figure 8:
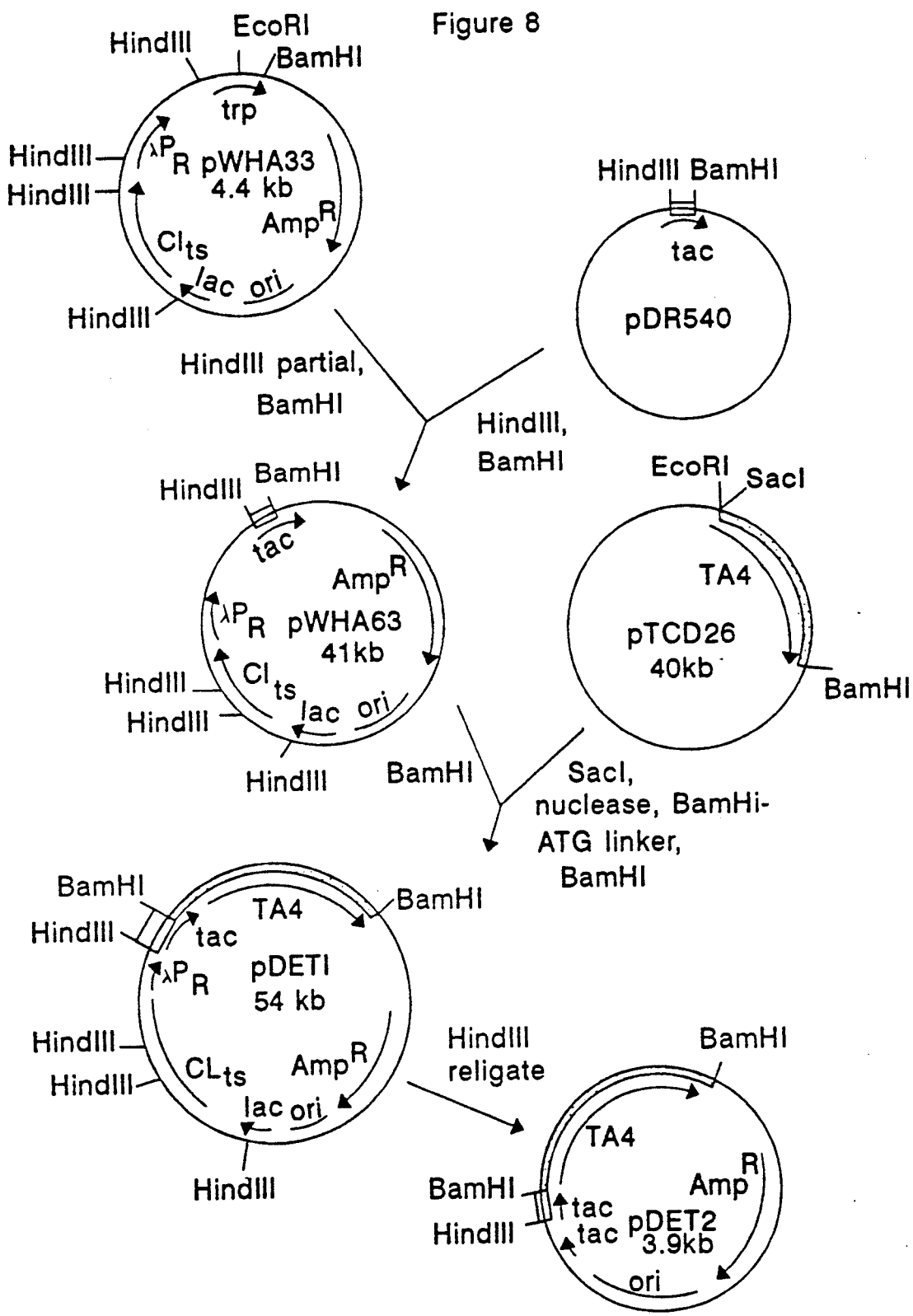
FIG. 8 schematically shows the construction of expression vector pWHA63 and the insertion of the DNA from the cDNA clone pTCD26 into expression vector pWHA63 to generate expression vectors pDET1 and pDET2.
Figure 9:
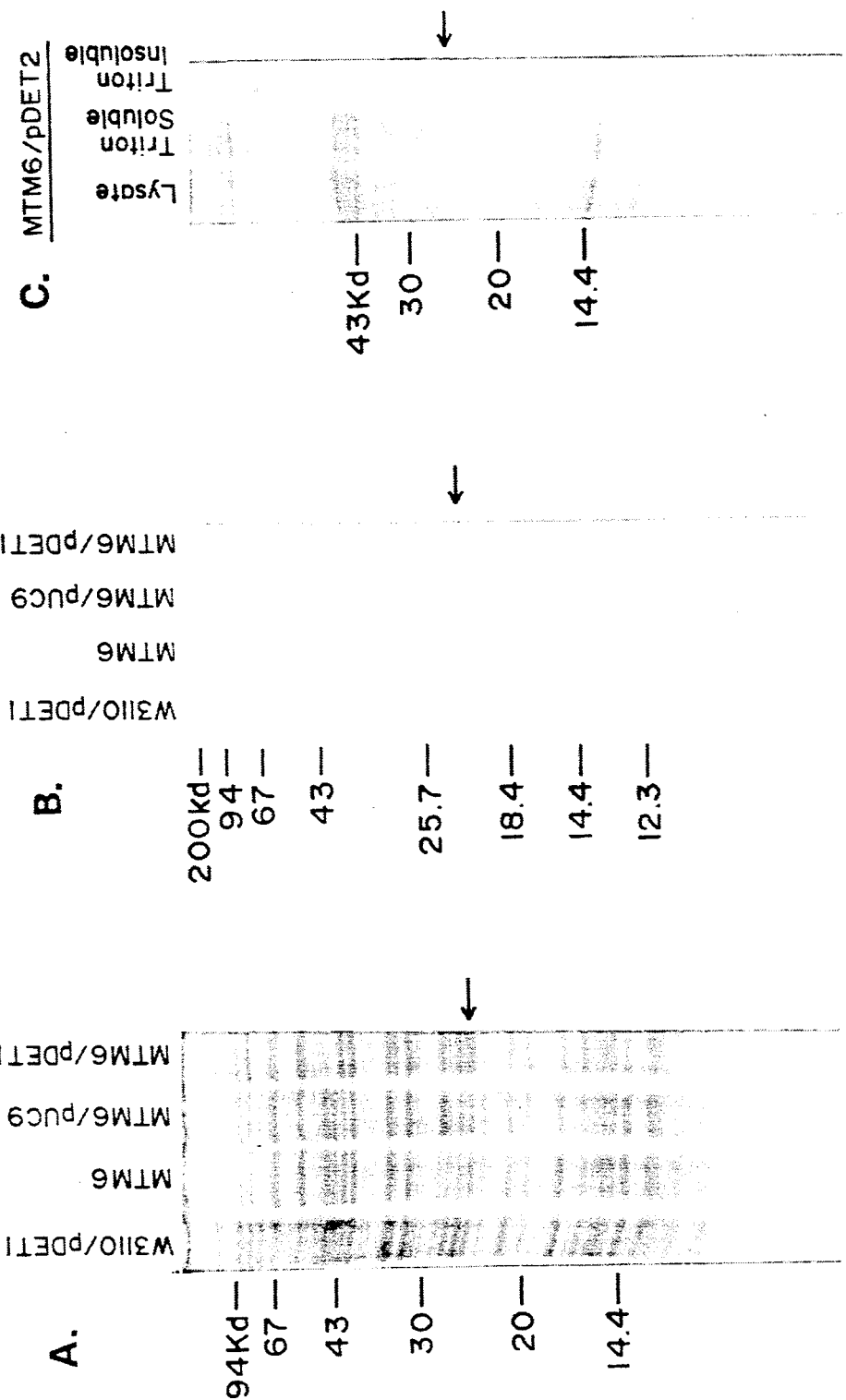
FIG. 9 shows the production of the pDET1/pDET2 protein in Lon+ vs. Lon− protease deficient strains of E. coli.

Plasmid pDET1 encodes a 25,000 dalton polypeptide under the control of the lac, lambda $P_R$ and tac promoters. Plasmid pDET2 encodes a 25,000 dalton polypeptide under the control of the lac and tac promoters (FIG. 8). The greatest yield of the pDET1/pDET2 proteins was achieved in a protease deficient E. coli strain (FIG. 9). The pDET1 and pDET2 proteins were found in the insoluble fraction of a cell lysate.

Figure 10:
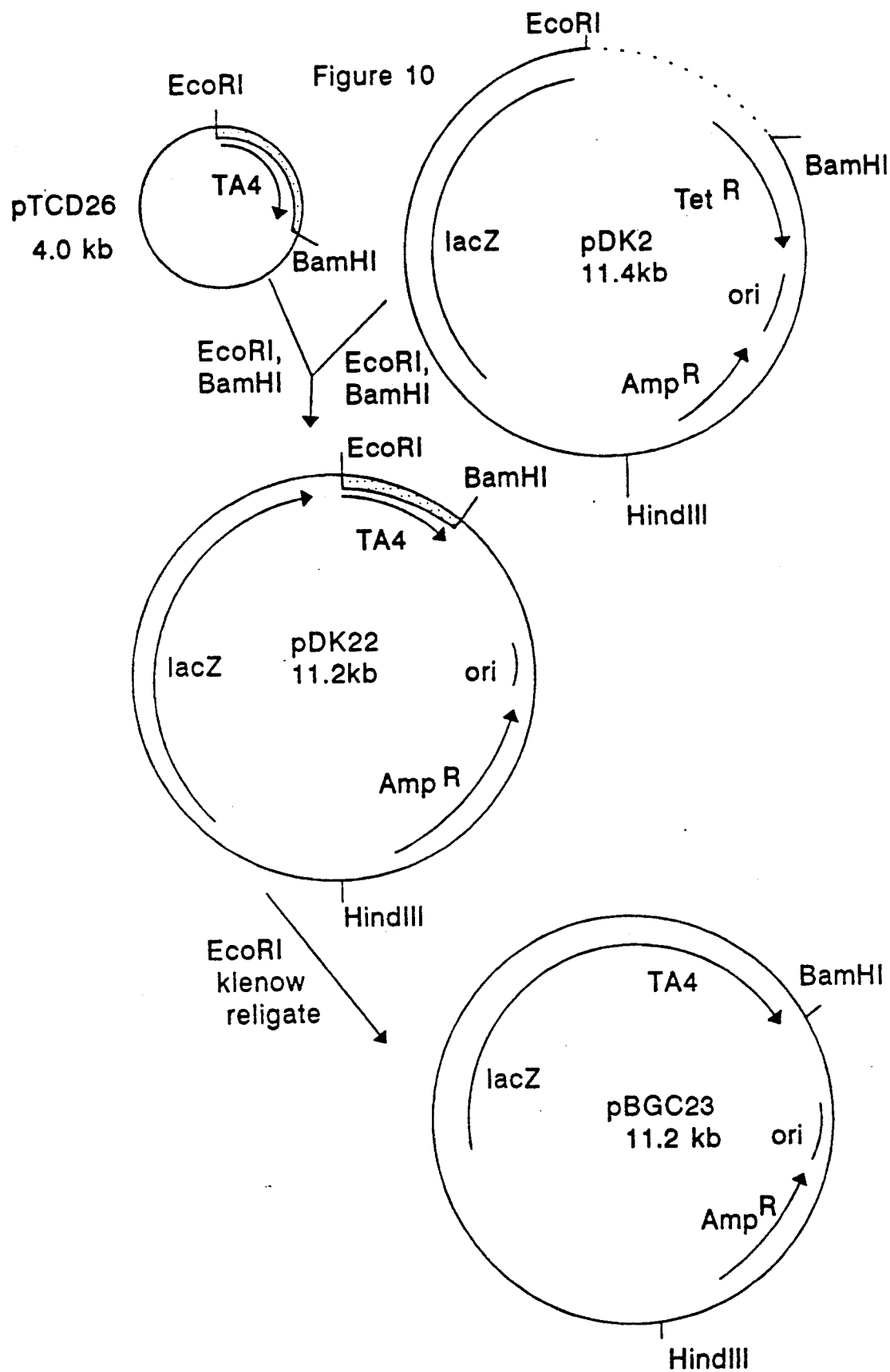
FIG. 10 schematically shows the construction of expression vector pBGC23 fusing the 3' end of the lac Z gene to the 5' end of the sequence encoding the cDNA derived antigenic polypeptide.
Figure 11:
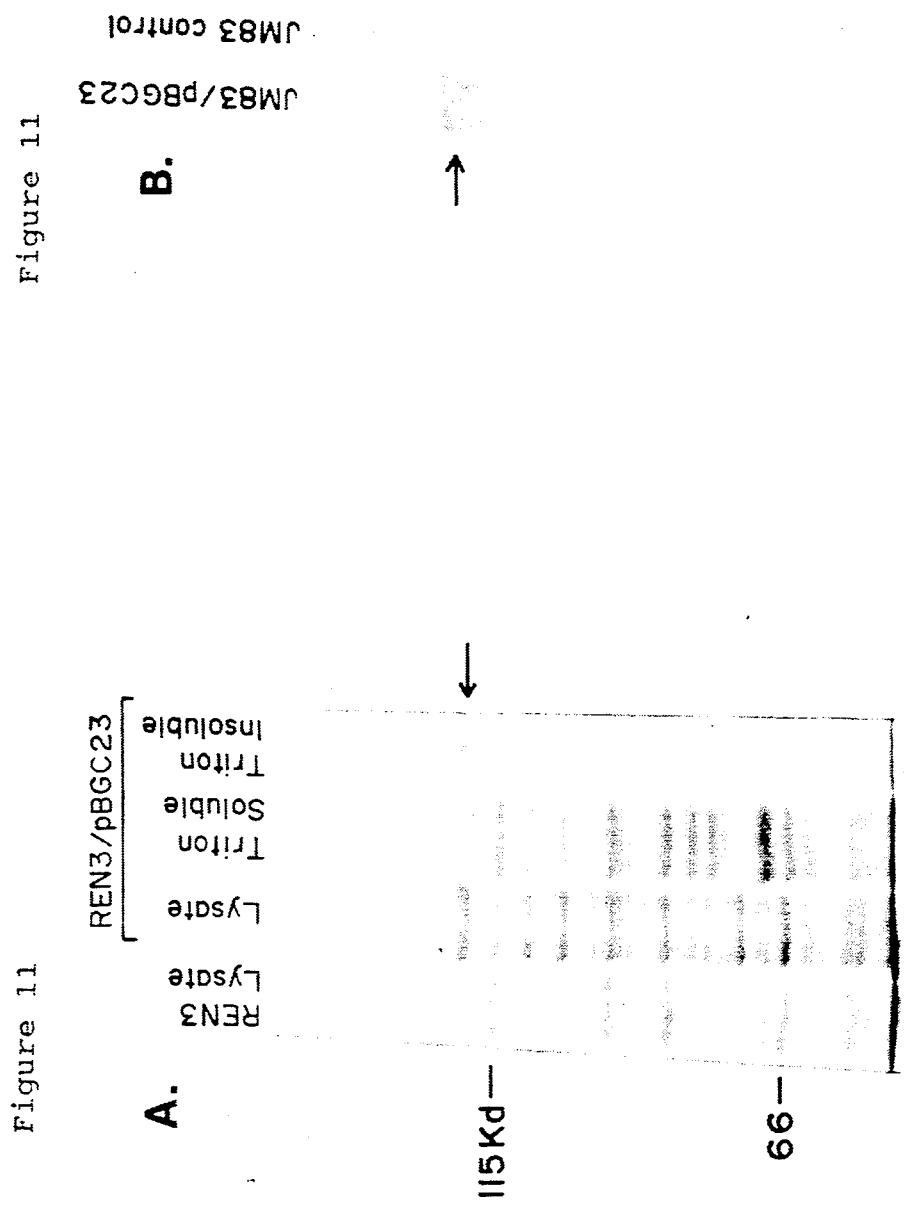
FIG. 11 shows the production of the pBGC23 protein in E. coli.

Plasmid pBGC23 was constructed by fusing the 3' end of the coding sequence of E. coli beta-galactosidase to the 5' end of the coding sequence of the cDNA derived TA4 polypeptide and encodes a fusion protein of approximately 135,000 daltons (FIG. 10). The pBGC23 protein is stable but insoluble in E. coli (FIG. 11).

Figure 13:
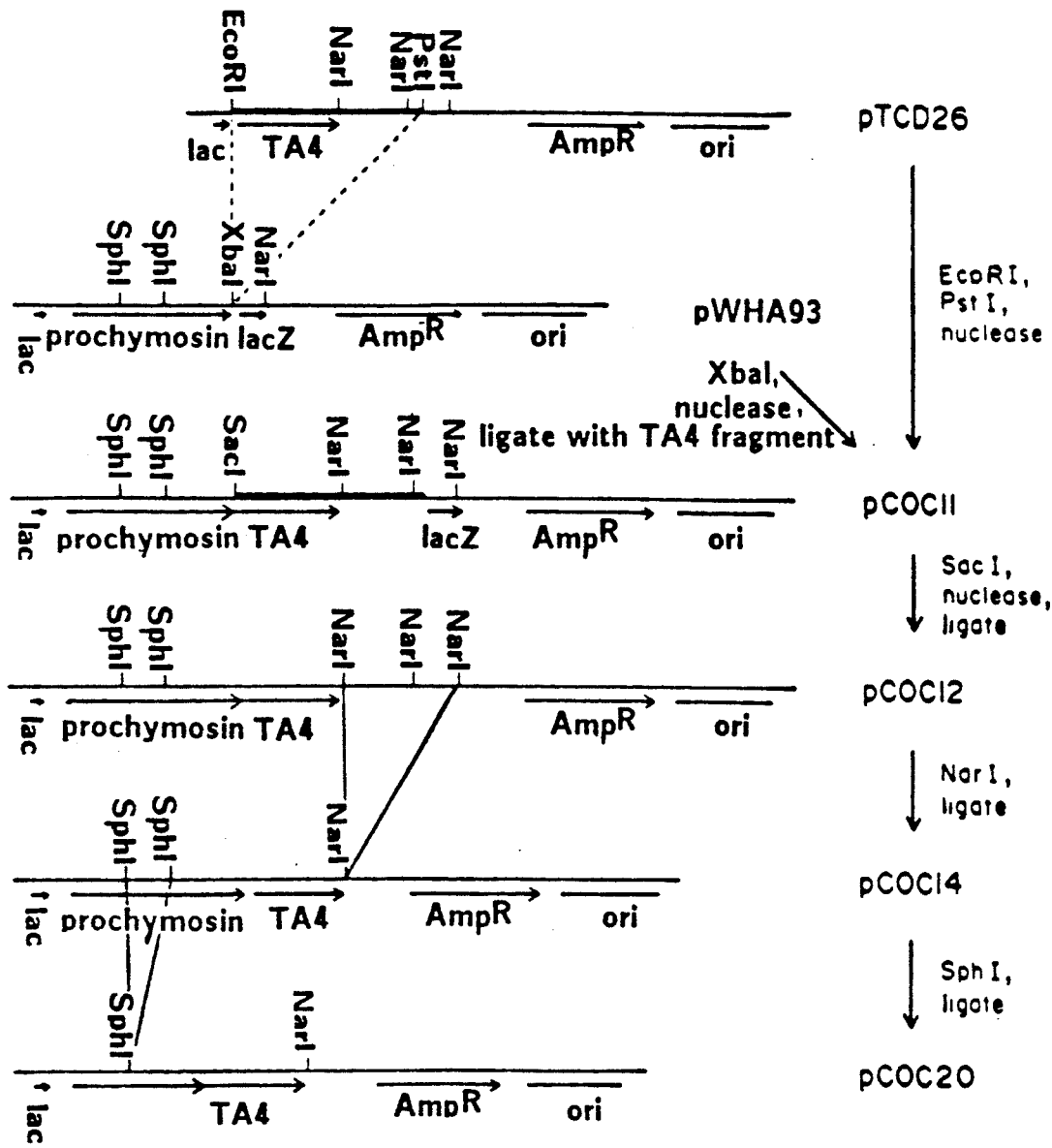
FIG. 13 schematically shows the construction of pCOC12 by fusing the 3' end of the coding sequence of bovine prochymosin to the 5' end of the coding sequence of the cDNA derived antigenic polypeptide.
Figure 14:
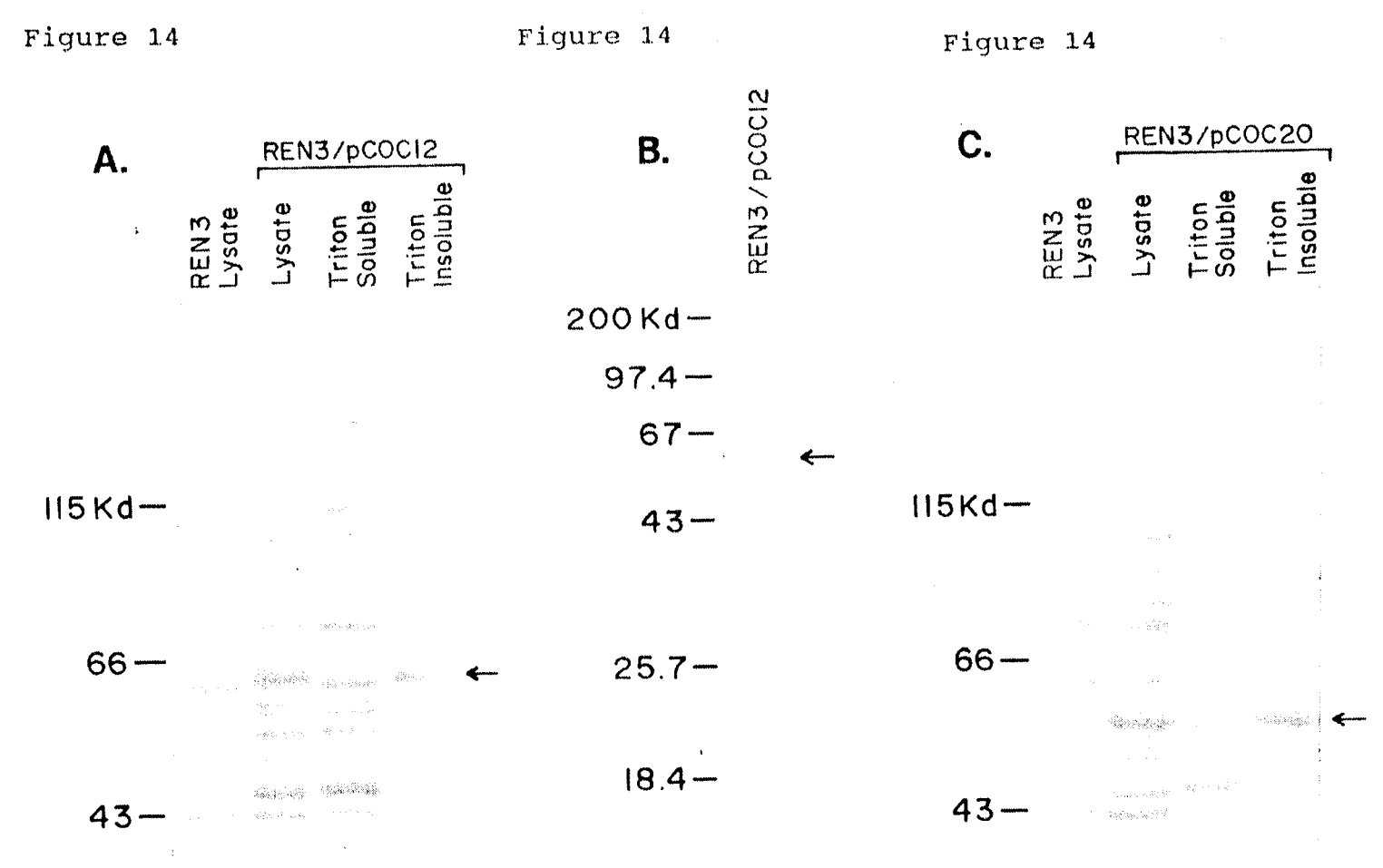

Plasmid pCOC12 was constructed by fusing the 3' end of the coding sequence of bovine prochymosin to the 5' end of the cDNA coding for the TA4 polypeptide and encodes a fusion protein of approximately 65,600 daltons. Plasmid pCOC20 was constructed from pCOC12 by a deletion in the prochymosin domain of the fusion protein and encodes a fusion protein of approximately 56,500 daltons (FIG. 13). The pCOC12 and pCOC20 proteins are stable but insoluble in E. coli (FIG. 14).

The insoluble, bacterially-produced TA4 proteins were not immunoreactive with Ptn 7.2 A4/4, a neutralizing monoclonal raised to E. tenella sporozoites. When the insoluble proteins from pBGC23 and pCOC12 were injected into mice they did not raise antibodies that crossreacted with the TA4 antigen purified from E. tenella.

This invention also concerns a method for extracting the bacterially-produced TA4 proteins from the insoluble state and the process to make the proteins immunoreactive with monoclonal antibody Ptn 7.2 A4/4. This method is applicable to renaturation of prochymosin-TA4 fusion proteins to make them immunoreactive. It involves solubilization of the proteins in 8M urea followed by dilution and renaturation at alkaline pH (pH 11) and back titration to pH 8.3. Alternatively the proteins may be solubilized in 8M urea and the urea removed by dialysis.

When the urea-alkali solubilization/renaturation process was used for the pCOC12 protein the renatured protein had both milk clotting activity and immunoreactivity with monoclonal antibody Ptn 7.2 A4/4. Renaturation conditions were optimized using the pCOC12 protein. The optimal renaturation conditions for pCOC20 protein and pBGC23 protein were found to be the same as those for pCOC12. For pDET2 protein on the other hand optimal renaturation conditions involved urea-dialysis at alkaline pH.

The renatured pBGC23 and pCOC12 proteins elicited antibodies in mice that reacted with the TA4 antigen purified from *E. tenella*. When chickens were immunized with renatured pBGC23 and pCOC12 proteins these proteins elicited serum neutralizing antibodies to *E. tenella* sporozoites and ameliorated coccidiosis in chickens challenged with *E. tenella*.

This invention also encompasses a method for conferring upon a chicken active immunity against infection by *Eimeria tenella* which comprises administering to a chicken an effective immunizing amount of the renatured bacterial TA4 proteins. By this method active immunity can be conferred upon a non-immune chicken. In addition, administration of these materials can be used to increase a relatively low level of immunity in a chicken previously exposed to *E. tenella* and can be used in booster vaccinations.

The bacterial TA4 proteins can be administered to chickens by any of a number of well known methods. Desirably, the administration can involve subcutaneous, intraperitoneal or intramuscular injection at the back of the neck, or any convenient form of oral administration. The amount of antigen comprising an effective immunizing amount can be any amount from about 0.1 microgram to about 1 mg. The amount of antigen is desirably above about 10 micrograms. The preferred amount of antigen is about 500 micrograms per kilogram of body weight. Alternatively, the administration can be oral (e.g., via capsule) or desirably by injection (e.g., subcutaneous, intradermal, or preferably intramuscular injections). If the mode of administration involves injection, any pharmaceutically acceptable carrier can be employed. Suitable carriers include 0.01 to 0.1M, preferably 0.05M, phosphate buffer or 0.8 percent saline.

A vaccine for conferring upon a chicken active immunity against infection by *Eimeria tenella* is provided which comprises an effective immunizing amount of an antigenic material of this invention, i.e., the renatured bacterial TA4 proteins and a suitable carrier. Preferably the effective immunizing amount of the antigenic material in the vaccine is above about 0.1 microgram/kg of body weight of the chicken.

In addition, the carrier desirably also contains a preservative. One particularly suitable preservative is thimerosal (sodium ethylmercurithiosalicylate) which has activity as both a bacteriostat and a fungistat. Desirably, thimerosal is present in the vaccine in a final concentration of $10^{-4}$ percent.

Furthermore, the carrier desirably also contains an immunopotentiator, i.e., a substance which enhances the immune response of the treated animal to the vaccine, including *Salmonella minnesota* LPS at 10 micrograms/dose. Various immunopotentiators known in the art may be used. The adjuvant presently employed is 94% Drakeol 6-VR, 5% Arlacel A, 1% Tween-80. Arlacel A is a mannide monoleate (Sandria Corp.). It is an irritant which has strong immunopotentiating activity when combined with antigens. Drakeol 6-VR is a hypoallergenic light mineral oil product (Penreco Corp.). Tween-80 is a monoleate derivative of polyoxyethylsorbitan and possesses detergent properties. Other suitable carriers or immunopotentiators include aluminum potassium sulfate, aluminum hydroxide, ligand binding subunits of toxin molecules, bioadhesives, lymphokines and water in oil emulsions.

By administering a suitable dose of such a vaccine to a chicken, the chicken is protected against infection by *E. tenella*. The amount of antigenic material per dose should be sufficient to induce production of antibodies to the antigenic material in an animal to which the vaccine is administered. To provide a sufficient degree of immunological response as measured by antibody production and protection, the amount of the antigenic material per dose is desirably above about 20.0 micrograms/kg of body weight of the vaccinated animal. Thus, the amount of antigenic material based upon a 50 gram day-old chick would be above about 1.0 microgram. Presently preferred is a vaccine containing 10 micrograms of antigenic material. In general, the antigen will comprise on a weight basis from about 0.002 percent up to about 0.2 percent of the vaccine and the dose volume will be about 0.1 ml.

EXAMPLE 1

Preparation of *Eimeria necatrix* and *Eimeria tenella* Oocysts, Sporocysts and Sporozoites Coccidia. The purified field isolates of *Eimeria necatrix* and *Eimeria tenella* were originally purchased from Dr. Allen Edgar of the University of Auburn. The purity of each isolate was confirmed using oocyst characteristics and histology of infected intestinal tissue. Oocyst size and shape index were within the range of *E. necatrix* and *E. tenella*, respectively.

Lesions were scored by the method of Johnson and Reid (30) The lesions in infected birds were typical of each respective isolate. At 5 days post-infection histological examination revealed larger second generation schizonts in the subepithelium of the mid-intestine (*E. necatrix*) or the ceca (*E. tenella*). Mortality was experienced with *E. tenella* and *E. necatrix* during severe infections (15,000 and 50,000 oocysts respectively). Single oocyst cloning was periodically done to insure purity of each isolate.

Propagation of Oocysts. Pure cultures of each isolate were routinely passaged in 4- to 6-week old SPF white Leghorn chickens. To avoid extraneous coccidial infections, chickens were reared from 1 day of age in plexiglass isolation units. Oocysts were harvested on day 7 post-infection from the ceca using a trypsin-digest method described by Shirley (66). Sporulated oocysts were typically stored at 24° C. in 2% w/v $K_2Cr_2O_7$.

Isolation of Sporocysts. Sporulated oocysts, ($1 \times 10^8$) which had been partially purified from debris by salt floatation, were washed five times in 0.1M phosphate buffered saline, pH 7.4, (PBS) to remove the potassium dichromate preservative. These oocysts were further cleaned by agitation in a 1.05% sodium hypochlorite solution for 20 minutes followed by five washes in PBS to remove residual sodium hypochlorite and debris. Following the final wash, the cleaned oocysts were resuspended in 10 ml of PBS. Suspended oocysts were then mechanically broken by shaking with an equal volume of glass beads (1.0–1.05 mm). The liberated sporocysts were purified from the oocyst walls and from unbroken oocysts by passage over a glass wool column, centrifuged at 3,000 RPM for ten minutes at 4° C. and resuspended in 10 ml of PBS.

Preparation of Sporozoites. Freshly sporulated oocysts were cleaned by salt floatation, repeated washing and treatment with 1.05% sodium hypochlorite solution. Sporocysts were freed by mechanically breaking oocysts with glass beads (1.0-1.05 mm). To excyst sporozoites, sporocysts were incubated with trypsin and taurodeoxycholic acid (0.25 and 0.50% w/v, respectively) for a period of 1 hour at 41° C. Sporozoites thus obtained were rinsed free of excysting fluid by centrifugation and resuspended in Hank's medium. Fresh Hank's medium was used to dilute sporozoites to the working concentration.

EXAMPLE 2

Generation, Identification and Characterization of Hybridomas

Monoclonal Antibody. Monoclonal antibodies were derived from hybridomas developed using the method of VanDeusen and Whetstone (77). Briefly, Balb/C ByJ mice were repeatedly immunized with $10^6$-$10^7$ intact $E.$ tenella sporozoites. Three days after a final intravenous injection with intact sporozoites, a randomly selected mouse was sacrificed and splenectomized. The splenocytes were separated from fibrous tissue in the organ, and the washed cells fused with the murine plasmacytoma cell line (SP2/OM).

Microneutralization Assay. The microneutralization assay was performed with primary chick kidney cell cultures for $E.$ tenella or embryonic porcine lung cells for $E.$ necatrix. 1- to 2-week-old chicks were sacrificed and aseptically nephrectomized. The cells were plated into 96-well cultures at a density of approximately $10^4$/well in Earle's LAH medium supplemented with 5% heat-inactivated fetal calf serum. Cultures were maintained at 41° C. in a 5% $CO_2$ atmosphere. When cell cultures reached a level of approximately 50% confluency, 50 microliters of hybridoma test or control sample were added to all wells of the plate. Next, about $3 \times 10^4$ sporozoites suspended in 50 microliters of Earle's culture medium were added to all wells of the plate. Twelve to sixteen hours later, the culture supernatant was replaced with fresh Earle's LAH containing 2% heat inactivated fetal calf serum. The cultures were terminated at 40–44 hours post-infection. Culture supernatant was emptied from the plates at that time. Subsequently, cells were fixed to the plates by the addition of methanol acidified with 5% glacial acetic acid. The fixed cultures were stained with 0.1% toluidine blue before examination. Wells were scored as to the approximate percentage level of inhibition of schizogony; neutralization of parasites by monoclonal antibodies was scored on the basis of the maximum serum dilution still affording complete inhibition of schizont development.

Indirect Fluorescent Antibody Screening. IFA slides were prepared with sporozoites of $E.$ tenella or $E.$ necatrix (about $1 \times 10^6$/well). Slides were air dried several hours to overnight before 10 microliters of 1% bovine serum albumin (BSA) was added to each well. Five minutes after adding BSA, 20 microliters of test supernatant was added. Supernatants were incubated at 37° C. for 20 minutes, followed by three rinses with 0.15M PBS with 0.0005% Tween-20 (PBS-Tween). Fluorescein conjugated rabbit anti-mouse antibody (diluted 1:40 in PBS) was added to the samples and allowed to incubate at 37° C. for 20 minutes. The conjugate was rinsed off three times with PBS-Tween before adding mounting medium and cover slip.

Results. Of the several thousand hybridomas developed against Eimeria tenella, 24 were found to produce neutralizing antibodies toward the sporozoite stage of the parasite. All of the hybridomas studied produced antibodies that recognized membrane bound antigens, although only the antibody produced by one hybridoma recognized an internal membrane antigen.

In vitro neutralizing potency was compared for several supernatants after the initial cloning of the respective cell lines. Supernatant from certain lines demonstrated the greatest relative propensity for neutralizing sporozoites of $E.$ tenella. When antibody content was assessed for each of the supernatants tested, it was determined that twenty-fold less of one antibody (designated Ptn 7.2A4/4) was required to neutralize sporozoites than the second most effective neutralizing antibody. Specifically, the amount of Ptn 7.2A4/4 antibody required to neutralize $E.$ tenella is approximately $3.5 \times 10^5$ molecules/sporozoite.

The hybridoma which produces the monoclonal antibody designated Ptn 7.2A4/4 has been deposited with the American Type Culture Collection in Rockville, Md., U.S.A. 20852, and identified by ATCC accession No. HB8561. This deposit was made pursuant to the provisions of the Budapest Treaty on the International Recognition of the Deposit of Microorganisms For The Purposes Of Patent Procedure (hereinafter "Budapest Treaty").

When the monoclonal antibody Ptn 7.2A4/4 was evaluated with $E.$ necatrix, it was observed that a fluorescent staining pattern, similar to that with $E.$ tenella had developed. The monoclonal was therefore studied in the in vitro neutralization assay against $E.$ necatrix. Said monoclonal antibody was found to possess neutralizing activity against $E.$ necatrix at levels within a comparable range observed with a like number of $E.$ tenella sporozoites.

EXAMPLE 3

Identification of the Antigens of $E.$ Tenella Recognized by Neutralizing Monoclonal Antibody Ptn 7.2A4/4

$^{125}$I Labeling of Eimeria Proteins. A total of $2 \times 10^8$ oocysts from $E.$ tenella were processed for iodination. In each case, sporocysts were purified from salt floated, sodium hypochlorite treated oocysts that were broken with glass beads then passed through a glass wool column. Sporocyst membranes were prepared from one-half of the sporocysts by mechanical breakage in 1 ml 10 mM sodium phosphate, 0.15M NaCl, pH 7.2 (PBS) with glass beads in the presence of protease inhibitors: 0.1 mM Phenylmethlysulfonyl fluoride (PMSF), 0.1 mM N-tosyl-L-phenylalanine chloromethyl ketone (TPCK), 1 mM N-alpha-p-tosyl-L-lysine chloromethyl ketone (TLCK) and 10 KIU/ml aprotinin. The remaining sporocysts were treated with trypsin and taurodeoxycholic acid (total volume=1 ml) to excyst sporozoites. Both preparations were pelleted at 45,000 RPM for 45 minutes at 4° C. and resuspended in 1 ml of phosphate buffered saline (PBS). Care was taken to remove all trypsin - deoxycholate residue from the sporozoites by washing with PBS and 1 mM PMSF prior to ultra-centifugation.

The one ml samples were put into glass scintillation vials which had been coated with 40 micrograms of IODOGEN (1,3,4,6-tetrachloro-3-alpha,6-alpha-diphenylglycouril) solid phase iodination reagent (24, 53), dried under nitrogen gas and rinsed with PBS. To each tube, 0.5 mCi of $^{125}$I was added and the samples allowed to incubate for 20 minutes on ice. Afterward, 100 microliters of KI (1M) was added to each tube to a final concentration of 100 mM, and the reaction was allowed to proceed for an additional 15 minutes on ice.

Sporozoite and sporocyst preparations were then diluted to 7 ml with PBS containing 5 mM KI and pelleted at 45,000 RPM for 45 minutes at 4° C.

Extraction of Sporocyst and Sporozoite Membrane Proteins. $^{125}$I labeled sporocyst and sporozoite pellets from the above high speed centrifugation were resuspended in 1 ml of protein extraction buffer (20 mM Tris-HCl, pH 7.5; 50 mM $MgCl_2$; 25 mM NaCl, 1% NP40, 1 mM PMSF, 0.1 mM TPCK, 1 mM TLCK and 10 KIU/ml aprotinin). The suspensions were incubated for 60 minutes on ice with occasional vortexing. Insoluble material was separated from the detergent solubilized protein in a microfuge for 15 minutes at 4° C. The supernatants were stored at −70° C.

TCA Precipitation of $^{125}$I Proteins. Ten microliters of each sample were diluted into 90 microliters of 5 mM KI. Ten microliters of each diluted sample was then added to a solution containing 1 ml of 5% trichloroacetic acid (TCA), 25 microliters BSA (10 mg/ml) and 5 mM KI and incubated on ice for 30 minutes. The precipitated samples were collected by filtration through glass fiber filters, washed twice with 5 ml of 5% TCA, 5 mM KI and three times with 5 ml of 95% ethanol, both at 0° C., and counted in a liquid scintillation counter.

Immunoprecipitation With Monoclonal Antibodies: Fifty microliters of monoclonal antibody were added to 25 microliters of monoclonal antibody dilution buffer (MAB-DIL): 50 mM Tris-HCl, pH 8.6; 150 mM NaCl; 0.1% NP-40; 0.1% BSA, RIA grade; 1 mM TLCK; 1 mM PMSF; 10 KIU/ml aprotinin. Twenty microliters of $^{125}$I labeled protein was then added and the tube vortexed and incubated overnight at 4° C. Rabbit anti-mouse Ig serum (IgA, IgG, IgM) was diluted 1:2 in MAB-DIL and 10 microliters added to each immunoprecipitation tube and incubated 1 hour at 4° C. Protein A-Sepharose (10% v/v) was diluted 1:4 in monoclonal antibody wash buffer, (MABW): 50 mM Tris-HCl, pH 8.3; 0.05% NP-40; 0.05% Triton X-100; 150 mM NaCl; 0.02% $NaN_3$; 5 mM KI and 400 microliters added to each tube. The tubes were incubated for one hour at 4° C. with gentle rocking. The immunoprecipitation products were washed twice with cold MABW followed by two room temperature washes with MABW. The pellet was resuspended in 50 microliters of SDS-PAGE sample buffer (35), boiled for 5 minutes and microfuged to remove the protein A-Sepharose. Supernatants were counted and analyzed by SDS-PAGE.

Electrophoretic Transfer of Antigens to Nitrocellulose Paper: Uniodinated sporozoite membrane proteins (detergent solubilized as already described) were separated under either reducing or nonreducing conditions by one dimensional sodium dodecyl sulfate polyacrylamide slab gels and electrophoretically transferred to nitrocellulose paper (75). Electrophoretic blots were processed according to the method of Sharma et al (64) with the exceptions that sera, monoclonal antibodies and the appropriate conjugates (peroxidase conjugated goat anti-chicken IgG, Kirkegaard and Perry, peroxidase conjugated rabbit anti-mouse IgG (Cappel) were employed for blots of reducing gels, and murine monoclonal antibodies used in conjunction with the Vectastain ABC kit for mouse IgG for nonreducing gels (Vector Labs, Burlington, Calif). Blots were developed by reacting them with 4-chloro-1-napthol (Sigma; 660 micrograms/ml) and $H_2O_2$ (0 17%) for reduced separation or Vectastain reagents for nonreducing separations.

SDS - Polyacrylamide Gel Electrophoresis (SDS-PAGE) of $E.$ $tenella$ Proteins. Total $^{125}$I labeled sporocyst and sporozoite membrane proteins immunosorbed, and immunoprecipitated proteins were analyzed on, 5–25% exponential or 8–20% linear gradients SDS-polyacrylamide gels at 25 mA. The gels were dried and exposed to Kodak XAR-5 X-ray film overnight at −70° C. Gels used for staining purposes were visualized by Coomassie (21) or silver staining using the manufacturer's labelled instructions (Pierce Chemical).

Results of Immunoprecipitation of $E.$ $tenella$ Antigen with Ptn 7.2A4/4 Monoclonal Antibody. The surface-labeled $E.$ $tenella$ sporozoite preparation contains two heavily iodinated proteins with apparent molecular weights of 6,500 and 25,000 as judged on reducing SDS-PAGE. The 6,500 dalton protein is readily and specifically immunoprecipitated with monoclonal antibody Ptn 7.2A4/4. Membranes from sporocysts contain two heavily iodinated proteins with apparent molecular weights of 17,000 and 27,000 although several other minor iodinated proteins of various molecular weights are also present. Upon immunoprecipitation of $^{125}$I labeled sporocyst membrane protein the only antigen precipitated following the reaction with the monoclonal antibody Ptn 7.2A4/4 was the 17,000 dalton protein as determined on reducing SDS-PAGE.

Results of Western Blots of $E.$ $tenella$ Antigens with Ptn 7.2A4/4 Monoclonal Antibody. Under the conditions in which the immunoprecipitated, iodinated polypeptides were analyzed on SDS-PAGE as described above, polypeptides linked by disulfide bonds have been separated. However, reduction of disulfide bonds destroys Ptn 7.2A4/4 reactivity on Western blots in both sporocyst and sporozoite membrane preparations. When iodinated sporocyst and sporozoite membrane preparations were run on SDS-PAGE under non-reducing conditions the major radiolabeled species migrates with an apparent molecular weight of 23–25,000. Furthermore, this apparent 23–25,000 dalton species was reactive with monoclonal antibody Ptn 7.2A4/4 by Western blotting. These results suggest that the 17,000 dalton polypeptide and the 8,000 dalton polypeptide are complexed together to form the TA4 antigen. The fact that this other polypeptide component of the TA4 antigen was not observed in immunoprecipitation experiments of iodinated material can be explained by the observation that this other polypeptide does not contain any tyrosines that could be iodinated (see description of the 8,000 dalton polypeptide component of the TA4 antigen in Examples 5 and 6).

EXAMPLE 4

Purification, Identification and Characterization of the $E.$ $Tenella$ TA4 Antigen and Fragments Containing Fractions Thereof Purification of the 17,000 Dalton Peptide Component of the TA4 Antigen. $E.$ $tenella$ sporulated oocysts were resuspended in 10 ml PBS per $10^9$ oocysts and were broken by shaking with an equal volume of glass beads. Membranes were isolated by centrifugation (100,000×g, 60 min., 4° C.) and the proteins were solubilized in 1% (v/v) NP-40, 10 mM Tris-HCl (pH 7.5), 25 mM NaCl, 1 mM PMSF, 1 mM TLCK, 0.1 mM TPCK and 10 KIU/ml aprotinin. Insoluble material was pelleted with another 100,000×g spin (60 min., 4° C.). The protein was adsorbed to a DEAE-cellulose column equilibrated with 10 mM Tris-HCl (pH 7.7), 0.05% NP-40 and then washed with this buffer containing 50 mM NaCl. After elution with buffer containing 200 mM NaCl, the 17,000 dalton polypeptide was concentrated by acetone precipitation and the precipitate resuspended in loading buffer, boiled and subjected to electrophoresis in SDS-polyacrylamide (15%). Conventional SDS-PAGE sample buffer used in this and other experiments contained 62.5 mM Tris-HCl (pH 6.8), 2% (w/v) sodium dodecyl sulfate, 10% (w/v) glycerol and 0.001% (w/v) bromphenol blue. The buffer also contained 5% (v/v) beta-mercaptoethanol except in experiments in which non-reducing conditions are specified. The 17,000 dalton polypeptide band was identified by staining (Coomassie blue or KCl). The appropriate gel region was excised, the protein electro-eluted and concentrated by acetone precipitation. Note that these procedures are denaturing for proteins and peptides bound to each other by disulfide bonds are separated with this method. The 17,000 dalton polypeptide purified by this method was essentially pure.

Purification and Characterization of the TA4 Antigen. As an alternative to purification by gel electrophoresis the sporocyst membrane proteins from the DEAE-cellulose column were dialyzed against 10 mM Tris-HCl, pH8, 0.05% NP-40 and applied to a DEAE-HPLC column (Bio-Rad) equilibrated in this buffer. The column was eluted with a NaCl gradient (0–300 mM) in the same buffer. The 17,000 dalton polypeptide (identified by its migration on gel electrophoresis) was found in material eluting at 200 mM NaCl. Fractions containing this protein were applied to a hydroxyapatite column (HPHT-Bio-Rad) equilibrated with 30 mM potassium phosphate, pH 6.5, 0.05% Zwittergent 3-12 (Calbiochem-Behring, LaJolla, Calif.), 0.1 mM dithiothreitol. The column was washed with equilibration buffer and developed with a potassium phosphate gradient (0–300 mM) containing 0.05% Zwittergent and 0.1 mM dithiothreitol. The 7,000 dalton polypeptide (identified by gel electrophoresis described above) appeared in material eluting at approximately 90 mM potassium phosphate.

Fractions containing the 17,000 dalton polypeptide purified by this method also contained a second peptide of 8,000 daltons. This peptide appears to be linked by a disulfide bridge to the 17,000 dalton polypeptide. If the fractions containing the 17,000 dalton peptide were immunoprecipitated with monoclonal antibody Ptn 7.2A4/4 and the precipitated proteins analyzed by gel electrophoresis under reducing conditions (as above) both the 17,000 and 8,000 dalton polypeptides appear to be immunoprecipitated. Hence, in sporocyst membrane preparations, the 8,000 dalton and 17,000 dalton polypeptides appear to be linked by a disulfide bond (presumably by a cysteine bridge) because the two peptides did not appear on electrophoresis unless a strong reducing agent was present. Under nonreducing conditions, the Ptn 7.2A4/4 reactive species migrates with an apparent molecular weight of 21-24,000.

Preparation of the 11,500 dalton fragment of the TA4 antigen. E. tenella sporocyst membranes were prepared as described above and resuspended in 10 ml of PBS+1% Triton X-100. To this 10 ml membrane suspension was added 10 ml of 80% phenol containing 0.1% 8-hydroxyquinoline. The suspension was then vortexed at maximum at 4000 RPM. The phenol and the flocculent interface were removed and diluted in five volumes of 100 mM ammonium acetate in methanol and allowed to precipitate at −20° C. overnight. Following two washes in acetone, the insoluble proteins were agitated for 8 hours in 0.5% SDS, and insoluble materials removed by centrifugation at 20,000 RPM for one hour at 4° C. The sample was dialyzed extensively against PBS (pH 7.2) containing AG 501-X8 mixed bed resin (1 gm/500 ml). The 11,500 dalton fragment of the TA4 antigen was then immunoadsorbed from the supernatant using the Ptn 7.2A4/4 monoclonal antibody as follows. This polypeptide was shown to be reactive with the Ptn 7.2A4/4 monoclonal antibody by microtiter plate ELISA.

For microtiter plate ELISA polystyrene 96 well clusters (Immulon II) were sensitized with antigen in 10 mM glycine buffered saline, pH 9.6, incubated overnight at 37° C. The wells were washed with 0.15M PBS with 0.0005% Tween-20, blocked with 3% BSA in PBS Tween, rewashed, and incubated with Ptn 7.2A4/4 monoclonal antibody diluted in PBS. The wells were washed as before, and then incubated with peroxidase conjugated rabbit anti-mouse IgG serum diluted in PBS. The wells were washed again and then incubated with substrate (2,2′-azino-di-[3-ethyl-benz-thiazoline sulfonate]) in the presence of $H_2O_2$. Color development was determined with a Dynatech MR-580 microtiter plate ELISA reader after 15 minutes. The 11,500 dalton fragment of the TA4 antigen was shown to be reactive with the Ptn 7.2A4/4 monoclonal antibody by microtiter plate ELISA.

EXAMPLE 5

Amino Acid Sequence of the 17,000 and 8,000 Dalton Peptide Components of the E. Tenella TA4 Antigen Amino Acid Sequence of the 17,000 Dalton Peptide Component of the TA4 Antigen. Amino acid sequencing of the 17,000 dalton peptide was complicated by the finding that the N-terminal amino acid was blocked (i.e. not accessible to Edman degradation (14)). To circumvent this problem the protein was reduced and alkylated and then digested with various chemicals and enzymes. The resulting peptides were purified by reverse phase HPLC (26). The 17,000 dalton polypeptide or the TA4 antigen was digested with CNBr (CN), V8 protease (V), chymotrypsin (CH) and Endoprotease Arg-C (R).

Before protease digestion the purified 18,000 dalton polypeptide or the TA4 antigen was treated with 30 mM dithiothreitol, 6M guanidine-HCl (pH 8) for 1 hour at room temperature. Solid iodoacetamide was added to a final concentration of 100 mM, the pH was readjusted to 8 and the sample was incubated for 1 hour at room temperature. Following reduction and alkylation, samples were purified from reagents either by P6DG (Bio-Rad, Richmond, Calif.) spin columns equilibrated in 0.1M MOPS, pH 7.5, 0.1% SDS or by reverse phase HPLC.

For CNBr digestion, the protein sample was treated with 1% CNBr in 70% formic acid for 20 hours at 4° C. The sample was evaporated to dryness in a Savant Speedvac centrifuge and redissolved in 0.1% trifluoroacetic acid (TFA) or 0.1% TFA, 20% acetonitrile ($CH_3CN$). V8 digestion was performed in 0.1% SDS, 0.1M MOPS pH 7.5 for 2 hours at room temperature at a ratio of 50 micrograms 17,000 dalton polypeptide: 1 microgram V8. After digestion, the samples were precipitated with 4 volumes of acetone at −20° C. overnight. The acetone precipitates were redissolved as described above. Chymotrypsin digestion was performed in 0.05% Zwittergent 3-12, 0.1M $NH_4HCO_3$, pH 7.8 for 1 hour at 37° C. at a ratio of 50:1, 17,000 dalton peptide:chymotrypsin. Samples were acidified with TFA for peptide purification. Arg-C digestion was performed in 0.05% Zwittergent 3-12, 0.1M NH pH 7.8 for 2 hours at 37° C. at a ratio of 15:1, 17,000 dalton peptide: Arg-C. After acetone precipitation overnight at −20° C., the peptides were mainly in the acetone supernatant. The supernatant was evaporated and the samples redissolved as described above. Peptides were purified on a Vydac C4 column (the Separations Groups, Inc., Hesperia, Calif.) and eluted with a 0-100% CH CN gradient in 0.1% TFA.

Amino acid sequencing was performed using a gas phase sequencer (Applied Biosystems, Inc., Foster City, Calif.) according to the procedure of Hunkapiller et al (25). Phenylthiohydantoin (PTH) derivatized amino acids were analyzed by HPLC (8).

The N-terminal amino acid was determined directly by removing the blocking agent. The 17,000 dalton peptide was treated with pyroglutamate aminopeptidase (5:1 protein:PAP) in 0.1M potassium phosphate (pH 8.0), 10 mM EDTA, 5% glycerol, 5 mM dithiothreitol, 0.05% Zwittergent ® 3-12 for 1 hour at 37° C. After treatment, the amino acid sequence could be determined directly suggesting that the N-terminal amino acid glutamine is cyclized to form the blocked residue pyrrolidone carboxylic acid. The complete amino acid sequence for the 17,000 dalton peptide component of the TA4 antigen is shown in FIG. 1.

Partial Amino Acid Sequence of the 8,000 Dalton Peptide Component of the TA4 Antigen. When the purified 8,000 dalton peptide (derived from the TA4 antigen by reduction and alkylation) was subjected to Edman sequencing the N-terminal amino acid sequence could be determined directly. A partial amino acid sequence of the N-terminal region of the peptide is shown below.

$NH_2$—ala ala gly thr thr asp ala val ile cys
leu thr asn pro ala pro leu glu ala
arg ser gln pro phe asp asp glu

EXAMPLE 6

Isolation and Characterization of a Genomic DNA Clone Encoding the *Eimeria Tenella* TA4 Antigen Isolation of DNA from *E. tenella* Sporulated Oocysts. Sporulated oocysts ($5 \times 10^8$) were washed and sporocysts were isolated as described previously. Isolated sporocysts were washed 2× with 0.1M Tris-HCL, (pH 8.5), 0.2M NaCl, 10 mM EDTA. Sporocysts were lysed by incubation for 30 min. at 65° C. in 0.1M Tris-HCl, (pH 8.5), 0.2M NaCl, 50 mM EDTA, 1% SDS, 150 micrograms/ml Proteinase K. After cooling to room temperature the DNA was gently extracted with an equal volume of liquified phenol for 1 hour. After centrifugation for 10 min. at 3,000 rpm, the aqueous layer was removed and the interface and phenol were re-extracted with 10 mM Tris-HCl (pH 8), 1 mM EDTA. The aqueous phases were pooled and extracted 1× with phenol and 2× with chloroform:isoamyl alcohol (24:1). DNA was isolated by ethanol precipitation. The DNA pellet was redissolved in 10 mM Tris-HCl (pH 8), 1 mM EDTA and treated with 0.15 mg/ml DNase free-RNase A for 1 hour at 37° C. After RNase digestion, the sample was extracted 1× with phenol, 1× with chloroform: isoamyl alcohol and then precipitated with ethanol. On agarose gels, the size of the DNA was determined to be greater than 20 kilobase pairs.

Construction of the *E. tenella* Genomic Library in Bacteriophage λgt wes λB. The *E. tenella* genomic DNA library in bacteriophage λgt wes λB (36) was constructed using methods described by Maniatis et al. (44). Phage were purified by polyethyleneglycol precipitation, chloroform extraction and CsCl gradient centrifugation. Purified phage were disrupted with 1% SDS, 50 mM EDTA and 150 micrograms/ml Proteinase K, and DNA was purified by phenol extraction, chloroform extraction and ethanol precipitation. The *E. tenella* genomic DNA and phage DNA were digested to completion with EcoRI. The left and right arms of the phage DNA were annealed at their cohesive ends and the arms were purified by sucrose density gradient centrifugation. 30 micrograms of EcoRI digested DNA arms were ligated to 6 micrograms of EcoRI digested *E. tenella* DNA using T4 DNA ligase. 20 micrograms of the ligated DNA were packaged in vitro into phage particles producing a library of $5 \times 10^6$ recombinant phage particles.

Synthetic Oligonucleotides. Oligonucleotide probes complementary to regions of the gene encoding the 7,000 dalton peptide component of the TA4 antigen were synthesized using a Biosearch Sam I (Biosearch, Inc., San Rafael, Calif.). The expected DNA sequences of the appropriate regions were deduced from the amino acid sequence of the 17,000 dalton peptide. Because of the ambiguity in the genetic code, the exact DNA sequence cannot be predicted. "Mixed probes" were designed and synthesized which contained a mixture of DNA sequences, one of which should have perfect match homology with the gene for the 17,000 dalton peptide.

Oligonucleotide COD 92 was based on amino acids 6 to 12 of peptide V1 (see Example 5 for amino acid sequence of the 17,000 dalton peptide). It contained a mixture of 256 different sequences. The structure of oligonucleotide COD 92 is:

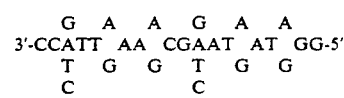

Amino Acid Sequence: Gly Asn Phe Ala Tyr Tyr Pro

Oligonucleotide COD 94 was based on amino acids 3 to 8 of peptide V2 of the 17,000 dalton peptide. It contained a mixture of 64 different sequences:

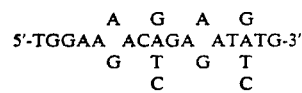

Amino Acid Sequence: Trp Lys Thr Glu Ile Cys

Oligonucleotide COD 108 was based on amino acids 25-30 of peptide V1. It contained a mixture of 16 different sequences. The structure of oligonucleotide COD-108 is:

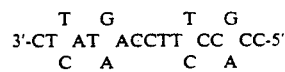

-continued
Amino Acid Sequence: Glu Tyr Trp Lys Gly Gly

Screening the *E. tenella* Genomic DNA Library. Recombinant phage of the *E. tenella* genomic DNA library were plated on 15 cm plates at high density, up to 2-3×10⁴ phage per plate. Nitrocellulose filter replicas of each plate were prepared according to the method of Benton and Davis (3). The filters were then incubated with the appropriate synthetic oligonucleotides which had been labeled to high specific activity with (³²P)-dATP and T4 polynucleotide kinase. Positive plaques were identified by autoradiography. Only those plaques that hybridized to both oligonucleotides COD-92 and 108 were scored positive.

Small blocks of agar were cut from the plates in regions that corresponded to the region of the filter containing the hybridizing DNA. The phage were eluted, replated at lower density (20-100/plate) and rescreened with all three oligonucleotide probes. Pure isolated positive plaques or clones were picked. Phage 108-1 hybridized strongly to oligonucleotide COD-92 and moderately to oligonucleotides COD-108 and 94. Phage 108-1 was grown up on a larger scale for purification and characterization of the *E. tenella* DNA insert. Characterization of phage 108-1 DNA showed an EcoRI insert of 5,500 bp.

Figure 2:
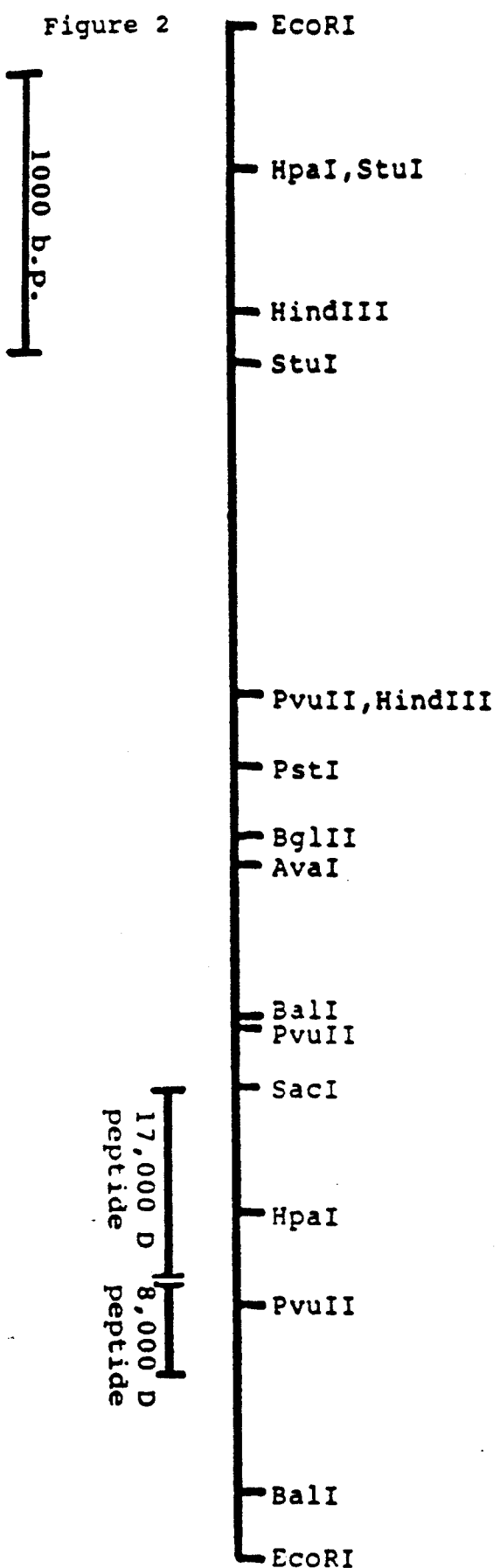
FIG. 2 shows the restriction enzyme map of the E. tenella genomic clone 108-1 encoding the TA4 antigen.

Detailed Characterization of the Genomic Clone Encoding the 17,000 Dalton Peptide—Restriction Map. The 5,500 bp EcoRI fragment insert of clone 108-1 was subcloned from the phage vector into plasmid pUC 9 (78). The recombinant plasmids were digested with a variety of restriction endonucleases to determine the position of key restriction sites in the genomic DNA clone. The position of restriction sites within the DNA was needed to determine the location and orientation of the 17,000 dalton peptide gene and to develop a strategy to sequence the EcoRI genomic DNA fragment. The restriction map is presented in FIG. 2. The location and orientation of the gene for the 17,000 dalton peptide is shown on this map.

DNA Sequence Analysis of Clone 108-1. The BglII-EcoRI fragment of clone 108-1 containing the gene for the 17,000 dalton peptide component of the TA4 antigen was sequenced by the dideoxy method of Sanger (62) using various restriction enzyme fragments. Primers for DNA synthesis included oligonucleotides COD-92, 94 and 108 as well as other synthetic oligonucleotides. The DNA sequence is shown in FIG. 5.

Structure of the Gene Encoding the TA4 Antigen. The DNA sequence agrees with that predicted by the amino acid sequence analysis. In addition, there are three features of the gene which are not apparent from the protein sequence. Using protein sequence information and general information regarding the structure of secretory proteins, the structure of the gene for the TA4 antigen has been deduced.

From the known amino terminus of the sporocyst membrane 17,000 dalton peptide (see Example 5), Gln-Asp-Tyr---, it is apparent that the gene encodes an extra 23 amino acids upstream. This DNA sequence is a typical "signal" sequence found at the amino terminus of genes for many secretory or membrane proteins (4, 34). The peptide it encodes is required for the export of protein from their site of synthesis (the cytoplasm) to and/or through the plasma membrane. The signal peptide is usually removed during the secretory process. It is not surprising that the TA4 antigen is made with a signal peptide since it most likely traverses the cytoplasmic membrane in order to be found at the outer surface of the sporozoite. The amino terminus of the signal sequence is assumed to be the Met codon since, essentially, synthesis of all proteins begin with methionine.

There are three regions of the gene in which the DNA sequences do not coincide with the protein sequence. The first is a 101 bp segment occurring within the codon for Val-7 of the known mature 17,000 dalton protein sequence. The second is a 114 bp sequence between the codons for Gly-65 and Gly-66 of the 17,000 dalton peptide. The third is a 124 bp sequence within the codon for Asp-186 of the 8,000 dalton peptide. These three sequences are intron structures typically found within the coding regions of many eukaryotic genes. They are present in the precursor to the mRNA, and then removed by an RNA recombination mechanism known as "splicing," to give the mature mRNA an uninterrupted coding sequence. The DNA sequences around the "splice junctions" are consistent with those seen in other eukaryotic genes (65).

The sequence of the 17,000 dalton peptide appears to terminate with the sequence Gly-Gly corresponding to codons 157 and 158. We have also identified an 8,000 dalton peptide with the sequence beginning with Ala-162 extending to Glu-188. The peptide sequence Arg-Arg-Leu corresponding to codons 159 through 161 has not been found. It is probable that this tripeptide is removed by a mechanism similar to the cleavage of other proteins such as insulin (71). Hence the two peptides of the TA4 antigen are encoded by a contiguous nucleotide sequence, and at least one proteolytic step occurs to generate the 8,000 dalton peptide beginning with Ala-162.

EXAMPLE 7

Appearance of the TA4 Antigen During Sporulation

In order to determine when in the process of sporulation the TA4 antigen occurs, its appearance was measured by immunoreaction with a specific monoclonal antibody, Ptn 9.9 D12. Monoclonal antibody Ptn 9.9 D12 is a sporozoite-neutralizing monoclonal antibody that reacts with the TA4 antigen. Reducing conditions destroy the reactivity of the TA4 antigen with monoclonal antibody Ptn 7.2 A4/4. However, on Western blots of SDS PAGE under reducing conditions monoclonal antibody Ptn 9.9 D12 reacts with the 17,000 dalton polypeptide component of the TA4 antigen.

Starting immediately after the final PBS wash (see Example 1) aliquots containing 1×10⁷ oocysts were removed for analysis at four hour intervals up to 24 hours and at 36 to 48 hours after sporulation was begun. Sporulating oocysts were centrifuged at 7-800×g for 10 minutes and the supernatant was removed. The pellets were quick-frozen in a dry ice/methanol bath and then stored at −70° C. until analysis.

Each pellet was thawed in 200 microliters of 20 mM Tris-HCl pH 7.5, 50 mM MgCl₂, 25 mM NaCl and an equal volume of glass beads. After shaking vigorously for 10 minutes 200 microliters of 2 x SDS PAGE sample buffer (35) was added. Samples were boiled for 3 minutes, centrifuged to remove debris and 25-50 microliters of each sample was applied to SDS polyacrylamide gels (5-25% gradient) for analysis. Proteins were transferred to nitrocellulose sheets (5, 75). The remaining protein binding sites on the nitrocellulose were blocked with 3% (w/v) gelatin, 10 mM Tris-HCl pH 7.5, 150 mM NaCl, 0.05% (w/v) NaN₃ for 30 minutes at room temperature. Nitrocellulose filters were incubated with monoclonal antibody Ptn 9.9 D12 (approximately 10 micrograms/ml in 3% (w/v) bovine serum albumin, 10 mM Tris-HCl pH 7.5, 150 mM NaCl, 0.05% (w/v) NaN₃) overnight at 4° C. After washing the nitrocellulose filters three times with 50-100 ml of the antibody dilution buffer, the location and amount of bound monoclonal antibody Ptn 9.9 D12 was determined using the Vectastain ABC Kit for mouse IgG (Vector Laboratories, Inc., Burlingame, Calif.). Nitrocellulose filters were immersed in 20 ml of biotinylated horse anti-mouse IgG (80 microliters biotinylated anti-mouse antibody, 80 microliters normal horse serum in 20 ml antibody dilution buffer) and gently shaken for 30 minutes at room temperature. Nitrocellulose filters were rinsed three times with 50-100 ml of antibody dilution buffer without NaN₃ Nitrocellulose filters were then incubated with 15 ml of Vectastain ABC Reagent for 30 minutes at room temperature (80 microliters Avidin DH Reagent A mixed with 80 microliters biotinylated horseradish peroxidase Reagent B in 15 ml antibody dilution buffer without NaN₃ preincubated for 30 minutes before addition to the filters). After three washes bound horseradish peroxidase was measured by color development with 4-chloro-1-napthol (Sigma Chemical Co., St. Louis, Mo.). Blots were incubated with the color development solution (2 ml of 3 mg 4-chloro-1-napthol/ml methanol, 5 microliters 30% hydrogen peroxide in 10 ml 10mM Tris-HCl pH 7.5, 150 mM NaCl) for 10-30 minutes. After appearance of the purple bands indicating the location and amount of Ptn 9.9 D12 reactive material, the nitrocellulose sheets were washed twice with water, air dried and stored in the dark.

Figure 4:
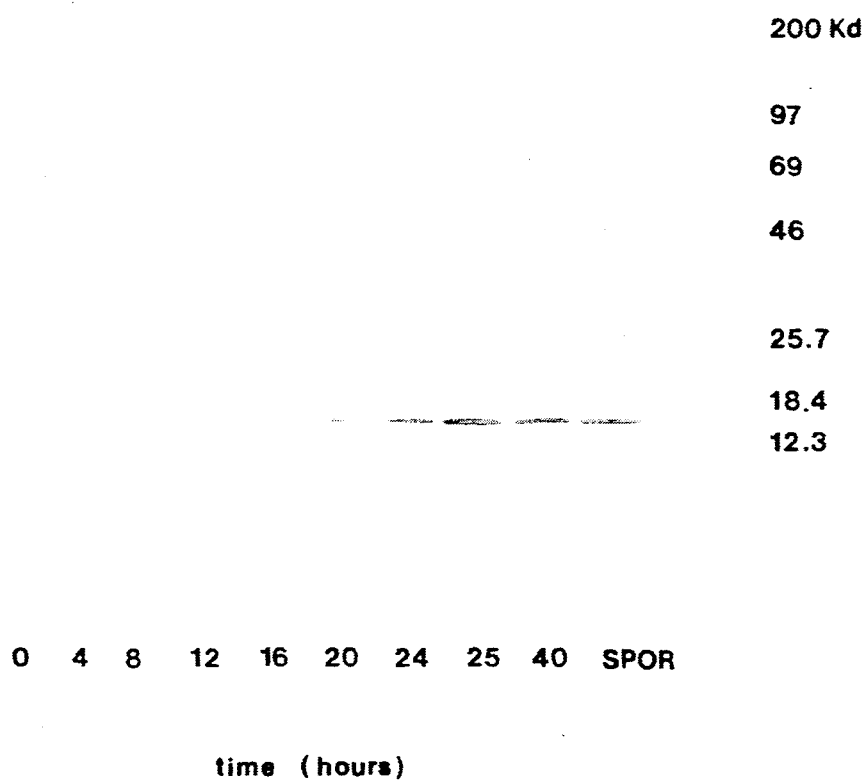
FIG. 4 shows the appearance of the TA4 antigen during sporulation as determined by the appearance of a 17,000 dalton subunit immunoreactive with monoclonal antibody Ptn 9.9 D12.

The 17,000 dalton polypeptide component of the TA4 antigen that was immunoreactive with monoclonal antibody Ptn 9.9 D12 appeared between 16 to 24 hours after the initiation of sporulation and thereafter (FIG. 4). Sixteen hours corresponds with the beginning of elongation of the four structures destined to become sporocysts inside the sporulating oocyst.

EXAMPLE 8

Isolation and Identification of mRNA Encoding the TA4 Antigen

Before cDNA, could be synthesized it was necessary to determine when the mRNA encoding the TA4 antigen appeared during sporulation. Aliquots containing $2.5-5 \times 10^8$ oocysts were asceptically removed at four hour intervals up to 24 hours (including time 0) and at 36 to 48 hours after sporulation was begun. The sporulating oocysts were centrifuged at 7-800×g for 10 minutes and the supernatant was removed. The pellets were quick-frozen in a dry ice/methanol bath and then stored at −70° C. until RNA was isolated.

Each pellet was thawed in approximately 10 volumes of 5M guanidine thiocyanate, 20 mM Tris-HCl pH 7.5, 10 mM EDTA, 5% (v/v) beta-mercaptoethanol and oocysts were rapidly broken by shaking vigorously with an equal volume of 1.0 mm glass beads for 10 minutes. After bringing the samples to 2% (w/v) N-lauroylsarcosine they were centrifuged at approximately 8,000×g at room temperature to remove debris. RNA was isolated from the supernatant by sedimentation through a CsCl cushion (76).

The RNA pellet was resuspended in 20 mM Tris-HCl pH 7.5, 50 mM EDTA pH 8.0, 0.2% SDS, 100 units/ml RNasin ™ (Promega Biotec, Madison, Wisc.), 10 mM beta-mercaptoethanol. After extracting twice alternately with phenol:chloroform:isoamyl alcohol (24:1) and chloroform:isoamyl alcohol (24:1) the RNA was precipitated and stored in ethanol at −20° C. Approximately 100–300 micrograms of total RNA was isolated from $2.5-5.5 \times 10^8$ oocysts.

PolyA-containing RNA was isolated by oligo-dT cellulose chromatography (2). Total RNA was loaded on an oligo-dT cellulose column (Type 3, Collaborative Research, Inc., Lexington, Mass.) in 10 mM Tris-HCl pH 7.5, 1 mM EDTA, 0.2% (w/v) SDS, 0.4M LiCl. RNA was eluted at 40° C. in the same buffer without LiCl. Approximately 5-15 micrograms A⁺ RNA was isolated from $2.5-5.0 \times 10^8$ oocysts.

Figure 6:
FIG. 6 shows the occurrence of the TA4 antigen mRNA during sporulation, as determined by hybridization of an internal restriction fragment from a genomic clone of the TA4 gene.

Before polyA RNA could be used as a template for cDNA synthesis, it was necessary to demonstrate the presence of the mRNA encoding the TA4 antigen. The presence of the TA4 antigen mRNA was demonstrated by hybridizing polyA RNA from oocysts at various stages of sporulation with DNA from the clone encoding the TA4 protein. Two micrograms of polyA RNA from each time point during sporulation was electrophoresed through gels containing formaldehyde (44). The RNA was transferred to nitrocellulose filters for Northern blot analysis. Nitrocellulose filters were probed with the 785 bp SacI-PvuII fragment of the E. tenella genomic clone 108-1 (FIG. 5) which had been nick translated with [$^{32}$P]-dATP (44). The mRNA encoding the TA4 antigen was present approximately 16-20 hours after sporulation was initiated and thereafter (FIG. 6). The time of appearance of the mRNA for the TA4 antigen correlates exactly with the appearance of the 17,000 dalton subunit of the TA4 antigen that is immunoreactive with monoclonal antibody Ptn 9.9 D12 on Western blots. These experiments demonstrate that mRNA from sporulated oocysts could be used to make cDNA encoding the TA4 antigen.

EXAMPLE 9

Isolation and Characterization of a cDNA Clone Encoding the TA4 Antigen cDNA

The nucleotide sequence encoding the TA4 antigen was to be used as a gene in an easily grown cell such as E. coli to produce a TA4 protein for vaccination of chickens against coccidiosis caused by certain Eimeria. There are three regions of the TA4 gene (FIG. 5) in which the DNA sequence does not coincide with the protein sequence. These three sequences are introns typically found within the coding regions of many eukaryotic genes. However, since genes containing introns would not express the proper protein in E. coli it was necessary to isolate a cDNA clone encoding the TA4 antigen. This clone contains a continuous coding sequence for the TA4 antigen.

Synthesis of cDNA

Briefly, the sporulated oocyst mRNA isolated as described in Example 8 was transcribed into cDNA by the action of AMV reverse transcriptase as described by Ullrich et al. (76). Transcription was initiated at the 3'-polyadenylated end of the TA4 antigen mRNA using oligo-dT as a primer. The second DNA strand was copied using DNA Polymerase I (the Klenow fragment). From 2 micrograms of mRNA we obtained 340 ng cDNA.

Specifically, 2 micrograms of oligo-dT (12-18 nucleotides, Pharmacia Molecular Biology Division, Piscataway, N.J.) was annealed to 2 micrograms of purified mRNA in the presence of 50 mM NaCl. The annealing reaction was heated to 90° C. and then slowly cooled. For the reverse transcriptase reaction, deoxynucleosidetriphosphates (A, T, G, C) were added to 0.5 mM along with 40 units of enzyme (Molecular Genetic Resources, Tampa, Fla.). The reverse transcriptase reaction buffer was as follows: 15 mM Tris-HCl, pH 8.3, 21 mM KCl, 8 mM MgCl$_2$, 0.1 mM EDTA, and 30 mM beta-mercaptoethanol. This mixture was incubated at 42° C. for 45 minutes. The RNA-DNA duplex was extracted once with phenol chloroform and then precipitated with ethanol. The pelleted material was then resuspended in 100 microliter reaction mixture containing the following: 20 mM Tris-HCl pH 7.5, 5 mM MgCl$_2$, 100 mM KCl and 250 mM each dATP, dCTP, dTTP, dGTP.

RNAse H (100 units/ml Pharmacia Molecular Biology Division, Piscataway, N.J.) and DNA Polymerase I—Klenow fragment (50 units/ml Boehringer Mannheim, Indianapolis, Ind.) were added and the reaction was incubated at 12° C. for 60 minutes. The combined activities of these enzymes result in the displacement of the mRNA from the RNA-DNA duplex as the first cDNA strand is used as a template for synthesis of the second cDNA strand. The reaction was stopped by the addition of EDTA to a final concentration of 10 mM and the DNA duplex was then extracted with phenol:chloroform and ethanol precipitated. The sequence of the reactions of DNA Polymerase I and RNAse H was predicted to yield cDNA molecules which were blunt ended at both their 3' and 5' ends. A 3' blunt end was necessary for the subsequent cloning of the cDNA.

Construction of the TA4 cDNA Library

The cDNA was resuspended in 100 microliters of sterile water. To clone the cDNA into a library a restriction site was used that had been determined from the genomic clone 108-1 DNA sequence. A SacI site is immediately upstream to the N-terminal glutamine of the mature 17,000 dalton subunit of the TA4 antigen. Approximately 50 ng was digested with SacI (50 units/ml) in the presence of 6 mM Tris-HCl (pH 7.4) 6 mM MgCl$_2$, and 6 mM beta-mercaptoethanol for 60 minutes at 37° C.

The sample was then re-extracted with phenol:chloroform and ethanol precipitated. For the cloning step a pUC18 vector (56) was used. The vector had been digested with SacI and SmaI. SmaI provided the blunt end site necessary for ligation of the 3' end of the cDNA. The ligation reaction was performed using 40 ng of vector DNA and 50 ng of cDNA. Ligations were done overnight at 12° C. in a ligase buffer of 50 mM Tris-HCl (pH 7.8), 10 mM MgCl$_2$, 20 mM dithiothreitol, 1.0 mM rATP using one unit of T4 DNA ligase.

The recombinant DNA molecules were then introduced into *Escherichia coli* K-12 strain MH1 by transformation. The transformed bacteria were spread on agar plates containing the antibiotic ampicillin at a concentration of 50 micrograms/ml. Since the plasmid pUC18 (56) contains the ampicillin resistance gene, only those bacteria which acquired a recombinant plasmid survived. These bacteria each grew and divided to form a bacterial colony. Each cell in the colony is a descendant of the original parental cell and contains the same recombinant plasmid. Approximately 6700 clones were obtained from the 55 nanograms of cDNA used to make recombinant plasmids.

Identification of TA4 cDNA Clones

This cDNA library was screened by colony hybridization using the high density screening method described by Grunstein and Hogness (20). The 785 bp SacI-PvuII fragment of the genomic clone was purified and labeled with $^{32}$P by nick-translation (44). Positive clones were identified, purified and plasmid DNA was isolated for further analysis. Restriction analysis of the positive cDNA clone agreed with the map of the genomic clone. The cDNA insert of the clone designated as pTCD26 was sequenced by dideoxy sequencing using oligonucleotide primers made to correspond to the genomic clone (62). The sequence of the cDNA pTCD26 clone is shown in FIG. 7. This cDNA clone was transformed into an *E. coli* strain JM83, and the strain designated as JM83/pTCD26 was deposited with the American Type Culture Collection, Rockville, Md., and assigned ATCC accession No. 53315. This deposit was made pursuant to the Budapest Treaty On.

The DNA sequence agreed with that predicted from the genomic clone. The predicted amino acid sequence from the cDNA agreed with the TA4 antigen amino acid sequence obtained by protein microsequencing.

EXAMPLE 10

Expression of the cDNA Derived TA4 Antigen Gene in *E. coli*

Construction of cDNA Derived TA4 Direct Expression Plasmids

The cDNA clone provides the gene for synthesis of the TA4 protein in bacteria. However, the cDNA does not contain the proper signals to allow transcription and translation in *E. coli*. Therefore, the cloned cDNA was inserted into expression vectors that contain a strong promoter(s) for RNA polymerase and a ribosome binding site to initiate protein synthesis in *E. coli* upstream of the inserted cDNA. As used herein, the phrase TA4 protein refers to the expression product of the cDNA of FIG. 7 or any recombinant TA4-derived material produced in a bacterial host cell. The phrase TA4 antigen refers to the naturally-occurring material as expressed by the genomic TA4 DNA, as present on the surface of the sporozoite or purified away from sporozoites.

Expression vectors pWHA33 and pWHA63 were constructed so that genes could be inserted in them to obtain expression in *E. coli*. Other suitable plasmids known to one skilled in the art could also be used. Plasmids pWHA33 and pWHA63 are two examples of suitable plasmids. The pWHA33 plasmid contains three promoters (lac, lambda P$_R$ and trp) each of which could direct transcription of an inserted gene. Plasmids containing various combinations of these promoters and the tac promoter from plasmid pDR450 (61) (Pharmacia) Molecular Biology Division, Piscataway, N.J.) were constructed. The structure of plasmids pWHA33 and pWHA63 are diagrammatically shown in FIG. 8.

One strategy to synthesize the TA4 protein in *E. coli* is to simply provide a ribosomal binding site and a methionine codon (ATG) preceding the coding sequence. To construct such a direct expression plasmid for the TA4 protein, the cDNA clone pTCD26 was digested with SacI and then treated with Klenow fragment of DNA polymerase I to produce blunt ends. An oligonucleotide linker COD-154 was ligated to the blunted SacI end to provide the ATG codon to initiate protein synthesis and the BamHI site necessary to clone into the BamHI site of pWHA63. The structure of COD-154 is:

Ribosome Binding Site

CATA$\overline{\text{AGGATCC}}$TT$\underline{\text{ATG}}$ $\underline{\text{BamHI}}$    Start
site    codon The insertion of TT immediately preceding the initiation codon ATG in COD-154 is to improve efficiency of translational initiation.

After ligation of oligonucleotide COD-154 to the blunt ends of pTCD26, the product was digested with BamHI. The 1276 bp fragment containing the TA4 gene was purified on a polyacrylamide gel and then ligated into the BamHI site of expression vector pWHA63 resulting in plasmid pDET1. The construction of pDET1 is diagramatically shown in FIG. 8. Another direct expression plasmid, pDET2 was constructed from pDET1 by digestion of pDET1 with HindIII and religation which removed the HindIII fragment containing lambda $P_R$ and lambda cI. The pDET1 and pDET2 direct expression vectors were transformed into E. coli strain REN3.

The recombinant DNAs and host microorganisms described herein as REN3/pDET1 and REN3/pDET2 were deposited with the American Type Culture Collection, Rockville, Md. and assigned ATCC Accession Numbers 53316 and 53318, respectively. These deposits were made pursuant to the Budapest Treaty.

Synthesis and Analysis of Cloned Gene Products in E. coli

Lysates of cells containing pDET1 and pDET2 were analyzed for the presence of the TA4 protein. Proteins synthesized by the pDET1 and pDET2 DNA were identified by probing Western blots of cell lysates with mouse antiserum raised against the reduced, denatured 17,000 dalton subunit of the E. tenella TA4 antigen.

Expression of pDET1 and pDET2 was analyzed first in E. coli strain W3110 (W3110 carries the wild-type Lon+ protease gene). Cultures of W3110/pDET1 and W3110/pDET2 were grown in L-broth (10 g/l tryptone (Difco), 5 g/l yeast extract (Difco), 5g/l NaCl, adjusted to pH 7.5 with NaOH) supplemented with 100 micrograms/ml ampicillin. To obtain optimum expression, cultures were shaken at 30° C. to a cell density of $1-5\times10^8$/ml, diluted 1:5 into fresh media and shaken at 37° for 2 to 6 hours. Cells were harvested by centrifugation, washed in M9 salts (6 g/l $Na_2HPO_4$, 3 g/l $KH_2PO_4$, 0.5 g/l NaCl, 1 g/l $NH_4Cl$) and resuspended at $5\times10^9$/ml in Laemmli gel sample buffer (35). Twelve microliter samples were heated 10 minutes, 100° C., and run on 12½% SDS-PAGE, and either stained with Coomassie Blue, or transferred to nitrocellulose sheets and probed with a 1:1000 dilution of mouse antiserum to reduced-denatured 17,000 dalton TA4 polypeptide as described above.

Expression of the TA4 gene in pDET1 and pDET2 is very low in E. coli strain W3110. The 25,000 dalton TA4 protein is visible only faintly on Western blots and not visible above background on Coomassie Blue stained polyacrylamide gels of total cell lysates, suggesting that net synthesis is less than 0.5% of total E. coli protein.

It appeared likely that the apparent low expression of pDET1 and pDET2 was due to instability of the TA4 protein in E. coli W3110. Other eukaryotic proteins have been shown to be unstable when synthesized in E. coli (18) Therefore, plasmids pDET1 and pDET2 were transformed into E. coli strain MTM6, deficient in the lon protease (7). MTM6 is a non-mucoid derivative of Lonstrain AB1899 (CGSC #1899).

Expression of the TA4 gene in pDET1 and pDET2 is greatly increased in strain MTM6 (Lon−) Expression was analyzed as described above for W3110. FIG. 9 compares synthesis of pDET1 in W3110 (Lon+) and MTM6 (Lon−). Strains containing either pDET1 pDET2 DNA produced a 25,000 dalton polypeptide that is immunoreactive with the mouse serum made against the reduced, denatured E. tenella TA4 antigen. These results suggest that whereas the 25,000 dalton protein encoded by the TA4 antigen gene is cleaved in E. tenella to a 17,000 dalton and 8,000 dalton polypeptide linked by a disulfide bond, this post-translational processing does not occur in E. coli.

When the lysates were separated into soluble and insoluble components by centrifugation, the vast majority of the 25,000 dalton protein was localized in the insoluble fraction of the cell lysate (FIG. 9). This insoluble protein does not appear immunoreactive with monoclonal antibody Ptn 7.2 A4/4 which recognizes the TA4 antigen in sporozoite membranes or extracted from sporozoite membranes without reduction of disulfide bonds.

Because the expression levels of pDET1 and pDET2 are very low in Lon+ E. coli and because Lon− E. coli might be impractical to grow in large scale cultures, the TA4 protein was stabilized by fusion to other proteins. Any suitable protein could be utilized for this protein fusion. The following examples illustrate only two of the possible proteins which are suitable; namely betagalactosidase and prochymosin.

EXAMPLE 11

Expression of the TA4 Protein as a Beta-Galatosidase Fusion Protein in E. coli

Construction of Beta-Galactosidase-TA4 Expression Plasmids

The observation that the greatest yield of the genetically engineered TA4 protein was obtained in a protease deficient strain suggests that the TA4 protein is subject to degradation in normal E. coli cells. TA4 gene fusion plasmids were constructed because attachment of the TA4 protein to a large protein can stabilize it in E. coli. Several eukaryotic proteins are more stable in bacteria as fused proteins (17, 27). Recombinant plasmid pBGC23 is a hybrid constructed for expression of a beta-galactosidase-TA4 antigen fusion protein. It was derived from a plasmid pDK2 which contains the lac regulatory region and virtually the whole beta-galactosidase gene (1008 codons) from lambda plac (22, 63) inserted into the EcoRI site of plasmid pBR328, and from the cDNA clone pTCD26. The construction of pBGC23 is diagramatically shown in FIG. 10. Suitable plasmids other than pDK2 can also be used. Plasmid pDK2 is one example of a suitable plasmid.

The 1276 bp EcoRI-BamHI fragment from pTCD26 containing the TA4 cDNA sequence was cloned into plasmid pDK2 that had been digested with EcoRI and BamHI to generate plasmid pDK22. Clone pDK22 contained the expected plasmid in which the TA4 cDNA sequence was fused to the C-terminal region of the beta-galactosidase coding sequence. However, in this plasmid the cDNA derived TA4 coding sequence is not in phase with that of beta-galactosidase. Therefore, plasmid pDK22 was digested with EcoRI and then treated with DNA polymerase I Klenow fragment and religated to put the TA4 coding sequences into the proper reading frame. This plasmid, designated pBGC23, contains a hybrid gene that encodes a protein consisting of the TA4 protein fused to the C-terminal region of beta-galactosidase (lacZ). pBGC23 was used to transform E. coli strains JM83, and REN3.

The recombinant DNA and its host microorganism described herein as REN3/pBGC23 was deposited with the American Type Culture Collection, Rockville, Md. and assigned ATCC Accession Number 53317. This deposit was made pursuant to the Budapest Treaty.

Expression and Analysis of Cloned Gene Products

Proteins encoded by the pBGC23 DNA were identified by probing Western blots of cell lysates with mouse serum against the purified reduced denatured 17,000 dalton subunit of the E. tenella TA4 antigen as described in Example 10. JM83/pBGC23 and REN3/pBGC23 were grown in L-broth, supplemented with 0.1% glucose and 100 micrograms/ml ampicillin. Cultures were grown to saturation by shaking at 37° C. overnight. Cells were harvested by centrifugation, washed in M9 salts and resuspended at $5 \times 10^9$/ml in Laemmli gel sample buffer. 20 microliter samples were heated 10 minutes at 100° C. and run on 7-½% SDS-PAGE, and either stained with Coomassie Blue or Western blotted.

Stained and immunoblotted gels (FIG. 11) demonstrated that the expected 135,000 dalton fusion protein is synthesized in JM83/pBGC23 and REN3/pBGC23 cultures but not in JM83 alone. The Western blot shows that the protein is immunoreactive with the mouse serum against the reduced, denatured E. tenella TA4 antigen. FIG. 11 shows the protein is present in the insoluble fraction of the cell lysate. Cultures grown as described above were lysed by sonication following lysozyme and EDTA treatment, and cell membranes were solubilized in 2% Triton overnight at 4° C. The insoluble material was collected by centrifugation, and the 135,000 dalton pBGC23 product was present in this fraction.

The pBGC23 protein is synthesized in E. coli at high levels, but is insoluble and does not react with monoclonal antibody Ptn 7.2 A4/4. Furthermore, this insoluble pBGC23 protein, when injected into mice will not raise antibodies that cross-react with native TA4 antigen.

EXAMPLE 12

Expression of the TA4 Protein as a Prochymosin Fusion Protein in E. coli

The proteins made by cells containing pDET1, pDET2 or pBGC23 are largely or totally insoluble, and thereby are apparently not active with monoclonal antibody Ptn 7.2 A4/4. It was observed that other eukaryotic proteins that are made in E. coli in an insoluble, inactive form can be solubilized and their activity recovered. One such protein is bovine prochymosin. The TA4 cDNA sequence was fused to the bovine prochymosin gene to produce an insoluble fusion protein that could be solubilized and made active by procedures developed for prochymosin alone. The extent of proper renaturation of the fusion protein could then be monitored by following chymosin activity.

A plasmid-encoded prochymosin-TA4 fusion protein was created by joining the TA4 cDNA sequence to the cloned bovine prochymosin gene of pWHA43, which directs synthesis of prochymosin in a stable but insoluble form in E. coli (47). Other plasmids may also be utilized. One suitable plasmid is pWHA43.

Figure 12:
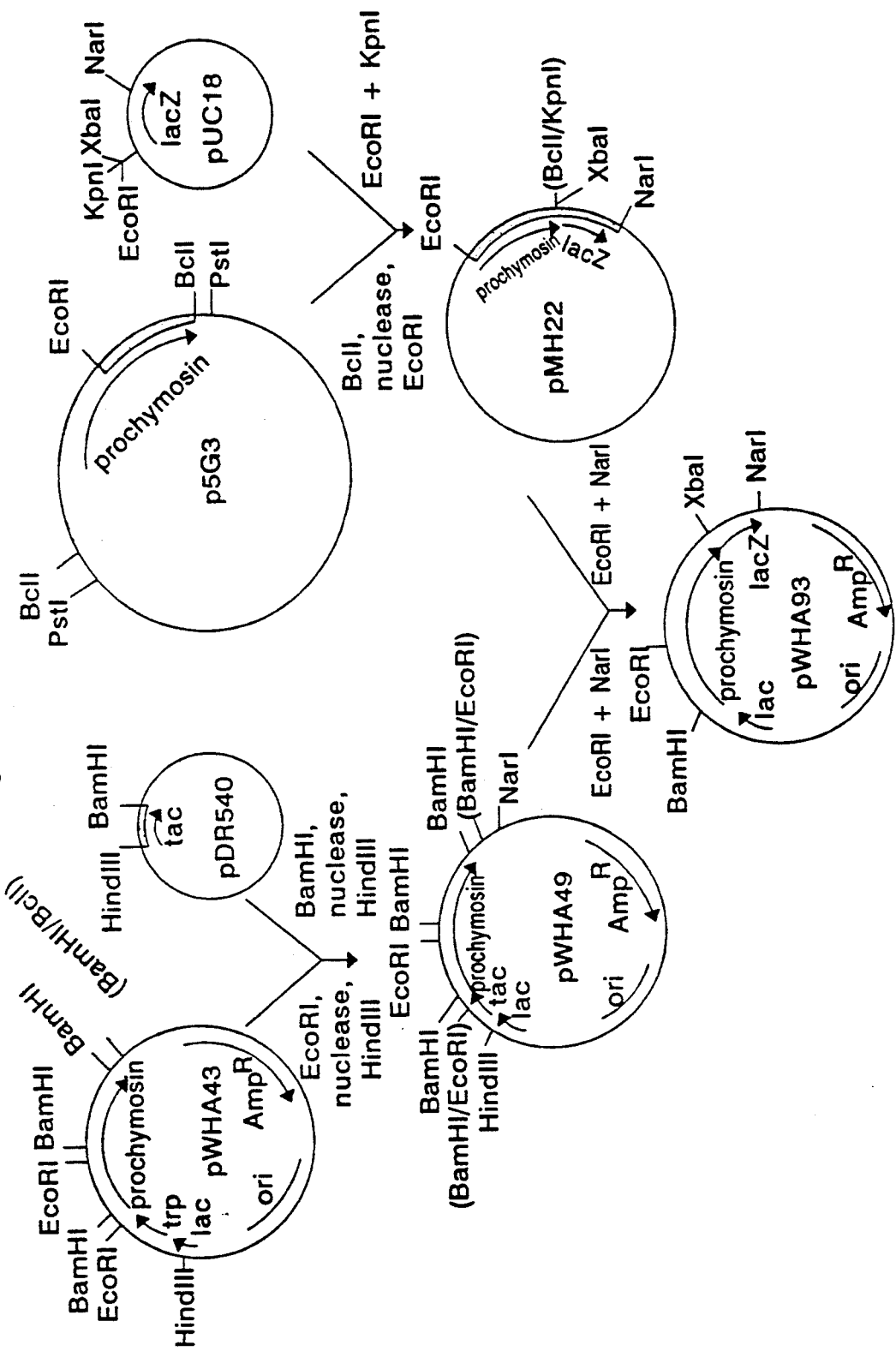
FIG. 12 schematically shows the construction of the bovine prochymosin expression vector pWHA93.

In order to construct the prochymosin-TA4 gene fusion, pWHA43 was converted to pWHA93 as shown in FIG. 12. First, the tac promoter of pDR540 (61) was substituted for the trp promoter to produce pWHA49 by specific restriction endonuclease substitution. Next, the normal stop codon of prochymosin was removed by substituting the C-terminal portion of the prochymosin gene of pWHA49 with a modified prochymosin C-terminal portion from pMH22, to give pWHA93. A spontaneous deletion resulted in the removal of the tac promoter from pWHA93. pMH22 contains the C-terminal half of the gene from the cDNA clone p5G3, fused to the prochymosin BclI site (deleting the stop codon) to the polylinker and beta-galactosidase gene fragment in plasmid pUC18.

In the construction of prochymosin-TA4 gene fusion, pCOC12, a 1294 bp fragment was removed from the cDNA clone pTCD26 by digestion with the enzymes EcoRI and PstI, followed by digestion with Mung bean nuclease to form blunt-ended DNA. The plasmid pWHA93 was digested with XbaI and treated with Mung bean nuclease and the blunt-ended vector was ligated with the blunt-ended fragment containing the TA4 cDNA sequences (1286 bp after Mung bean nuclease treatment) to generate the recombinant plasmid pCOC11. After this ligation, the TA4 derived sequences were found to be out of reading frame with the coding sequences of prochymosin. In order to change the reading frame, pCOC11 was digested with SacI and Mung bean nuclease, and was then religated to generate pCOC12. The construction of pCOC12 is diagrammatically shown in FIG. 13. Plasmid pCOC12 was modified to pCOC14 by removal of two NarI fragments by NarI digestion and religation, reducing the size of the plasmid but not deleting any of the prochymosin or TA4 sequences. Plasmid pCOC14 was modified to form pCOC20 by removal of a 249 bp SphI fragment by digestion with SphI and religation. The 249 nucleotide deletion in the prochymosin sequence of pCOC20 maintains the correct reading frame, and results in an 83 amino acid deletion in the prochymosin portion of the fusion protein.

For expression studies, pCOC12 and pCOC20 were transformed into strain REN3, a bacteriophage T1 resistant derivative of CY15001, a trp R derivative of W3110.

The recombinant DNAs and host microorganisms described herein as REN3/pCOC12 and REN3/pCOC20 were deposited with the American Type Culture Collection, Rockville, Md. and assigned ATCC Accession Numbers 53314 and 53313, respectively. These deposits were made pursuant to the Budapest Treaty.

Expression and Analysis of Cloned Gene Products

Proteins encoded by the pCOC12 and pCOC20 DNAs were identified immunologically, following fractionation by electrophoresis and transfer to nitrocellulose sheets as described in Example 10.

REN3/pCOC12 and REN3/pCOC20 were grown to saturation in L-broth supplemented with 0.1% glucose and 100 micrograms/ml ampicillin by shaking at 30° C. overnight Cells were harvested by centrifugation, washed in M9 salts and resuspended in Laemmli sample buffer. Samples were heated 10 minutes, 100° C. and run on 10% polyacrylamide gels in SDS and either stained with Coomassie Blue or transferred to nitrocellulose sheets for immunologic analysis, as described.

Triton insoluble material was prepared from REN3/pCOC12 and REN3/pCOC20 cultures as described in Example 11, and run on polyacrylamide gels.

The stained gels and Western blots shown in FIG. 14 show that pCOC12 DNA encodes a polypeptide of the expected molecular weight, approximately 65,600 daltons that is immunoreactive with the mouse serum against the reduced, denatured E. tenella TA4 antigen. As expected, the protein is present in the insoluble fraction of the cell lysate. Plasmid pCOC20 DNA encodes an immunoreactive polypeptide with the expected molecular weight of 56,500. The TA4 protein from pCOC20 is also present in the insoluble fraction of the cell lysate.

EXAMPLE 13

EXTRACTION OF THE TA4 PROTEIN FROM THE INSOLUBLE STATE AND DEMONSTRATION OF IMMUNOREACTIVITY WITH MONOCLONAL ANTIBODY Ptn 7.2 A4/4

The E. coli products of expression plasmids pDET1, pDET2, pBGC23, pCOC12, pCOC20 are all largely or totally insoluble. All can be solubilized by boiling in Laemmli sample buffer and react with mouse antiserum raised against the 17,000 dalton TA4 antigen subunit. However, none react with monoclonal antibody Ptn 7.2 A4/4 under these conditions. Therefore, it was necessary to solubilize and renature these E. coli synthesized proteins to produce antigens in a form that would react with monoclonal antibody Ptn 7.2 A4/4 and therefore could possibly raise neutralizing and protective antibody responses against E. tenella in animals.

Extraction and Renaturation of Bacterially Produced TA4 Proteins

First the pCOC12 protein was solubilized and renatured by methods known to solubilize and renature bovine prochymosin to produce active enzyme (47). This procedure produced pure soluble pCOC12 protein that possessed both prochymosin activity (milk clotting after acid activiation to chymosin) and Ptn 7.2 A4/4 immunoreactivity. Conditions were optimized for recovery of immunoreactivity and are described below.

Plasmid pCOC12 was constructed, as described above, by fusing the 3' end of the coding sequence of bovine prochymosin to the 5' end of the coding sequence of the TA4 polypeptide. This plasmid was used to transform E. coli strain REN3 using standard techniques and ampicillin resistant colonies were purified and used for culturing. An ampicillin resistant colony from a freshly streaked agar plate was used to inoculate a 5 ml liquid culture containing L-broth and ampicillin at 100 micrograms/ml. The culture was grown for several hours at 37° C. with shaking until cells had grown to an easily visible turbidity. The 5 ml culture was transferred to a flask containing 1 liter of L-broth/ampicillin supplemented with 0.1% glucose. This culture was grown at 30° C. with shaking to stationary phase. Cells were collected by centrifugation and stored frozen at −70° C. 10 g of frozen cell paste of E. coli strain REN3 containing pCOC12 were suspended in 100 ml of 25 mM TrisHCl pH 8, 10 mM EDTA, 1 mg/ml lysozyme. After a short incubation, the lysed cells were further disrupted by sonication. Prochymosin synthesized in E. coli has been shown to be completely insoluble in cell lysates, even in the presence of non-ionic detergents which solubilize cell membranes and membrane proteins. Partial purification of the pCOC12-encoded prochymosin-TA4 fusion protein was achieved by centrifugation of the cell lysate at 10,000×g for ten minutes, followed by an overnight detergent extraction of the pelleted cell debris with a buffer solution containing 2% Triton X-100 detergent (Sigma Chemical Co., St. Louis, Mo.). The pCOC12 fusion protein remained insoluble and was collected by centrifugation.

This purification was improved slightly by additional washing of the insoluble material with the solution containing 2% Triton X-100. The pCOC12 prochymosin-TA4 protein was suspended in 6.3 or 12.6 ml of 10 mM sodium phosphate buffer at pH 7.5. The suspension is fully solubilized by the addition of solid urea to a final concentration of 6–8 M in a volume of 10 or 20 ml, respectively.

The resultant clear solution was diluted into 100 or 50 volumes, respectively of 10 mM sodium phosphate buffer adjusted to pH 11.0 to achieve a final volume of 1000 mls. The solution was mixed thoroughly and allowed to stand for 20 minutes at 15°–25° C. The pH of the solution was then titrated to pH 8.3 by addition of 0.2N HCl over a period of 3 minutes.

The resultant solution was left at room temperature for one hour or more prior to assay or storage. This solution contained approximately 100 micrograms/ml of the 65,600 dalton protein which was 80–90% pure. The sample was assayed for chymosin enzymatic activity or immunoreactivity with monoclonal antibody Ptn 7.2 A4/4 as detailed below.

Assay of chymosin activity was a convenient way to monitor recovery of properly renatured protein. Recovery of immunoreactivity with Ptn 7.2 A4/4 correlated well with recovery of chymosin activity from pCOC12 protein, as measured by milk-clotting activity following acid activation. Recovery of immunoreactivity of the pCOC12 protein is described below and shown in FIG. 15.

The other TA4 proteins and protein fusions described above were solubilized and renatured by the same or similar methods. Plasmid pCOC20 was constructed, as diagrammed in FIG. 13, by a SphI deletion within the prochymosin component of the pCOC14 fusion protein. This deletion maintained the correct reading frame within the gene fusion and had no effect on the insolubility or subsequent solubilization or renaturation of the pCOC20 fusion protein. While the pCOC20 fusion protein maintained immunoreactivity of its TA4 epitope, the deletion-containing prochymosin domain could not be activated to a form having milk clotting activity.

Plasmid pCOC20 was used to transform E. coli strain REN3 that was cultured as described above. The insoluble pCOC20 prochymosin-TA4 protein was isolated and renatured from 10 grams of frozen cell paste of REN3/pCOC20 as described above.

Plasmid pBGC23 was constructed, as diagrammed in FIG. 10, by fusing the 3' end of the coding sequence of E. coli beta-galactosidase to the 5' end of the coding sequence of the cDNA derived TA4 polypeptide. This plasmid was used to transform *E. coli* strain JM83 (cultured as described above). The beta-galactosidase-TA4 fusion polypeptide was found to be insoluble within a cell lysate and was isolated and renatured from 10 gms of frozen cell paste of JM83/pBGC23 by the methods described above. Plasmid pDET2 was constructed, as diagrammed above, so as to express the TA4 protein directly rather than as a fusion polypeptide. Optimal yield of the pDET2 was achieved in a protease deficient *E. coli* strain MTM6. This strain was cultured as described above with the following exception. When the 1 liter culture of cells grown at 30° C. reached an optical density of 0.5 (Abs at 600 nm) the temperature was raised to 37° C. for 1 to 2 hours. The cells were harvested and stored frozen at −70° C.

10 grams of frozen cell paste of MTM6/pDET2 were lysed using the methods described above, and the Triton insoluble protein was isolated and dissolved in urea as described above. The solubilized protein was renatured by extensive dialysis against 10 mM sodium phosphate buffer, pH 8.5.

Immunoassay of Renatured Samples

The immunoreactivity of the renatured pCOC12, pCOC20, pDET2 and pBGC23 proteins with monoclonal antibody Ptn 7.2 A4/4 was measured relative to the TA4 antigen purified from *E. tenella* sporocysts. Each well of the microtiter plate (Immulon I microELISA flat-bottom well plates, Dynatech Laboratories, Inc., Alexandria Va.) was coated with 100 microliters antigen diluted in 10 mM $Na_2HPO_4$, 150 mM NaCl, 0.01% (w/v) Zwittergent 3-12, pH 8.0. For renatured samples, 1:10 to 1:1000 dilutions of the antigen were assayed. The purified *E. tenella* antigen was assayed in parallel at concentrations of 0.5–10 ng/well. Plates were coated with the antigens by incubation with the antigen solutions for 1 hour at room temperature and then overnight at 4° C. Wells were emptied and then washed three times with phosphate buffered saline pH 7.2 containing 0.02% (v/v) Tween-20 (PBST). The plates were treated with 3% (w/v) gelatin, 10 mM Tris-HCl pH 7.5, 150 mM NaCl, 0.05% (w/v) $NaN_3$ for 30 minutes at room temperature to block any remaining protein binding sites. Plates were then incubated with 100 microliters of monoclonal antibody Ptn 7.2 A4/4 (30 micrograms/ml in 3% [w/v] bovine serum albumin), 10 mM Tris-HCl pH 7.5, 150 mM NaCl, 0.05% (w/v) $NaN_3$) for 2 hours at room temperature. After rinsing the wells three times with PBST, the bound monoclonal antibody Ptn 7.2 A4/4 was determined using the Vectastain ™ ABC Kit for mouse IgG (Vector Laboratories, Inc., Burlingame, Calif.). Each well of the plate was filled with 100 microliters of biotinylated horse anti-mouse IgG (40 microliters biotinylated antimouse antibody, 80 microliters normal horse serum in 10 ml PBST) and incubated 30 minutes at room temperature. Plates were rinsed three times with PBST. Plates were then incubated bated with 100 microliters/well of Vectastain ™ ABC Reagent for 30 minutes at room temperature (80 microliters Avidin DH Reagent A mixed with 80 microliters biotinylated horseradish peroxidase Reagent B in PBST preincubated for 30 minutes before addition to the plates). After five washes with PBST bound horseradish peroxidase was measured by the addition of 100 microliters substrate/well (0.1 mg/ml 2,2'-azino-bis-(3-ethylbenzthiazoline-6-sulfonic acid)) in 50 mM citrate/phosphate buffer pH 5.3, 0.015% (v/v) hydrogen peroxide). Plates were incubated in the dark at room temperature. The absorbance at 414 nm was measured 10–60 minutes after substrate addition in a Titertek Multiscan ™ automatic plate reader (Flow Laboratories, Inc., McClean, Va.).

Figure 15:
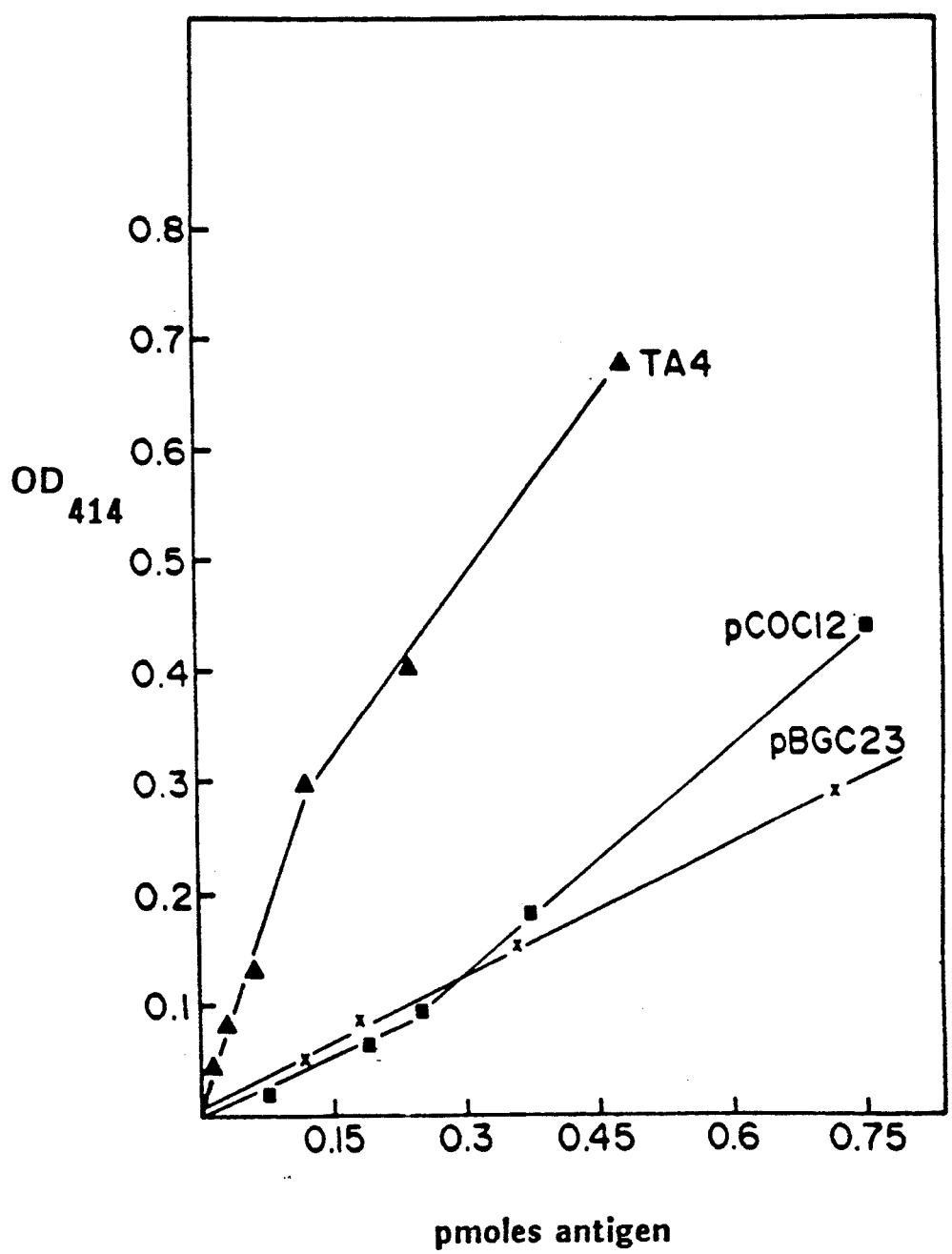
FIG. 15 demonstrates the immunoreactivity of the renatured bacterial TA4 proteins with monoclonal antibody Ptn 7.2 A4/4.
Figure 16:
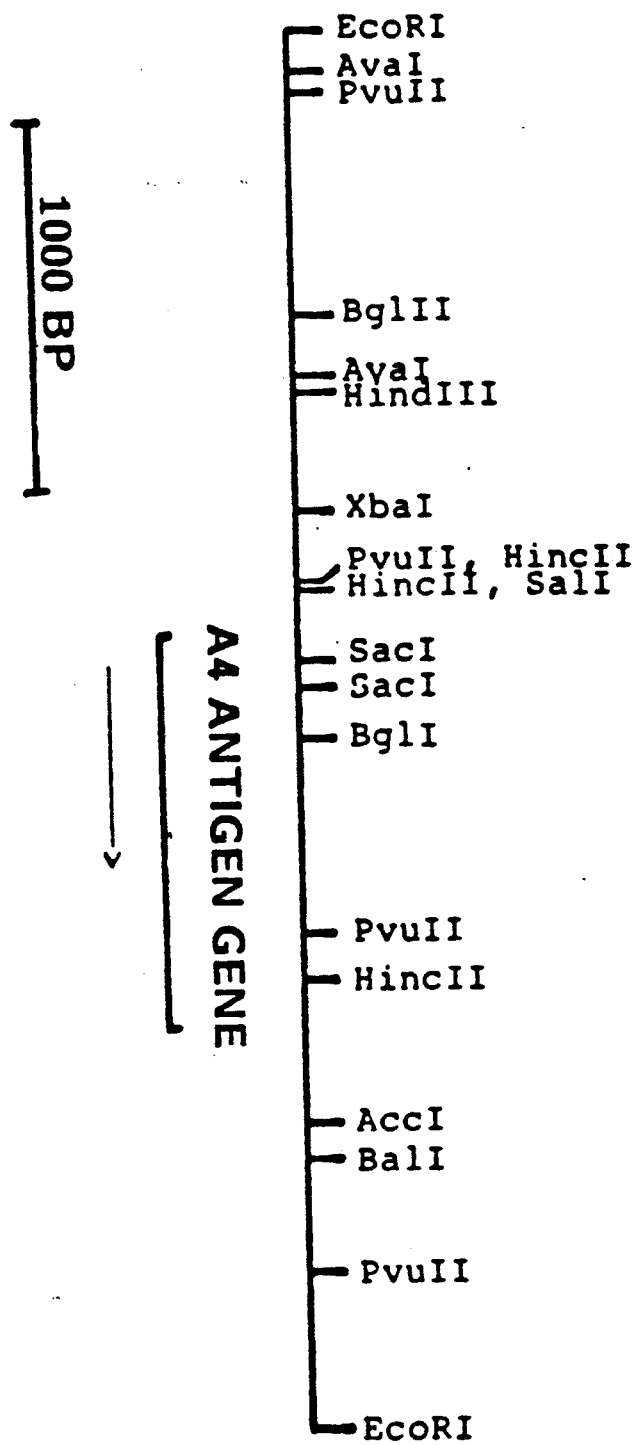
FIG. 16 displays the restriction enzyme map of the E. necatrix genomic clone 7-49 encoding the NA4 antigen and the position and orientation of the gene for the NA4 antigen within the 3900 bp E. necatrix EcoRI DNA fragment.
Figure 20:
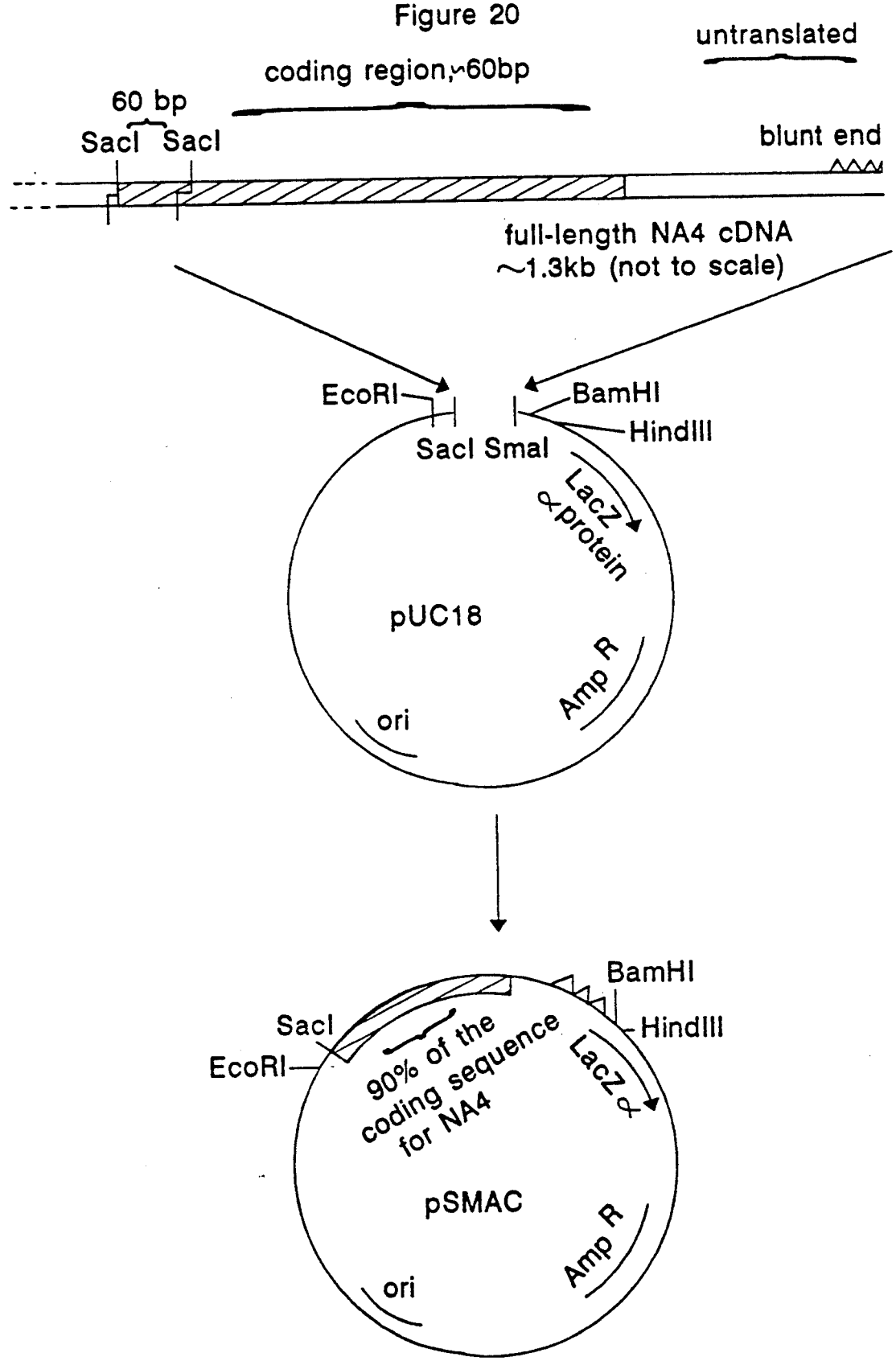
FIG. 20 schmatically shows the construction of the recombinant vector pSMAC.
Figure 22:
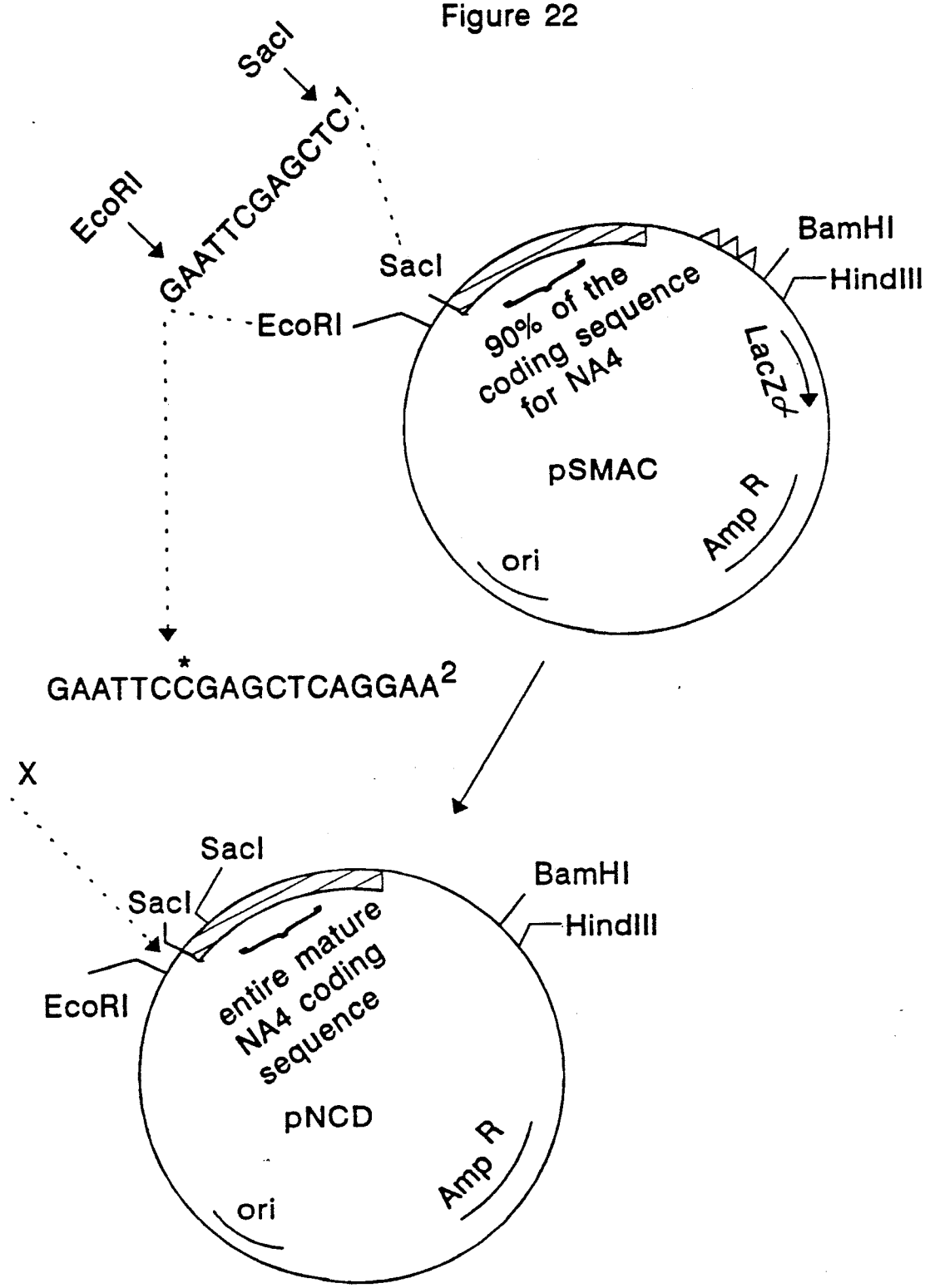
FIG. 22 schmetically shows the construction of the recombinant vector pNCD.
Figure 23A:
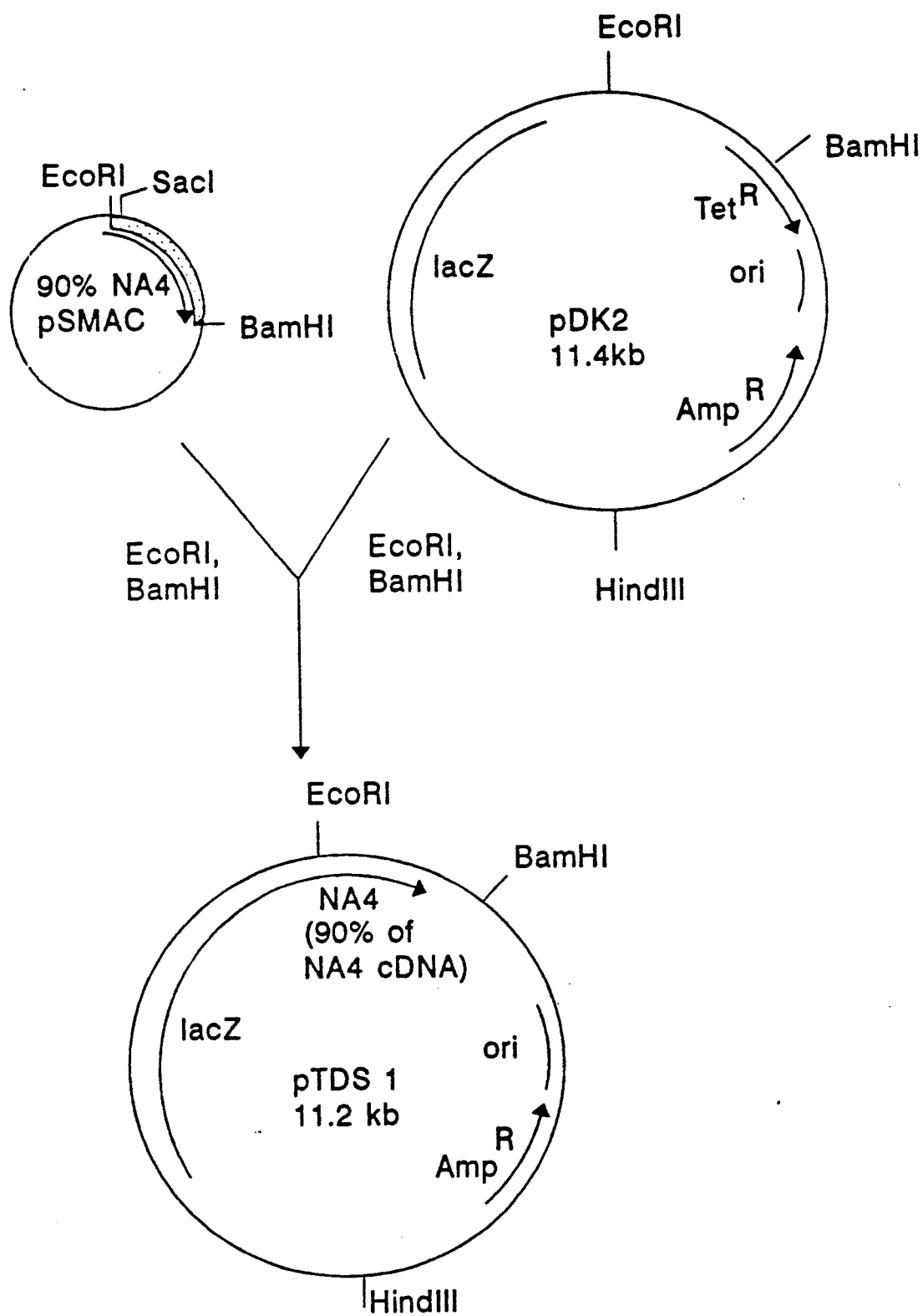
FIG. 23 schematically shows the construction of expression vectors pTDS1(A) and pTDS2(B).
Figure 23B:
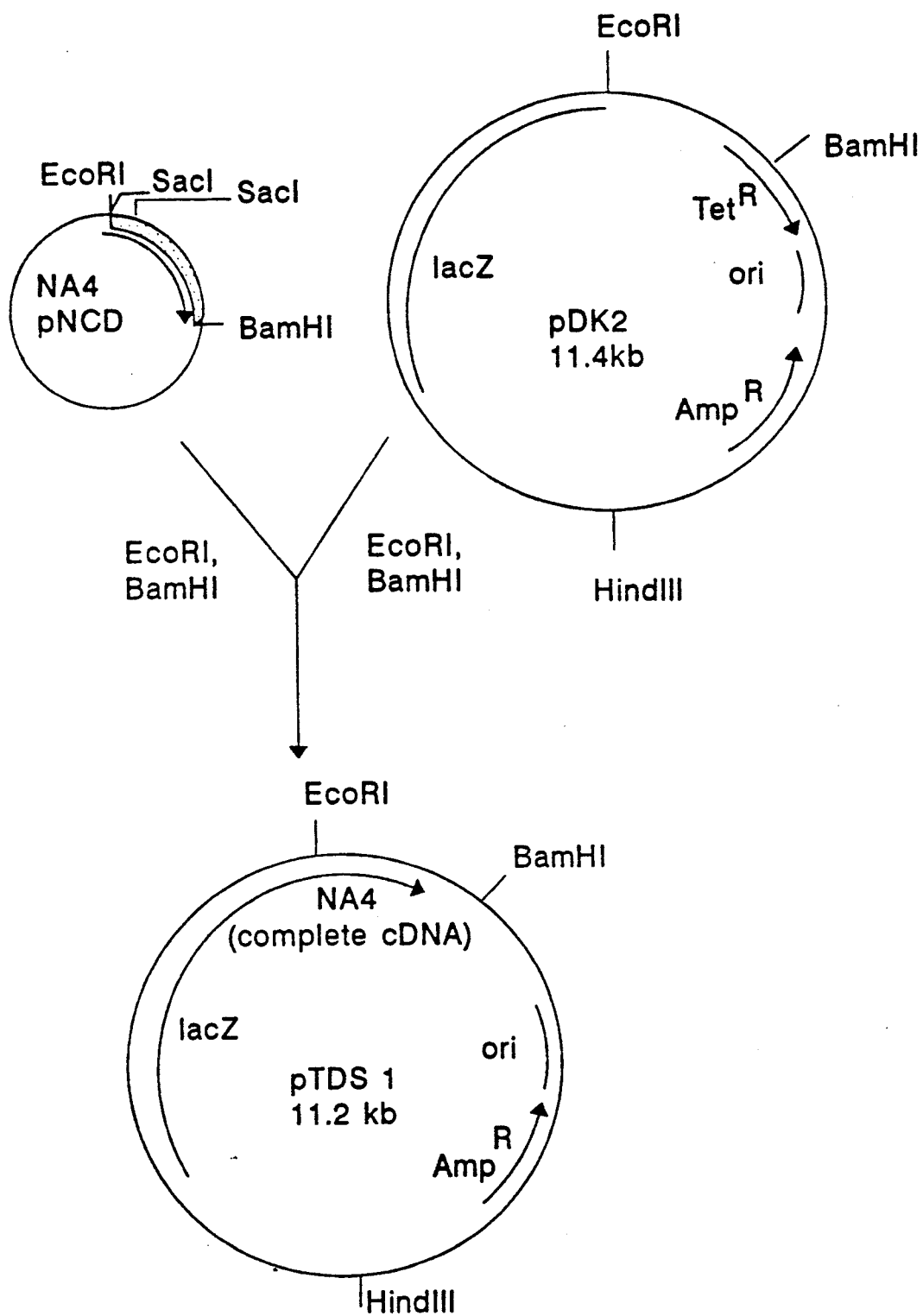
Figure 24A:
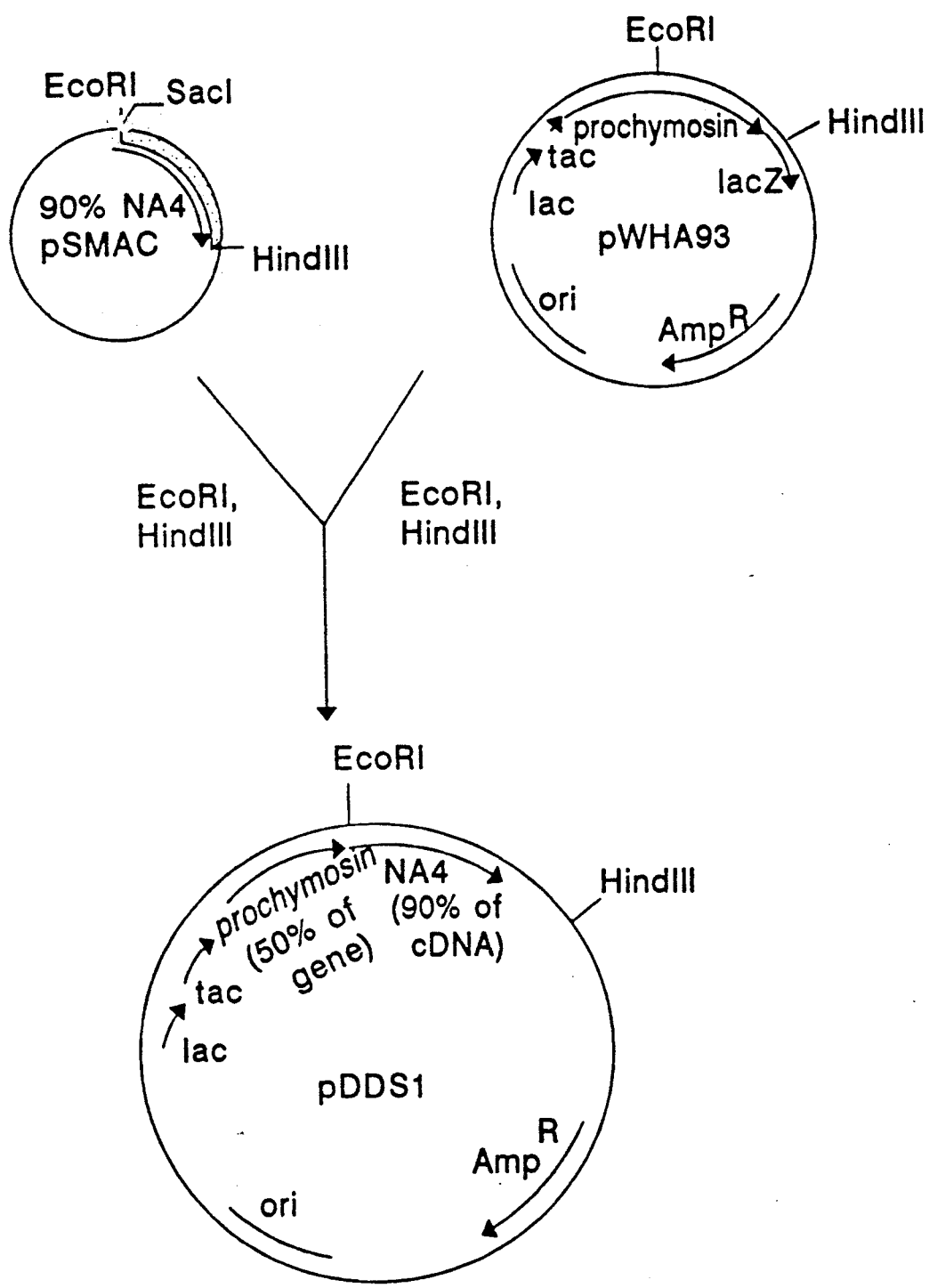
FIG. 24 schematically shows the construction of expression vectors pDDS1(A) and pDDS2(B).
Figure 24B:
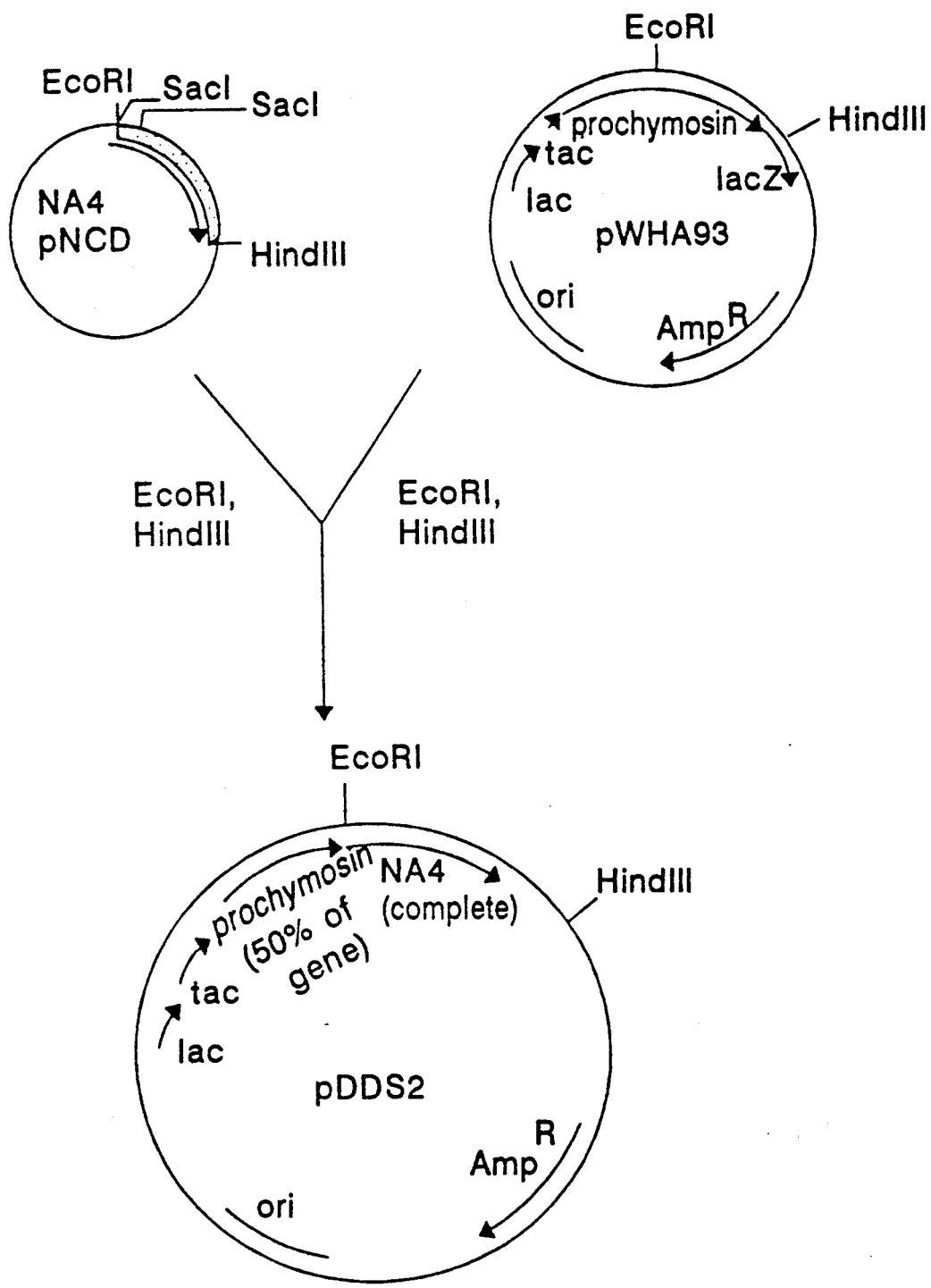

The relative immunoreactivities of the various renatured antigens (e.g., encoded by pBGC23, pCOC12, pCOC20 and pDET2) were compared with that of the TA4 antigen extracted from *E. tenella* oocysts. Increasing amounts of each protein were added to microtiter plate wells and the $OD_{414}$ of the reaction in each well was plotted against the antigen mass present (FIG. 15). The immunoreactivity of the bacterially-produced proteins subjected to the denaturation/renaturation treatment described above range between 10 and 30% of the activity of the *E. tenella*-extracted protein, on a molar equivalent basis.

EXAMPLE 14

Extraction of Immunoreactive Direct Expression TA4 Protein from the Insoluble State The *E. coli* products of expression plasmids pDET1, pDET2, pBGC23, pCOC12 and pCOC20 are all largely or totally insoluble. All can be solubilized by boiling in Laemmli sample buffer and react with mouse antiserum raised against the 17,000 dalton TA4 antigen subunit. However, none react with monoclonal antibody Ptn 7.2 A4/4 under these conditions. Therefore, it was necessary to solubilize and renature these *E. coli* synthesized proteins to produce antigens in a form that would react with monoclonal antibody Ptn 7.2 A4/4 and therefore could possibly raised neutralizing and protective antibody responses against *E. tenella* in animals.

Solubilization and renaturation of the TA4 antigenprochymosin fusion pCOC12 has been described.

Plasmid pDET2 was constructed, as diagrammed above, so as to express the TA4 protein directly rather than as a fusion polypeptide. Optimal yield of the pDET2 was achieved in protease deficient *E. coli* strains MTM6 and SG936.

Culture conditions were optimized for recovery of antigen and are described below.

The pDET2 protein was solubilized and renatured by methods known to solubilize and renature TA4 prochymosin fusions to produce immunoreactive antigen (Example 13). This procedure produced pure soluble pDET2 protein that possessed Ptn 7.2 A4/4 immunoreactivity.

Plasmid pDET2 was constructed, as described above. This plasmid was used to transform *E. coli* strain SG936 using standard techniques and ampicillin resistant colonies were purified and used for culturing. An ampicillin resistant colony from a freshly streaked agar plate was used to inoculate a 100 ml liquid culture containing L-broth and ampicillin at 100 micrograms/ml. The culture was grown overnight at 30° C. with shaking. The 100 ml culture was transferred to a flask containing 1 liter of L-broth/ampicillin. This culture was grown at 30° C. with shaking to $OD_{600}$ of 1.0. IPTG was added to 2 mM and the culture was grown 2–3 hours more at 30° C. Cells were collected by centrifugation and stored frozen at −70° C. 5 g of frozen cell paste of *E. coli* strain SG936 containing pDET2 were suspended in 40 ml of 25 mM Tris-HCl pH 8, 10 mM EDTA, 0.5 mg/ml lysozyme. After a short incubation, the lysed cells were further disrupted by sonication. Because the pDET2 protein synthesized in *E. coli* has been shown to be completely insoluble in cell lysates, pDET-encoded TA4 protein was purified by centrifugation of the cell lysate at 100,000×g for 1 hour, followed by a detergent extraction of the pelleted cell debris with a buffer solution containing 5% Triton X-100 detergent (Sigma Chemical Co., St. Louis, Mo.), 20 mM EDTA, for 60 minutes at 25° C. The pDET2 protein remained insoluble and was collected by centrifugation at 100,000×g.

The pDET2 insoluble material was suspended in 12 ml, 10 mM sodium phosphate (pH 7.5) and collected by centrifugation to remove remaining detergent. The pDET2 TA4 protein was suspended in 10 mM sodium phosphate buffer at pH 7.5 to a final volume of 7.7 ml. The suspension is fully solubilized by the addition of 5.8 g solid urea to a final volume of 1200 mls. The solution was mixed thoroughly and allowed to stand for 10 minutes at 150° C. The pH of the solution concentration of 8 M in a volume 12 ml, and then mixed for 16 hours at room temperature.

The resultant clear solution was diluted into 100 volumes of 10 mM sodium phosphate buffer adjusted to pH 11.0 to achieve a final volume of 1200 mls. The solution mixed thoroughly and allowed to stand for 10 minutes at 15° C. The pH of the solution was then titrated to pH 8.5 by addition of 0.5N HCl over a period of 5 minutes.

The resultant solution was left at room temperature for one hour or more prior to assay or storage. This solution contained approximately 10 micrograms/ml of the 25,000 dalton protein which was 50–60% pure. The sample was assayed for immunoreactivity with monoclonal antibody Ptn 7.2 A4/4 as detailed in Example 13. The preparation had activity comparable to renatured antigens from pBGC23 and pCOC12 described above. Protein was concentrated to 2 mg/ml for the vaccination studies, below.

EXAMPLE 15

Use of *E. tenella* TA4 Antigen and an 11,500 Dalton Fragment Thereof to Elicit Sporozoite Neutralizing Serum Response and Protective Response Against *E. tenella* in Chickens Eliciting Sporozoite Neutralizing Serum Response Against *E. tenella* Using the TA4 Antigen. The TA4 antigen used in these experiments was prepared from sporocysts by methods described in Example 4 for the preparation of the nonreduced intact TA4 antigen. Purity and identity of the protein was confirmed by SDS-PAGE and immunoreactivity with monoclonal antibody Ptn 7.2A4/4 prior to use in chickens.

Vaccine preparations were formulated at a level of one volume antigen to three volumes of oil carrier consisting of about 5% Arlacel A, 94% Drakeol 6-VR, 1% Tween 80 so that each 0.1 ml dose contained approximately 15 micrograms of TA4 antigen. When necessary, antigen was diluted with PBS (pH7.2) to the level desired for formulation. Chickens received 0.1 ml dose by intramuscular route in the neck muscle. Antigen was administered two more times by the same route using the same amount at two-week intervals.

Three days prior to each administration of protein, and eleven days after the final administration, birds were bled for collection of serum samples. Heat inactivated sera were tested independently in the sporozoite microneutralization assay as described in Example 2. Neutralization of parasites by serum was scored on the basis of the maximum serum dilution affording 50% inhibition of schizont development. The results as set forth below in Table I indicate that whereas nonvaccinated birds receiving carrier only had no demonstrable neutralizing antiserum titers against *E. tenella* sporozoites, birds receiving three doses of the antigen had demonstrable neutralizing antiserum titers.

TABLE I

TA4 Antigen Induced Sporozoite Neutralization Assay Data

| Serum Samples | Sporozoite Neutralization Titers (ND 50%)[d] Highest | Lowest | Median Titer |
|---|---|---|---|
| Prebleed[a] | N.D.[b] | N.D. | N.D. |
| Nonvaccinate Controls (n = 9) | N.D. | N.D. | N.D. |
| Carrier Only (n = 14) | N.D. | N.D. | N.D |
| Carrier/Protein Vaccine (n = 15) | 1:32 | N.D. | 1:8 |
| Immune serum[c] (Whole Sporozoite Vaccinates | — | — | 1:32 |

[a]Serums from birds within each treatment group were pooled and tested.
[b]N.D. = No detectable neutralization
[c]Pooled serum from several birds
[d]50% neutralization dose Eliciting a Protective Response in Chickens Using the TA4 Antigen. Sixty-three (63) days after the final vaccination, some birds were challenged, orally with 1,000 sporulated *E. tenella* oocysts. This was followed the next day with 3,000 sporulated *E. tenella* oocysts also given orally. Caecal lesions were scored 5 days after the final challenge. The results are tabulated below in Table II.

TABLE II

Protection of TA4 Antigen Vaccinated Birds Against *E. tenella* Coccidiosis

| | Lesion Score $\bar{\bar{X}}$ ± S.D. |
|---|---|
| Nonvaccinate Controls (n = 17) | 3.4 ± 0.6 |
| Adjuvant Only (n = 5) | 4.0 ± 0.0 |
| TA4 Antigen/Adjuvant Vaccinates (n = 8) | 2.4 ± 1.3 |

Eliciting Sporozoite Neutralizing Serum Response Against *E. tenella* Using the 11,500 dalton fragment of the TA4 Antigen. The immunogen used in these experiments was prepared from sporocysts by phenol extraction as described in Example 4. Purity and identity of the protein was confirmed by SDS-PAGE and immunoreactivity with monoclonal antibody Ptn 7.2A4/4 prior to use in chickens.

Lyophilized purified antigen was dissolved in 0.15 M phosphate buffered saline and emulsified in three parts carrier consisting of about 5% Arlacel A, 94% Drakeol 6-VR, 1% Tween-20 at a final antigen concentration of 70 micrograms/ml. Chickens received about 14 micrograms protein/0.2 cc dose by intramuscular route in the neck muscle. Antigen was again administered two weeks later by the same route using the same amount.

One day prior to each administration of protein, and two weeks after the second administration of protein, birds were bled for collection of serum samples. Heat inactivated sera were tested independently in the sporozoite microneutralization assay as described in Example 2.

The results as set forth below in Table III indicate that whereas nonvaccinated birds receiving carrier only had no demonstrable neutralizing antiserum titers against *E. tenella* sporozoites, birds receiving two doses of antigen had demonstrable neutralizing antiserum titers of up to 1:81.

TABLE III

Sporozoite Neutralizing Assay Data

| Serum Sample* | Bleeding | Sporozoite Neutralization Titers (ND 50%)[a] | | |
|---|---|---|---|---|
| | | Highest | Lowest | Median Titers |
| Prebleed | 0 Week | 1:3 | 1:3 | 1:3 |
| Nonvaccinate | 2 Weeks | 1:3 | 1:3 | 1:3 |
| Controls | 4 Weeks | 1:3 | 1:3 | 1:3 |
| Carriers only | 2 Weeks | 1:3 | 1:3 | 1:3 |
| | 4 Weeks | 1:3 | 1:3 | 1:3 |
| Carrier/Protein | 2 Weeks | 1:3 | 1:3 | 1:3 |
| Vaccine | 4 Weeks | 1:81 | 1:3 | 1:9 |
| Immune Serum** (Whole Sporozoite vaccine) | — | — | — | 1:81 |

*5 birds per group
**Pooled serum from several birds
[a]A 50% neutralizing dose

Eliciting a Protective Response in Chickens Using the 11,500 Dalton Fragment of the TA4 Antigen. Birds received approximately 3 micrograms of antigen in the aforementioned carrier one time in the neck muscle. A second group of birds received the carrier substance only. A final group of nonvaccinate (sentinel) birds were housed with each of the two aforementioned groups. Birds were exposed to coccidia by being housed in *E. tenella* contaminated cages. Approximately two weeks later, the birds were examined and found to have been infected by *E. tenella*. The results are shown in Table IV below.

TABLE IV

Protection of Vaccinate Birds Against Coccidiosis by *E. Tenella*

| Treatment | Lesion Score X̄ + S.D. | No. of Deaths |
|---|---|---|
| Adjuvant only (n = 5) | 3.8 + 0.4 | 2 |
| Antigen vaccination (n = 5) | 1.0 ± 0.8 | 0 |
| Sentinal Birds (n = 6) | 4.0 ± 0.0 | 6 |

Because the conditions described above closely mimic the natural means of exposure to *E. tenella* in the field, the data presented show clear evidence of the usefulness of the invention for protection against coccidiosis due to *E. tenella*.

Demonstration that Neutralizing Serum Antibodies of Chickens Recognize the 17,000 Dalton Polypeptide Component of the TA4 Antigen. Analysis of serum antibody specificity for the 17,000 dalton polypeptide component of the TA4 antigen was performed using Western blots (7, 59). All chicken sera with demonstrable neutralization titers to *E. tenella* sporozoites were shown to possess immunoglobulins with specificity for the 17,000 dalton peptide component of the TA4 antigen; conversely, no sera from nonresponding or control birds had specificity for the 17,000 dalton polypeptide or any other sporozoite protein.

Demonstration that Neutralization Serum Antibodies of Chicken Compete With Monoclonal Antibody Ptn 7.2A4/4. Sera from vaccinated birds with demonstrable neutralization titers to *E. tenella* sporozoites, as well as corresponding control sera were tested for the ability to compete with antibody Ptn 7.2A4/4 for binding sites on sporozoite membranes. Polystyrene 96 well clusters (Immulon II) were sensitized with 50 microliters of sporozoite membrane proteins in 10 mM glycine buffered saline, pH 9.6, at a level of approximately 100 micrograms total protein/ml. Serial two-fold dilutions of sera were prepared in 0.15M phosphate buffered saline with 0.0005% Tween-20 (PBs-Tw) containing a 1:80 dilution of alkaline phosphatase conjugated to Ptn 7.2A4/4 and then transferred to the sensitized plates at a final volume of 75 microliters/well. After incubation at 37° C. for 30 minutes, the plates were rinsed free of unreacted materials using PBS-Tw. Afterward, substrate consisting of the sodium salt of P-phosphonitrophenol dissolved in 1M diethanolamine buffer at a level of 1 mg/ml was added to each well of the plate to a final volume of 100 microliters. The resultant reaction product was monitored spectrophotometrically. From the study, it was possible to ascertain that sera from birds responding to the vaccination as evidenced by neutralization and immunoblots also contained antibody which competed with monoclonal antibody Ptn 7.2A4/4. This experiment provides direct evidence that antigen purified from sporozoite membranes by either immunoaffinity chromatography using monoclonal Ptn 7.2A4/4 or conventional chromatography is capable of stimulating an immune response in chickens to the epitope defined by monoclonal Ptn 7.2A4/4.

EXAMPLE 16

Use of *E. tenella* Protein to Elicit Sporozoite Neutralizing Serum Response Against *E. necatrix* in Chickens Heat inactivated sera from birds vaccinated with the 1,500 dalton containing preparation of the E. tenella TA4 antigen (Example 4) were pooled and tested in the neutralization assay (Example 2) substituting embryonic porcine lung cells. The results are as listed in Table V below.

TABLE V

| Treatment | Neutralization Titer |
|---|---|
| Non-immune chicken serum | 1:6 |
| TA4 Antigen Vaccination | 1:24 |
| *E. tenella* whole sperozoite immune serum | 1:48 |

The data demonstrate the development of an elevated serum neutralization titer against *E. necatrix* when birds receive the purified 11,500 dalton fragment of the TA4 antigen. Because it has been previously demonstrated that administration of the TA4 antigen results in the elevation of serum neutralizing titers to *E. tenella*, and that administration of the TA4 antigen results in protection from *E. tenella* challenge, and since *E. necatrix* sporozoite neutralization titers are elevated by the administration of TA4 antigen, one skilled in the art would predict that protection against *E. necatrix* challenge will also result from administration of the TA4 antigen.

EXAMPLE 17

Use of Bacterially Produced TA4 Proteins to Raise Serum antibodies in Mice That Cross React with the *E. tenella* TA4 Antigen The immunogenicity of bacterially-produced TA4 protein was tested by subcutaneous injections in CB6-F1 mice. Renatured pCOC12 and pBGC23 proteins as well as insoluble proteins from these constructs were tested. Purified *E. tenella* TA4 antigen was used as a positive control and renatured prochymosin (from strain REN3 containing pWHA49) as a negative control. A group of 5 mice was injected for each antigen. Mice were injected twice at a 35 day interval and bled about 10 days after each injection.

For the *E. tenella* TA4 antigen, 10 micrograms was injected subcutaneously per mouse in a mixture of 3 parts antigen solution to 5 parts complete Freund's adjuvant. (Final volume 200 microliters/injection). Renatured pCOC12 and pBGC23 proteins or insoluble proteins from these plasmids were similarly injected at approximately a twofold molar excess of the bacterial TA4 protein as compared to the *E. tenella* antigen.

Sera were assayed by the ELISA method described in Example 13. Microtiter plates were coated with 2ng of the purified *E. tenella* TA4 antigen/well. The results of the assay with sera from the second bleed are shown in the Table VI below.

TABLE VI

| Antisera Raised Against | Absorbance-Blank (414 nm)* ($\overline{X} \pm$ S.D.) |
|---|---|
| Renatured Prochymosin | 0 |
| Renatured pCOC12 Protein | 0.31 ± 0.06 |
| Insoluble pCOC12 Protein | 0.01 ± 0.01 |
| Renatured pBGC23 Protein | 0.29 ± 0.05 |
| Insoluble pBGC23 Protein | 0.03 ± 0.04 |
| *E. tenella* Purified TA4 | 0.36 ± 0.11 |

*5 mice/group; values for 1:3000 dilution of sera presented.

These experiments indicate that the mice immunized with pCOC12 or pBGC23 proteins that went through the renaturation protocol raised antibodies that cross-react with the purified *E. tenella* TA4 antigen. These sera gave a strong positive signal with the purified *E. tenella* TA4 antigen to at least a 1:3000 dilution. On the other hand, sera from mice injected with insoluble pCOC12 and pBGC23 proteins had essentially no cross-reacting antibodies to the *E. tenella* TA4 antigen even at sera dilutions as low as 1:30. These experiments indicate that the unpurified, non-renatured insoluble pCOC12 and pBGC23 proteins were not effective immunogens.

EXAMPLE 18

Use of Bacterially Produced TA4 Proteins to Elicit Sporozoite Neutralizing Serum Response and Protective Response Against *E. tenella* in Chickens It has been previously demonstrated that administration of the TA4 antigen purified from *E. tenella* (15 micrograms) produced serum antibodies that neutralized sporozoites in vitro and protected chickens against an *E. tenella* challenge. The renatured pCOC12 and pBGC23 proteins were tested for both these properties. Beta-galactosidase and renatured prochymosin were used as controls. Renatured pBGC23 protein, pCOC12 protein, and prochymosin were concentrated by dialysis against polyethylene glycol or by hollow fiber filtration (cartridge H1P10-20, Amicon Corp. Danvers, Mass.) to a final concentration of 0.5-2.0 mg/ml. Each antigen was formulated as one volume of protein concentrate to three volumes of oil carrier consisting of 5% Arlacel, 94% Drakeol 6-VR and 1% Tween 80. The dose of each antigen employed is listed in Table VII. The doses chosen contained approximately 0.5-2 times the molar amount of purified *E. tenella* native TA4 antigen previously shown to be effective in evoking an immune response.

TABLE VII

| ANTIGEN | MICROGRAMS/DOSE |
|---|---|
| Beta-galactosidase | 133 |
| Renatured pBGC23 Protein | 80 |
| Renatured pBGC23 Protein | 160 |
| Renatured Prochymosin | 53 |

TABLE VII-continued

| ANTIGEN | MICROGRAMS/DOSE |
|---|---|
| Renatured pCOC12 Protein | 80 |

In experiment 1, chickens received 0.2-0.55 cc of the appropriately formulated vaccine by intramuscular injection in the neck. Chickens received booster vaccinations by the same route two additional times separated by two-week intervals. In experiment 2, chickens received 0.2-0.45 cc of the appropriately formulated vaccine by injection into duodenal tissue. Chickens received one booster vaccination by the same route two weeks later. Three days prior to each administration of protein and eleven days after the final administration birds were bled for collection of serum samples.

Eliciting Sporozoite Neutralizing Serum Response Against *E. tenella*

Heat-inactivated sera from chickens in Experiments 1 and 2 were tested for neutralization of *E. tenella* sporozoites. The microneutralization assay was performed with primary chick kidney cell cultures as follows. One to two-week old chicks were sacrificed and aseptically nephrectomized. The kidneys were trypsinized, and cells plated into 96 well cultures at a density of approximately $10^4$/well in Earles LAH medium supplemented with 5% heat-inactivated fetal calf serum. Cultures were maintained at 41° C. in a 5% $CO_2$ atmosphere. When cell cultures reached a level of approximately 50% confluency, 50 microliters of appropriately diluted test serum was added to each well of the plate. Next, $2-3 \times 10^4$ sporozoites in 50 microliters of Earles culture medium were added to all wells of the plate. Twelve to sixteen hours later, the culture supernatant was replaced with fresh Earle LAH containing 2% heat inactivated fetal calf serum. The cultures were terminated at 40-44 hours post-infection. Culture supernatants were emptied from the plates at that time. Subsequently, cells were fixed to the plates by the addition of methanol, acidified with 5% glacial acetic acid. The fixed cultures were stained with 0.1% toluidine blue before examining. Wells were scored as to the approximate percentage of inhibition of schizogony. Neutralization of parasites was scored on the basis of the maximum serum dilution still producing complete inhibition of schizont development.

The results in Table VIII indicate that whereas birds vaccinated with beta-galactosidase or renatured prochymosin had no demonstrable neutralizing antiserum titers against *E. tenella* sporozoites, birds receiving three doses of pBGC23 protein or pCOC12 protein intramuscularly had demonstrable neutralizing antiserum titers.

TABLE VIII

| Serum Sample | | Geometric Mean Sporozoite Neutralizing Titers |
|---|---|---|
| Experiment 1: | Pre-bleed IM | 1:2.0 |
| | Adjuvant Only | 1:2.0 |
| | Beta-galactosidase | 1:2.0 |
| | Renatured pBGC23 Protein (80 micrograms) | 1:3.2 |
| | Renatured pBGC23 Protein (160 micrograms) | 1:2.6 |
| | Renatured Prochymosin | 1:2.0 |
| | Renatured pCOC12 Protein | 1:4.0 |

TABLE VIII-continued

| Serum Sample | Geometric Mean Sporozoite Neutralizing Titers |
|---|---|
| Sporozoite Immune | 1:16.0 |

Demonstration that Neutralizing Serum of Chickens Immunized with *E. coli*-Produced TA4 Protein Compete with Monoclonal Antibody Ptn 7.2 A4/4

Sera from vaccinated birds with demonstrable neutralization titers to *E. tenella* sporozoites, as well as corresponding control sera were tested for the ability to compete with antibody Ptn 7.2 A4/4 for binding sites on sporozoite membranes. Polystyrene 96 well plates (Immulon II) were incubated with 50 microliters of sporozoite membrane proteins in 10 mM glycine buffered saline, pH 9.6, at a level of approximately 100 micrograms total protein/ml overnight at 37° C. After washing plates three times with PBS-Tween (0.05% Tween-20) plates were incubated for 1 hour with 3% (w/v) bovine serum albumin (RIA grade, Sigma Chemical Co., St. Louis, Mo.) in PBS. Serial two-fold dilutions of sera from 1:2 to 1:200 were prepared in 0.15M phosphate buffered saline with 0.0005% Tween-20 and incubated with the plates for 3 hours at 37° C. Plates were then incubated with alkaline phosphatase conjugated Ptn 7.2 A4/4 monoclonal antibody for 1 hour at 37 ° C. The plates were rinsed free of unreacted materials using 0.15M phosphate buffered saline with (0.0005%) Tween-20. Afterward, 100 microliters of substrate solution consisting of 1 mg/ml sodium p-phosphonitrophenol in 1M diethanolamine buffer was added to each well. The resultant reaction product was monitored spectrophometrically. Sera from birds responding to the parenteral vaccination program, as evidenced by neutralization of sporozoites, contained antibody which competed with monoclonal antibody Ptn 7.2 A4/4 (Table IX). This experiment provided direct evidence that renatured pBGC23 and pCOC12 proteins were capable of stimulating an immune response in chickens to a region of the TA4 antigen recognized by monoclonal antibody Ptn 7.2 A4/4.

TABLE IX

| Ptn 7.2 A4/4 Competition titers (50% Inhibition) | | |
|---|---|---|
| | | Reciprocal Titer |
| Experiment 1: | Pre-bleed | 0 |
| | Beta-galactosidase | 0 |
| | Renatured pBGC23 Protein (80 micrograms) | 6.5 |
| | Renatured pBGC23 Protein (160 micrograms) | 6.5 |
| | Renatured Prochymosin | 0.6 |
| | Renatured pCOC12 Protein (80 micrograms) | 13.1 |
| | Renatured pCOC12 Protein (40 micrograms) | 9.9 |
| | Native TA4 | 14.6 |

Immunization with Various TA4 Proteins Reduced the Severity of Infection in Chickens Challenged with E. tenella Eleven days after the last vaccination, chickens were challenged with a low level of coccidia (ca. 300-500 oocysts) and maintained in floor pens. The bedding was not removed so as to maximize oocyst recycling. Chickens received a second challenge of 4000-5000 oocysts one week after the primary challenge to maximize uniformity of lesion development. Chickens were sacrificed 6 days later for evaluation of lesion development. Lesion scores were assessed by the parameters established by Johnson and Reid (30).

The results in Table X demonstrate that birds vaccinated with renatured pBGC23 or pCOC12 protein developed less severe lesions following challenge than did the corresponding control groups. Vaccination with either renatured pBGC23 or pCOC12 protein not only abolished the development of the most severe lesions (level=4) but also shifted the distribution of lesion severity to lower values. Approximately 50-70% of vaccinated birds registered lesions of 1-2 whereas 50-70% of the control birds had lesion scores of 3-4.

TABLE X

| Treatment | % Distribution Lesion Scored | | | | |
|---|---|---|---|---|---|
| | 0 | 1 | 2 | 3 | 4 |
| Experiment 1 | | | | | |
| Beta-galactosidase | 0 | 0 | 22.2 | 50.0 | 27.8 |
| Renatured pBGC23 Protein (80 micrograms) | 0 | 13.8 | 38.5 | 61.5 | 0 |
| Renatured pBGC23 Protein (160 micrograms) | 0 | 30.8 | 38.5 | 30.8 | 0 |
| Renatured Prochymosin | 0 | 7.1 | 21.4 | 57.1 | 14.3 |
| Renatured pCOC12 Protein | 0 | 11.1 | 44.4 | 44.4 | 0 |
| Nonvaccinated Control | 0 | 0 | 12.5 | 68.5 | 18.8 |
| Experiment 2 | | | | | |
| Beta-galactosidase | 0 | 8 | 27 | 37 | 28 |
| Renatured pBGC23 Protein (160 micrograms) | 0 | 34 | 44 | 22 | 0 |
| Renatured Prochymosin | 0 | 0 | 29 | 29 | 42 |
| Renatured pCOC12 Protein | 0 | 42 | 14 | 14 | 30 |
| Nonvaccinated Control | 0 | 0 | 0 | 20 | 80 |

EXAMPLE 19

Response In Chickens To Exposure To Direct Expression Produced Recobminant Ta4(pDET) Antigen Serologic response of pDET vaccinated chickens to *Eimeria tenella* antigen. Experiments were conducted to demonstrate the immunoreactivity of pDET vaccinated chickens to the sporocyst derived membrane protein of *Eimeria tenella*. In one experiment, ten birds were vaccinated with 50 micrograms of renatured pDET antigen, a direct expression of produced protein, production of which is referred to in Example 10 and 13. Immunoreactivity of the protein was assayed and confirmed with the monoclonal antibody Ptn 7.2A4/4 prior to its incorporation in the experiment.

Vaccine was prepared using a 3:1 ratio of 5% Arlacel-A, 94% Drakeol 6-VR and 1% Tween 80 to pDET with 0.04 micrograms of LPS (three-dose study) or 50 micrograms PHA (one-dose study), and administered in a subcutaneous 0.5 ml dose in the neck behind the head. In one experiment starting with 2-week-old Leghorns, the vaccination regimen consisted of three doses at 10-day intervals. Birds were bled at this same interval and serum was collected and stored frozen. The second experiment used 4-day-old broilers, which were bled 5 days after vaccination. Controls for both experiments consisted of an inactive insoluble pDET adjuvant in the above carrier; adjuvant/carrier; and nonvaccinated controls.

Sera from the vaccinated and controls were analyzed for immune reactivity using Western blot against *Eimeria tenella* sporocyst protein as described in Example 13.

The results set forth in Table XI below indicate that 9 of 10 birds in the 3-dose study vaccinated with pDET antigen responded with a positive reaction at the appropriate molecular weight band 10 days after the initial exposure, with 10 of 10 reacting after the two subsequent exposures. After the second exposure to insoluble pDET, several birds became seropositive to TA4 antigen. In the one-dose experiment, 10 of 10 birds vaccinated with pDET seroconverted on Western blot analysis after 5 days. None of the LPS or challenge control birds became seropositive throughtout either test.

TABLE XI pDET Antigen Immunoreactivity Assay for Three and One-Dose Exposures

| Vaccine Group | 1st Bleed | 2nd Bleed | 3rd Bleed |
|---|---|---|---|
| pDET Antigen (n = 10) | 9/10 | 10/10 | 10/10 |
| Insoluble pDET (n = 10) | 0/10 | 8/10 | 10/10 |
| Adjuvant Control (n = 10) | 0/10 | 0/10 | 0/10 |
| Nonvaccinate Control (n = 10) | 0/10 | 0/10 | 0/10 |
| pDET (One Dose) Antigen (n = 10) | 10/10 | — | — |
| Adjuvant Control (One Dose) (n = 10) | 0/10 | — | — |

Protection of pDET vaccinated chickens from challenge with *Eimeria tenella* oocysts. Ten days following the 3-dose vaccination schedule outlined above, chickens were inoculated with *Eimera tenella* oocysts, and examined for pathognomonic lesions of the parasite. The four groups mentioned above (pDET antigen, insoluble pDET, adjuvant control, nonvaccinate controls) were exposed per Os to 6,000 sporulated oocysts 10 days after final vaccination. The inoculum had been previously titrated to result in the desired severity of lesion. Caecal lesions characteristic for the parasite were scored five days after challenge, as in Example 18. The results as shown in Table XII below demonstrate a reduction in severity of lesions, and decrease in mortality in the pDET antigen group as compared to the controls.

TABLE XII

Lesions Scores of pDET Vaccinated Chickens When Challenged with Eimeria Tenella Oocysts

| Treatment | Lesion Score X + s.d. | # Deaths |
|---|---|---|
| pDET Antigen (n = 10) | 3.2 ± 0.4 | 0 |
| Insoluble pDET (n = 10) | 3.4 ± 0.5 | 1 |
| Adjuvant Controls (n = 10) | 3.8 ± 0.4 | 3 |
| Nonvaccinate Controls (n = 10) | 3.9 ± 0.3 | 3 |

Sporozoite neutralizing serum response in chickens vaccinated with pDET TA4 antigen. A sporozoite neutralization assay (SNA) was utilized to assess the ability of pDET to confer parasite neutralizing capacity to the serum of vaccinated birds. Using the SNA protocol extablished in Example 18, the sera from the above mentioned one and three dose experiments were assayed for neutralizing sera.

As shown in Table XIII below, the pDET vaccinated birds demonstrated sporozoite neurtralizing capability conferred to their sera when compared with the proper controls.

TABLE XIII

Sporozoitye Neutralization Assay for pDET Vaccinated Birds

| Treatment Group | <1:4 | 1:4 | 1:16 | 1:18 | 1:32 |
|---|---|---|---|---|---|
| pDET Antigen (3 dose n = 8) | 0/8 | 1/8 | 3/8 | 4/8 | — |
| Insoluble pDET (3 dose n = 8) | 5/8 | 1/8 | 2/8 | — | — |
| Adjuvant Control (3 dose n = 8) | 6/8 | 2/8 | — | — | — |
| E. tenella Sporozoite Immune Sera (n = 2) | — | — | — | — | 2/2 |
| pDET Antigen (1 dose n = 4) | — | — | 2/4 | 2/4 | — |
| Adjuvant Control (1 dose n = 5) | 5/5 | — | — | — | — |

EXAMPLE 20

A vaccine for immunization of chickens against coccidiosis and other disease agents may be prepared from the genetically engineered *E. tenella* TA4 sporozoite membrane protein and an avian viral vaccine antigen, namely Infectious Bursal Disease Virus. A suitable carrier for this combination of antigens is 5% Arlacel A, 94% Drakeol 6-VR, 1% Tween-80. The vaccine may be prepared by formulating one part of an aqueous solution of antigen with 3 parts Arlacel A/Drakeol 6-VR to a final concentration of 10 to 200 micrograms of each antigen/dose. The vaccine may be administered to chickens of any age by any route, for example by the intramuscular route. Properly vaccinated birds are protected against disease, (including depressed performance or death), caused by field challenge with the species contained in the vaccine which includes at least one Eimeria antigen epitope.

EXAMPLE 21

Response Of Chickens To A Multi-Component Exposure Of Recombinant Eimeria Tenella (TA4) Antigen and Recombinant Eimeria Maxima Antigen An experiment was conducted to demonstrate the immunoreactivity of birds vaccinated with both *E. tenalla* (pCOC20) and *E. maxima* recombinant antigens (p5-3, p14-9, or p11-2). Birds were divided into groups receiving the following:

| Treatment Group # | Antigen | Quantity of Antigen |
|---|---|---|
| I | pCOC20 | 50 micrograms |
| II | p5-3 | 50 micrograms |
| III | p14-9 | 50 micrograms |
| IV | p11-2 | 50 micrograms |
| V | pCOC20 & p5-3 | 100 micrograms (50 micrograms each) |
| VI | pCOC20 & p14-9 | 100 micrograms (50 micrograms each) |
| VII | p5-3 & p14-9 | 50 micrograms (25 micrograms each) |

-continued

| Treatment Group # | Antigen | Quantity of Antigen |
|---|---|---|
| VIII | Adjuvant Control | — |
| IX | Unvaccinated | — |

Vaccines were formulated as described in Examples 42 and 43 using a 3:1 (v/v) ratio of carrier to antigen, with the addition of *Salmonella minnesota* LPS to a final concentration of 8 micrograms/ml, to a total antigen concentration of 100 micrograms or 200 micrograms per ml. This formulation was delivered as a 0.5 ml subcutaneous dose behind the head. Vaccination regimen began with 2-week leghorns which received 3 doses at 10-day intervals, with birds bled, and sera collected and stored frozen after each vaccination. Controls for the experiment consisted of carrier/LPS and nonvaccinated challenge birds.

Sera from the vaccinates and controls were assessed for immune reactivity against both *E. tenella* sporocyst derived membrane protein and *E. maxima* whole merozoite protein by Western blot analysis and by indirect fluorescent antibody staining.

Ten days following the last vaccination, all groups were initially inoculated per os with 500 *E. tenella* and/or 100 *E. maxima* infective oocysts followed five days later by a second challenge of 4000 *E. tenella* and 40,000 *E. maxima* infective oocysts. Cecal lesions of *E. tenella* and duodenal lesions of *E. maxima*, both pathognomonic for their respective pathogens, were scored five days after the second challenge.

Parasite neutralization assays were employed to assess the serum response of birds vaccinated with a combination of *E. tenella* and *E. maxima* recombinant antigens. Activity against *E. maxima* was assessed using an in vivo neutralization assay described in Example 33. The results are tabulated in Tables XXIV, XXV, XXVI and XXVII below.

TABLE XXIV

Lesion scored of recombinant TA4 and recombinant 8B5 immunoreactive antigen vaccinated birds when challenged with *E. maxima* oocysts (40,000)*

| Treatment Group | *E. maxima* Lesion Scores |
|---|---|
| I | 2.2 ± 0.62 |
| III | 2.56 ± 0.42 |
| IV | 2.5 ± 0.42 |
| VII | 2.39 ± 0.42 |
| I | 2.8 ± 0.27 |
| VIII | 2.75 ± 0.35 |
| IX | 2.75 ± 0.38 |

TABLE XXV

Lesion scores of recombinant TA4 and recombinant 8B5 immunoreactive antigen vaccinated birds when challenged with *E. tenella* (4,000) and *E. maxima* oocysts (40,000)*

| Treatment Group # | *E. tenella* Lesion Scores | *E. maxima* Lesion Scores |
|---|---|---|
| VI | 2.56 ± 0.82 | 2.37 ± 0.58 |
| V | 2.83 ± 0.66 | 2.28 ± 0.36 |
| VIII | 3.75 ± 0.35 | 3.5 ± 0 |
| IX | 2.87 ± 0.63 | 2.5 ± 0.71 |

TABLE XXVI

Lesion scores of recombinant TA4 and recombinant 8B5 immunoreactive antigen vaccinated birds when challenged with *E. tenella* oocysts (4,000)*

| Treatment Group # | *E. tenella* Lesion Scores |
|---|---|
| I | 2.5 ± 0.84 |
| VIII | 3.5 ± 0.5 |
| IX | 3.0 ± 1.08 |

*Birds received a prechallenge with 100 *E. maxima* oocysts, 500 *E. tenella* oocysts or both 4 days prior to heavy challenge.

TABLE XXVII

In vivo *E. maxima* merozoite neutralization assay for renatured recombinant 8B5 immunoreactive antigen and recombinant TA4 antigen vaccinated birds.

| Treatment Group # | Oocyst Ouput % of Adjuvant | Mean Cyst Output/Bird ($\times 10^6$) |
|---|---|---|
| II | 15 | 23 |
| II | 26 | 38 |
| III | 18 | 27 |
| IV | 77 | 115 |
| V | 38 | 58 |
| V | 0 | 0 |
| VII | 69 | 104 |
| VI | 21 | 31 |
| I | 67 | 100 |
| VIII | 100 | 150 |
| IX* | 0 | 0 |

* = unchallenged

EXAMPLE 22

Weight Gain In Chickens Following Vaccination with pCOC20

Three different lots of pCOC20 (TA4) antigen were evaluated in a single dose vaccination/challenge study. Broilers were inoculated subcutaneously behind the neck with the antigen (100 micrograms) adjuvanted with PHA (50 micrograms). Vaccinations were at 5–6 days of age. Fourteen days later, the birds were bled, weighed, bile collected from selected birds, and inoculated per os with 5,000 sporulated *E. tenella* oocysts. The inoculum had been previously titrated to result in the desired severity of lesion. Six days after challenge, the birds were bled, reweighed and several birds were killed and lesions scored. The remaining birds were weighed again at 10 days after challenge. Lesion scores of vaccinated birds were not significantly different from those of nonvaccinated birds. Weight gains are presented in Table XXVIII below.

TABLE XXVIII

Weight Performance in pCOC20 Vaccinated Birds Following *E. tenella* Challenge

| | Percent Weight Gain $\overline{X}$ ± s.d. Days Post-Challenge | | |
|---|---|---|---|
| Treatment Group | 0–6 | 6–10 | 0–10 |
| Nonchallenged (n = 19) | 52 ± 5 | 29 ± 8 | 96 ± 10 |
| Nonvaccinated (n = 19) | 39 ± 6 | 28 ± 8 | 78 ± 10 |
| Adjuvant (n = 20) | 39 ± 6 | 28 ± 7 | 77 ± 9 |
| Chymosin (n = 19) | 40 ± 8 | 28 ± 7 | 79 ± 13 |
| pCOC20 (n = 17) | 41 ± 5 | 32 ± 5 | 86 ± 10 |
| pCOC20 (n = 16) | 43 ± 10 | 32 ± 8 | 88 ± 15 |
| pCOC20 (n = 15) | 41 ± 6 | 35 ± 9 | 90 ± 11 |
| pDET (n = 13) | 43 ± 3 | 35 ± 7 | 93 ± 11 |

The percent weight gains over the 10-day challenge period indicate that vaccination with pCOC20 provided a degree of protection upon challenge. The chymosin- /adjuvant and adjuvant only groups were no different than the nonvaccinated challenged group.

EXAMPLE 23

Vaccination/Challenge Weight Performance Trial pCOC20 Vs. *E. tenella*

A total of 144 birds (8 days of age) were divided into four groups of 36 birds each. The first group of birds was vaccinated subcutaneously with 0.5 ml of a water in oil emulsion containing 100 μg of pCOC20 antigen and 50 μg of PHA. The second group of birds received the same emulsion without antigen. The third and fourth groups of birds served as nonvaccinate controls. Birds were revaccinated at 18 days of age with 0.25 ml of emulsion containing 50 μg of pCOC20 antigen and 25 μg of PHA.

At 22 days of age, the first three groups of birds were challenged with 10,000 *E. tenella* oocysts followed two days later by 70,000 additional oocysts. The fourth group of birds were housed in a separate pen and remained unchallenged.

Figure 25:
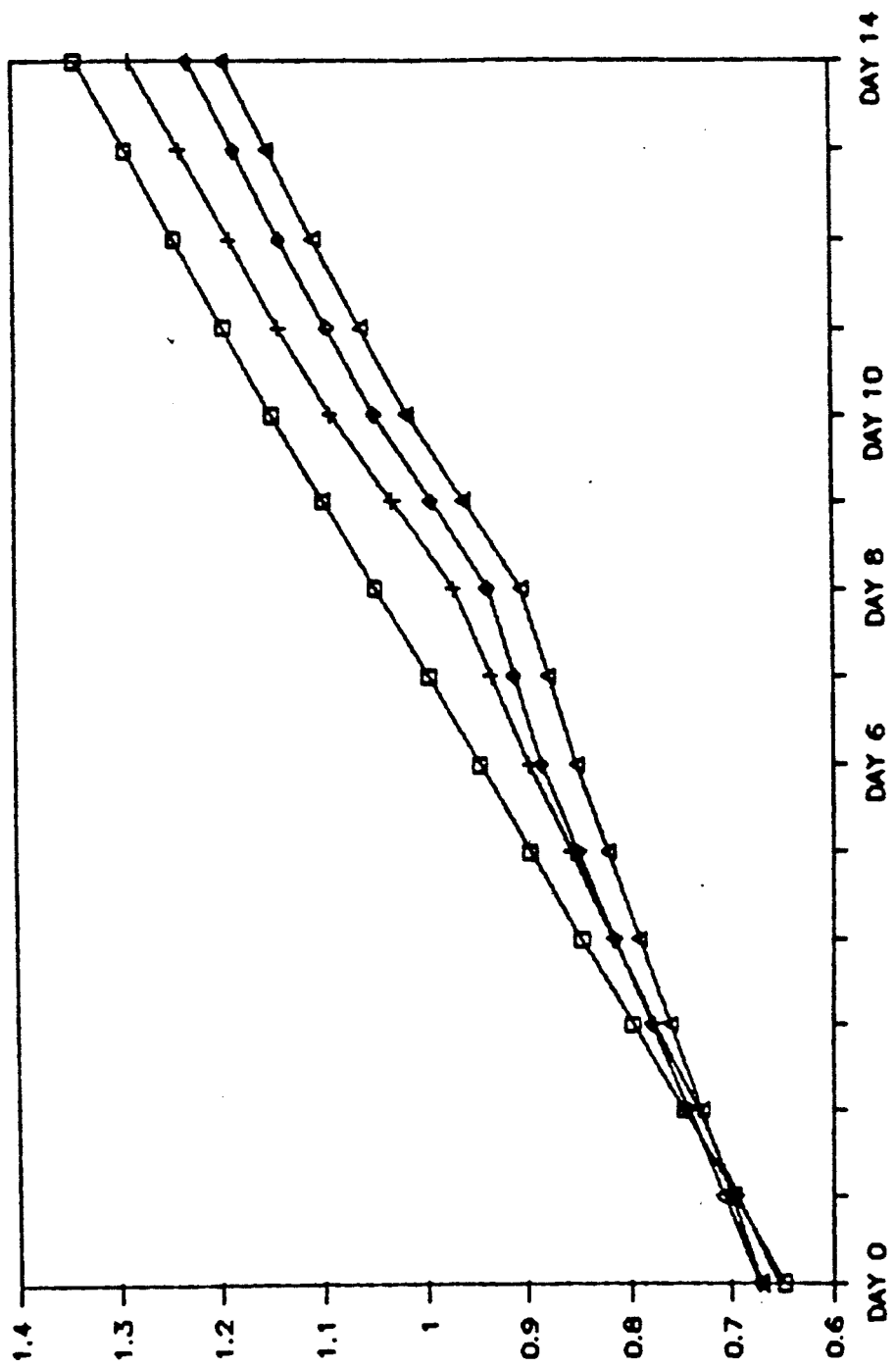
FIG. 25 shows the relative weight gain in vaccinated vs. nonvaccinate chickens after challenge with E. tenella oocysts.

The birds were weighed 6, 8, 10 and 14 days after the initial challenge. The data was analyzed by the Duncan multiple range test for statistical significance. The data as well as the statistical analysis appear in Table XXIX below and FIG. 25.

The results reveal that the vaccinate group out performed the other challenged control groups. At 14 days post-challenge, the vaccinate group was not significantly different from the control nonchallenged group and yet significantly heavier than the nonvaccinate challenge control birds. The birds receiving adjuvant only were significantly lighter than the nonchallenged controls but not significantly different from the nonvaccinate challenge control group. These results clearly demonstrate the protective nature of the pCOC20 antigen.

TABLE XXIX

STATISTICAL ANALYSIS OF INDIVIDUAL BIRD WEIGHTS DUNCAN M.R.T. WITH 95% C.I.

| Treatment Group | Days Post-challenge | | | | |
|---|---|---|---|---|---|
| | 0 | 6 | 8 | 10 | 14 |
| VAC/CH vs CTL/CH | NS | NS | S | S | S |
| VAC/CH vs CTL/NC | NS | S | S | S | NS |
| CTL/CH vs CTL/NC | NS | S | S | S | S |
| CTL/CH vs ADJ/CH | NS | NS | NS | NS | NS |
| ADJ/CH vs CTL/NC | NS | S | S | S | S |

S = Significantly Different
NS = Not Significantly different

REFERENCES

Ali, N. S., Binnerts, W. T. and Klimes, B. (1972). Immunization by (sic) irradiated *Eimeria acervulina*. J. Prot. 19, 177.

2. Aviv, H. and Leder, P. (1972). Purification of biologically active globin messenger RNA by chromatography on oligothymidylic acid cellulose. Proc. Natl. Acad. Sci. 69, 1408.

3. Benton, W. D. and Davis, R. W. (1977). Screening λgt recombinant clones by hybridization to single plaques in situ. Science 196, 180–182.

4. Blobel, G. and Dobberstein, B. (1975). Transfer of proteins across membranes I. Presence of proteolytically processed and unprocessed nascent immunoglobulin light chains on membrane-bound ribosome of murine myeloma. J. Cell Biol. 67, 835–851.

5. Burnette, W. M. (1981). "Western Blotting": Electrophoretic transfer of proteins from sodium dodecyl sulfate—polyacrylamide gels to unmodified nitro-cellulose and radiographic detection with antibody and radioiodinated protein A. Anal. Biochem. 112, 195.

6. Carlsson, M.; Hedin, A.; Inganaes, M.; Haerfast, B.; and Blomberg, F. (1985). Purification of in vitro produced mouse monoclonal antibodies. A two-step procedure using cation exchange chromatography and gel filtration. J. Immunol. Methods 79(1): 89–98.

7. Chung, C. H. and Goldberg, A. L. (1981). The product of the lon(capR) gene in *Escherichia coli* is the ATP dependent protease, Protease La. Proc. Natl. Acad. Sci. USA 78, 4931.

8. Cohen, S. A., Tarvin, T. L. and Bidlingmeyer, B. A. (1984). Analysis of amino acids using precolumn derivatization with phenylisothiocyanate. American Laboratory 16, 48–59.

9. Danforth, H. D. (1982). Development of hybridoma-produced antibodies directed against *Eimeria tenella* and *E. mitis*. J. Parasitol. 68, 392.

10. Danforth, H. D. (1982). Use of monoclonal antibodies directed against *Eimeria tenella* sporozoites to determine stage specificity and in vitro effect on parasite penetration and development. Am J. Vet. Res 44, 1722.

11. Danforth, H. D. and Augustine P. C. (1983). Specificity and cross-reactivity of immune serum and hybridoma antibodies to various species of avian coccicia. Poultry Science 62, 2145.

12. Davis, P. J., Parry, S. H. and Porter, P. (1978). The role of secretory IgA in anti-coccidial immunity in the chicken. Immunology 34, 879.

13. Davis, P. J. and Porter, P. (1979). A mechanism for secretory IgA mediated inhibition of the cell penetration and intracellular development of *Eimeria tenella*. Immunology 36, 471.

14. Edman, P. and Begg, G. (1967). A protein sequenator. Automated Equipment for Sequence determination, Eur. J. Biochem 1, 80.

15. Giambrone, J. J., Klesius, P. H. and Edgar S. A. (1980). Avian Coccidiosis: Evidence for a cell-mediated immune response. Poultry Sci. 59, 38.

16. Gibbons, R. A., Sellwood, R., Burrow, M. and Hunter, P. A. (1977). Inheritance of resistance to neonatal *E. coli* diarrhea in the pig: Examination of the genetic system. Theor. Appl. Genet. 51, 65.

17. Goeddel, D. V., Kleid, D. G., Bolivar, F., Heyneker, H. L., Yansura, D. G., Crea, R., Hirose, T., Kraszewski, A., Itakura, K. and Riggs, A. D. (1979). Expression in *Escherichia coli* of chemically synthesized genes for human insulin. Proc. Nat. Acad. Sci. USA 76, 106–110.

18. Goff S. A. and Goldberg A. L. (1985) Production of Abnormal Proteins in *E. coli* Stimulates Transcription of lon and Other Heat Shock Genes. Cell 41, 587–595.

19. Gore, T. C., Long, P. L., Kogut, M. and Johnson, J. (1983). Attenuation of *Eimeria necatrix* and *E. tenella* of U.S. origin by serial embryo passage. Avian Disease 27, 569.

20. Grunstein, M. and Hogness, D. S. (1975). Colony hybridization: A method for the isolation of cloned DNAs that contain a specific gene. Proc. Natl. Acad. Sci. USA 72, 3961.

21. Hagar, D. A. and Burgess, R. R. (1980). Elution of proteins from sodium dodecyl sulfate—polyacrylamide gels, removal of sodium dodecyl sulfate, and renaturation of enzymatic activity: Results with Sigma units of *Escherichia coli* RNA polymerase, wheat germ topoisomerase, and other enzymes. Anal. Biochem. 109:76.

22. Helling, R. B., Goodman, H. M. and Boyer, H. W. (1974) Analysis of Endonuclease EcoRI Fragments of DNA from Lambdoid Bacteriophages and other viruses by agarose gel electrophoresis. J. Virol. 14, 1235–1244.

23. Helms et al. (1985). DNA 4: 39–49.

24. Howard, R. J., Koushal, D. C. and Caster, R. (1982). Radio-iodination of parasite antigen with 1,3,4,6-tetrachloro-3,alpha-6,alpha-diphenyl glycouril (IODO-GEN TM) Studies with zygotes of *Plasmodium allinarum*. J. Protozol. 29:114.

25. Hunkapiller, M. W., Hewick, R. M., Dreyer, W. J. and Hood, L. E. (1983). High sensitivity sequencing with a gas phase sequenator. Methods in Enzymology 91, Academic Press, New York, 399–413.

26. Hunkapiller, M. W., Strickler, J. E. and Wilson, K. J. (1984). Contemporary Methodology for Protein Structure Determination. Science 226, 304–311.

27. Itakura, K., Hirose, T., Crea, R., Riggs, A. D., Heynechker, H. L., Bolivar, F. and Boyer, H. W. (1977). Expression in *Escherichia coli* of a chemically synthesized gene for the hormone somatostatin. Science 19 8, 1056–1063.

28. Jeffers, T. K. (1975). Attenuation of *Eimeria tenella* through selection for precociousness. J. Parasitol. 61, 1083.

29. Jeffers, T. K. (1976). Genetic recombination of precociousness and anticoccidial drug resistance on *Eimeria tenella*. Zeitschrift fur Parasitenkunde 50, 251.

30. Johnson, J. and Reid, W. M. (1970). Anticoccidial Drugs: Lesion scoring techniques in battery and floor pen experiments with chickens. Exp. Parasitology 38, 36.

31. Kasper, L. H., Crabb, J. H., and Pfefferkorn, E. R. (1983). Purification of a major membrane protein of *Toxoplasma gondii* by immunoabsorption with a monoclonal antibody. J. Immunol. 130, 2407.

32. Keusch, G. T. (1979). Specific membrane receptors: Pathogenic and therapeutic implications in infectious diseases. Rev. Inf. Dis. 1, 517.

33. Kleid D. G., Yansura, D., Small, B., Dowbenko, D., Moore, D. M., Grubman, M. J., McKercher, P. D., Morgan, D. O., Robertson, B. H. and Bachrach, H. L. (1981) Cloned viral protein vaccine for foot and mouth disease: responses in cattle and swine. Science 214, 1125.

34. Kriel, G. (1981). Transport of proteins across membranes. Ann. Rev. Biochem. 50, 317–348.

35. Laemmli, U. K. (1970). Cleavage of structural proteins during the assembly of the head of bacteriophage T4, Nature 227, 680.

36. Leder, P., Tiemeier, D. and Enquist, L. (1977). EK2 derivatives of bacteriophage lambda useful in cloning of DNA from higher organisms: the gt wes system. Science 196, 175–177.

37. Long, P. L. (1972) *Eimeria mivati*: Reproduction, pathogenicity and immunogenicity of a strain maintained in chick embryos by serial passage. J. Comp. Pathol. 82, 839.

38. Long, P. L. (1974). Further studies on the pathogenicity and immunogenicity of an embryo adapted strain of *Eimeria tenella*. Avian Pathology 3, 255.

39. Long, P. L. (1982). *The Biology of the Coccidia*. University Park Press, Baltimore. Pg. 44.

40. Long, P. L., Johnson, J., and Gore, T. C. (1982). Attenuation of a strain of *Eimeria mivati* of U.S. origin by serial embryo passage. Avian Diseases. 26, 305.

41. Long, P. L. and Rose, M. E. (1965). Active and passive immunization of chickens against induced infections of *Eimeria tenella*. Exp. Parasit. 16, 1.

42. Long, P. L., Millared, B. J., Joyner, L. P. and Norton, C. C. (1976). A guide to laboratory techniques used in the study and diagnosis of avian cocccidiosis. Folia Vet. Lat. 6, 201.

43. Lowder, L. J. (1966). Artificial acquired immunity to *Eimeria bovis* infections in cattle. Proc. Int. Congr. Parasit. 1, 106.

44. Maniatis, T., Fritsch, E. F. and Sambrook, J. (1982). *Molecular Cloning—A Laboratory Manual*, Cold Springs Harbor Laboratory, New York.

45. Marquardt, W. C. (1980). Host and site specificity in the Coccidia; a perspective. J. Protozool. 26, 243.

46. Maxam, A. and Gilbert, W. (1980). Sequencing end-labelled DNA with base-specific chemical change in: *Methods in Enzymology*, Vol. 65, part 1, Academic Press, New York, pp. 499–559.

47. McCaman, M. T., Andrews, W. H. and Files, J. G. (1985). Enzymatic properties and processing of bovine prochymosin synthesized in *Escherichia coli*. J. Biotech. 2, 177.

48. McDonald, V. and Ballingall, S. (1982). Attenuation of *Eimeria mivati* (: mitis) by selection for precocious development. Parasitology 86, 371.

49. McDonald, V. and Ballingall, S. (1982). Further investigation of the pathogenicity, immunogenicity and stability of precocious *Eimeria acervulina*. Parasitology 86, 361.

50. McDonald, V., Ballingall, S. and Shirley, M. W. (1982). A preliminary study of the nature of infection and immunity in chickens given an attenuated line of *Eimeria acervulina*. Parasitology 84, 21.

51. McDougald, L. R. Status of coccidiosis: New products on way. Poult. Digest. Oct., 1981.

52. McDougald, L. R. New anticoccidial drugs: Better things to come or "endangered species?" Feedstuffs Aug. 15, 1983.

53. Millar, W. T. and Smith, J. F. B. (1983). Protein iodination using IODO-GEN TM. Int. J. Appl. Radiot. Isol. 34:639.

54. Miller, L. H., Mason, S. J., Dvorak, J. A., McGinniss, M. H., and Rothman, I. K. (1975) Erythrocyte receptors of (*Plamodium knowlesi*) Malaria: Duffy blood group determinants. Science 189, 561.

55. Miller, J. H. ed. (1972). *Experiments in Molecular Genetics*. Cold Spring Harbor Laboratory, Cold Spring Harbor, New York, pages 54 and 431.

56. Norrander, J., Kempe, T. and Messing, J. (1983). Construction of improved M13 vectors using oligodeoxynucleotide—directed mutagenesis. Gene 26, 101.

57. Reid, W. M. (1978). Protozoa. In: *Diseases of Poultry*. 7th ed. M. S. Hofstad, ed. Iowa State Univ. Press. pp. 942–1054.

58. Riley, J. F. (1980). Screening for and evaluation of anticoccidial activity. Adv. Pharm. Chemo. 17, 1.

59. Rose, M. E. (1974). Immune responses to the Eimeria: Recent observations. Sympo. Coccidia and Related Organisms. pp. 92–118. Univ. Guelph, Ontario.

60. Rose, M. E. and Hesketh (1976). Immunity to Coccidiosis: Stages of the life cycle of *Eimera maxima* which induce and are affected by the host. Parasitology 27: 25–37.

61. Russell, D. R. and Bennett, G. N. (1982). Construction and analysis of in vivo activity of *E. coli* promoter hybrids and promoter mutants that alter the -35 to -10 spacing. Gene 20, 231-243.

62. Sanger, F. and Coulson, A. R. (1978). The use of thin polyacrylamide gels for DNA sequencing. FEBS Lett 87, 107-110.

63. Shapiro, J., MacHattie, L., Eron, L., Ihler, G., Ippen, K. Beckwith, J., Arditti, R., Reznikoff, W., and MacGillivray, R. (1969). The isolation of pure lac operon DNA. Nature 224, 768-774.

64. Sharma, S. D., Mullenax, J., Araujo, F. G., Erlich, H. A. and Remington, J. S. (1983). Western blot analysis of the antigens of *Toxoplasma gondii* recognized by human IgM and IgG antibodies. J. Immunology 131, 977.

65. Sharp, P. A. (1981). Speculations on RNA splicing. Cell 23;643-646.

66. Shirley, M. W. (1980) Eimeria necatrix: The development and characteristics of an egg-adapted (attenuated) line. Parasitology 81, 525.

67. Shirley, M. W. (1982). Features of an attenuated line of *Eimeria praecox*. Parasitology Proceedings of the British Soc. for Parasitology 81, 525.

68. Shirley, M. W., Bellatti, M. A. and Millard, B. J. (1982). An egg-shaped (attenuated) line of *Eimeria necatrix:* further studies on its reproduction pathogenicity and immunogenicity. Parasitology 84, 215.

69. Speer C. A. Wong R. B. and Schenkel, R. H. (1983). Effects of monoclonal IgG antibodies on *Eimeria tenella* (coccidia) sporozoites. J. Parasitol. 69, 775.

70. Speer, C. A., Wong, R. B. and Schenkel, R. H. (1983). Ultrastructural localization of monoclonal IgG antibodies for antigenic sites of *Eimeria tenella* oocysts, sporocysts and sporozoites. J. Protozoal. 30, 548.

71. Steiner, D. F., Quinn, P. S., Chan, S. J., Marsh, J. and Tager, H. S. (1980). Processing mechanisms in the biosynthesis of proteins. Annals N.Y. Acad. Sci. 343, 1-16.

72. Stotish, R. L., Wang, C. C., Hichens, M., Vanden-Heuvel, W. J. A. and Gale, P. (1976). Studies of a glycoprotein in the oocysts of *Eimeria tenella*. J. Biol. Chem. 251, 302.

73. Stotish, R. L., Profous-Juichelka, H. and Dulski, P. M. (1985). Isolation and in vitro translation of mRNA from *Eimeria tenella*. Fed. proc. 44; 1334.

74. Svennerholm, A., Lange, S. and Holmgrin, J. (1978). Correlation between intestinal synthesis of specific immunoglobulin A and protection against experimental cholera in mice. Inf. Imm. 21, 1.

75. Towbin, H., T. Staehelin and J. Gordon. (1979). Electrophoretic transfer of proteins from polyacrylamide gels to nitrocellulose sheets: Procedure and some applications. Proc. Nat'l Acad. Sci. 76:4350.

76. Ullrich, A. J., Shine, J., Chirgwin, J., Pictec, R., Tischer, E., Rutter, W. J. and Goodman, H. M. (1977). Rat insulin genes: Construction of plasmids containing the coding sequences. Science 196, 1313.

77. Van Deusen, R. A. and Whetstone, C. A. (1981). Practical aspects of producing anti-viral monoclonal antibodies as diagnostic reagents. Proc. Amer. Assn. Vet. Lab. Diagnost. 24, 211.

78. Viera, J. and Messing, J. (1982). The pUC plasmids, an M13mp7-derived system for insertion mutagenesis and sequencing with synthetic universal primers. Gene 19, 259-268.

79. Wang, C. C. Biochemistry and physiology of Coccidia. In *The Biology of the Coccidia*, Long, P. L., ed., (1982). University Park Press, Baltimore, pp. 167-228.

80. Wang, C. C. and Stotish, R. L. (1975). Changes in nucleic acids and proteins in the oocysts of *Eimeria tenella* during sporulation. J. Protozool. 22(3), 438.

81. Wisher, M. H. (1983). Sporozoite antigens of Coccidia. J. Cellular Biochem., Supp. 7A, Abstract 0059.

82. Wong, R. B. and Schenkel, R. H. (1984). Monoclonal antibodies analysis of *Eimeria tenella* sporozoite antigens. Fed. Proc. 184, 43(6), 1630.

83. Wright, I. G., White, M., Tracey-Patte, P. D., Donaldson, R. A., Goodger, B. V., Waltisbuhl, O. J. and Mahoney, D. F. (1983). *Babesia bovis:* Isolation of a protective antigen by using monoclonal antibody. Infection and Immunity 41, 244.

What is claimed is:

1. An isolated nucleic acid molecule encoding a 17,000 dalton antigenic protein derived from *Eimeria tenella* and having the amino acid sequence shown in FIG. 1.

2. The nucleic acid molecule of claim 1, wherein said molecule is an mRNA molecule.

3. The nucleic acid molecule of claim 1, wherein said molecule is a cDNA molecule.

4. An isolated nucleic acid molecule ending a 8,000 dalton antigenic protein derived from *Eimeria tenella* and having the amino acid sequence as follows: AlaAla-GlythrThrAspAlaValIleCysLeuThrAsnProAla-ProLeuGlu AlaArgSerGlnProPheAspAspGluGlnTrpLysLysIleValAspSerLeu SerLeuSerGluGluGluGlu-GluLysGlyGlyValSerProValValProSer ValAlaLeuIleSerAlaAlaValIleSerAlaPheAlaLeuPhe.

5. The nucleic acid molecule of claim 4, wherein said molecule is an mRNA molecule.

6. The nucleic acid molecule of claim 4, wherein said molecule is a cDNA molecule.

7. A recombinant cloning vector which comprises the isolated nucleic acid molecule of claim 5.

8. A recombinant cloning vector which comprises the isolated nucleic acid molecule of claim 4.

9. A bacterial hose cell which comprises the recombinant cloning vector of claim 7 or 8.

10. An expression vector which comprises the cDNA molecule of claim 3 operably linked to a promoter of DNA expression.

11. An expression vector which comprises the cDNA molecule of claim 6 operably linked to a promoter of DNA expression.

12. An expression vector which comprises a promoter of DNA expression operably linked to the 5' end of DNA encoding β-galactosidase, the 3' end of which DNA is directly linked to the 5' end of the cDNA molecule of claim 3.

13. An expression vector which comprises a promoter of DNA expression operably linked to the 5' end of DNA encoding β-galactosidase, the 3' end of which DNA is directly linked to the 5' end of the cDNA molecule of claim 6.

14. An expression vector which comprises a promoter of DNA expression operably linked to the 5' end of DNA encoding β-galactosidase, the 3' end of which DNA is directly linked to the 5' end of the cDNA molecule of claim 3.

15. The expression vector of claim 14, wherein the DNA encoding prochymosin contains a 249 base pair deletion.

16. An expression vector which comprises a promoter of DNA expression operably linked to the 5' end of DNA encoding β-galactosidase, the 3' end of which DNA is directly linked to the 5' end of the cDNA molecule of claim 6.

17. The expression vector of claim 16, wherein the DNA encoding prochymosin contains a 249 base pair deletion.

18. A bacterial host cell which comprises the expression vector as in any one of claims 10-17.

19. A method of preparing an antigenic protein derived from *Eimeria tenella* which comprises growing the bacterial hose cell of claim 18 under conditions permitting DNA expression and protein production followed by recovering the protein so produced.

20. The method of claim 19, wherein the recovery comprises:
 (i) separating the protein from the host cells;
 (ii) purifying the protein;
 (iii) solubilizing the protein;
 (iv) renaturing the protein; and
 (v) recovering the purified, solubilized and renatured protein.

* * * * *